United States Patent [19]
Barany et al.

[11] Patent Number: 5,830,711
[45] Date of Patent: *Nov. 3, 1998

[54] THERMOSTABLE LIGASE MEDIATED DNA AMPLIFICATION SYSTEM FOR THE DETECTION OF GENETIC DISEASES

[75] Inventors: Francis Barany; John Zebala, both of New York, N.Y.; Deborah Nickerson, Seattle, Wash.; Robert J. Kaiser, Jr., Seatlle, Wash.; Leroy Hood, Seatlle, Wash.

[73] Assignees: Cornell Research Foundation, Inc., Ithaca, N.Y.; California Institute of Technology, Pasadena, Calif.

[ * ] Notice: The term of this patent shall not extend beyond the expiration date of Pat. No. 5,494,870.

[21] Appl. No.: 462,221

[22] Filed: Jun. 5, 1995

Related U.S. Application Data

[63] Continuation of Ser. No. 343,785, Nov. 22, 1994, Pat. No. 5,494,810, Continuation of Ser. No. 971,095, Nov. 2, 1992, abandoned, which is a continuation-in-part of Ser. No. 518,447, May 3, 1990, abandoned.

[51] Int. Cl.$^6$ .............................. C12P 19/34; C12Q 2/68; C07H 21/00; C07H 21/04
[52] U.S. Cl. ........................... 435/91.1; 435/6; 435/91.2; 536/22.1; 536/23.1; 536/24.3; 536/25.32; 536/25.4
[58] Field of Search ............................ 435/6, 91.1, 91.2; 536/22.1, 23.1, 24.3, 25.32, 25.4

[56] References Cited

U.S. PATENT DOCUMENTS

| | | | |
|---|---|---|---|
| 4,683,202 | 7/1987 | Mullis | 435/91 |
| 4,749,647 | 6/1988 | Thomas et al. | 435/6 |
| 4,889,818 | 12/1989 | Gelfand et al. | 435/194 |
| 4,988,617 | 1/1991 | Landegren et al. | 435/6 |
| 5,242,794 | 9/1993 | Whiteley et al. | 435/6 |
| 5,494,810 | 2/1996 | Barany et al. | 435/91.52 |

FOREIGN PATENT DOCUMENTS

| | | |
|---|---|---|
| 130515 | 1/1985 | European Pat. Off. . |
| 246864 | 11/1987 | European Pat. Off. . |
| 0 320 308 | 6/1989 | European Pat. Off. . |
| 324616 | 7/1989 | European Pat. Off. . |
| 336731 | 10/1989 | European Pat. Off. . |
| 89/09835 | 10/1989 | WIPO . |

OTHER PUBLICATIONS

Perucho et al. "Genetic and Physical Linkage of Exogenous sequences in Transformed Cells", Cell, vol. 22, Part 1, pp. 309–317, Nov. 1980.

Barany, F. et al., "Genetic Disease Detection and DNA Amplification using Cloned Tehrmostable Ligase," *Proc. Natl. Acad. Sci. USA*, 88:189–93 (1991).

Barany, F., et al., "Cloning, Overexpression and Nucleotide Sequence of a Thermostable DNA Ligase–Encoding Gene," *Gene*, 109:1–11 (1991).

Takahasi, M., et al., "Thermophillic HB8 DNA Ligase: Effects of Polyethylene Glycols and Polyamines on Blunt–End Ligation of DNA," *J. Biochem.*, 100:123–31 (1986).

Takashi, M., et al., "Note—Purification of HB8 DNA Ligase by Red Sepharose Chromatography," *Agric. Biol. Chem.*, 50(5):1333–34 (1986).

(List continued on next page.)

*Primary Examiner*—Ardin H. Marschel
*Assistant Examiner*—Jezia Riley
*Attorney, Agent, or Firm*—Nixon, Hagargrave, Devans & Doyle LLP

[57] ABSTRACT

The present invention relates to the cloning of the gene of a thermophilic DNA ligase, from *Thermus aquaticus* strain HB8, and the use of this ligase for the detection of specific sequences of nucleotides in a variety of nucleic acid samples, and more particularly in those samples containing a DNA sequence characterized by a difference in the nucleic acid sequence from a standard sequence including single nucleic acid base pair changes, deletions, insertions or translocations.

89 Claims, 8 Drawing Sheets

OTHER PUBLICATIONS

Lauer, G., et al., "Cloning, Nucleotide Sequence, and Engineered Expression of *Thermus Thermophilus* DNA, a Homolog of *Escherichia coli* DNA Ligase," *J. Bacteriology*, 173(16):5047–53 (1991).

Lawyer, F.C., et al., "Isolation, Characterization, and Expression in *Escherichia coli* of the DNA Polymerase Gene from *Thermus Aquaticus*," *J. Bio. Chem.*, 264(11):6427–37 (1989).

Taguchi, H., et al., "A Chaperonin from a Thermophillic Bacterium, *Thermus Thermophilus*, That Controls Refoldings of Several Thermophillic Enzymes," *J. Biol. Chem.*, 266(33):22411–18 (1991).

Schalling, M., et al., "Direct Detection of Novel Expanded Trinucleotide Repeats in the Human Genome," *Nature Genetics*, 4:135–39 (1993).

Caskey, C.T., "Molecular Medicine—A Spin–off From the Helix," *JAMA*, 269:1986–93.

Chariot, A.C., et al., "Identification of an Expressed HOXB7 Stop Codon Polymorphism in the Human Breast Cancer–Derived Cell Line MCF7 by Reverse Transcriptase–Ligase Chain Reaction," National Cancer Institute, Bethesda, MD (1993).

Weiss, R., "Hot Prospect for New Gene Amplifier," *Science*, 254:1292–3 (1991).

Birkenmeyer, L.G., et al., "Mini–Review—DNA Probe Amplification Methods," *J. Virol. Methods*, 35:117–26 (1991).

Holding, C., et al., "Diagnosis of Beta–Tiialassaemia by DNA Amplification in Single Blastomeres from Mouse Preimplantation Embryos," *The Lancet* pp. 532–535 (1989).

Wu, D.Y., et al., "The Ligation Amplification Reaction (LAR)—Amplification of Specific DNA Sequences Using Sequential Rounds of Templates–Dependent Ligation," *Genomics* 4:560–569 (1989).

Takahashi, M., et al., "Thermophilic DNA Ligase Purification and Properties of the Enzyme from *Thermus Thermopilus* HB8," *J. Biol. Chem.*, 259:10041–10047 (1984).

Barringer, K.J., et al., "Blunt–End and Single–Strand Ligations by *Escherichia coli* Ligase: Influence on an in vitro Amplification Scheme," *Gene*, 89:117–22 (1990).

Matsuzawa, H., et al., "Purification and Characterization of Aqualysin I (a Tehrmophilic Alkaline Serine Protease) Produced by *Thermus Aquaticus* YT–1," *Eur. J. Biochem.*, 171:441–47 (1988).

Winn–Deen, E.S., et al., "Sensitive Fluorescence Method for Detecting DNA Ligation Amplification Products," *Clinical Chemistry*, 3799):1522–23 (1991).

Landegren, U., et al., "A Ligase–Mediated Gene Detection Technique," *Science*, 241:1077–80 (1988).

Barany, F., "The Ligase Chain Reaction on a PCR Worls," *PCR Methods and Applications*, 1:5–16 (1991).

Zimmerman, S.B., et al., "Macromolecular Crowding allows Blunt–end Ligation by DNA Ligases from Rat Liver or *Escheric coli*," 80:5852–5856 (1983).

Barany, F., "A Genetic System for Isolation and Characterization of *Taq*I Restriction Endonuclease Mutants," *Gene*, 56:13–27 (1987).

Cotton, R.G.H., "Detection of Single Base Changes in Nucleic Acids," *Biochem J.*, 263:1–10 (1989).

Konrad, E., et al., "Genetic and Enzymic Characterization of a Conditional Lethal Mutant of *Escherichia coli* K12 with a Temperature–Sensitive DNA Ligase," *Chem. Abstracts*, 79(13):75781v, pp. 243–244 (1973).

Hanahan, D. "Studies on Transformation of *Escherichia coli* with Plasmids," *J. Molec. Biol.* 166:557–80 (1983).

Wu, D.Y., et al., "Specificity of the Nick–Closing Activity of Bacteriophage T4 DNA Ligase," *Gene*, 76:245–54 (1989).

Landegren, U., et al. "DNA Diagnostics—Molecular Techniques and Automation," *Science*, 242:229–37 (1988).

Xu, Q.–Y., et al., "Microsequence Analysis of Peptides and Proteins," *Analytical Biochem.*, 170:19–30 (1988).

Moos, M., et al., *J. Biol. Chem.*, "Responsible High Yield Sequencing of Proteins Electrophoretically Separated and Transferred to an Inert Support," 263(13):6005–6008 (1988).

Matsuda, G., et al., "The Primary Structure of L–1 Light Chain of Chicken Fast Skeletal Muscle Myosin and Its Genetic Implication," *FEBS Letters*, 12691):111–113 (1981).

Lathe, R., "Synthetic Oligonucleotide Probes Deduced from Amino Acid Sequence Data Theoritcal and Practical Considerations," *J. Molec. Biol.*, 183:1–12 (1985).

THERMOSTABLE LIGASE MEDIATED DNA AMPLIFICATION SYSTEM FOR THE DETECTION OF GENETIC DISEASES

This is a continuation of application Ser. No. 08/343,785 filed on Nov. 22, 1994, now U.S. Pat. No. 5,494,810 which is a continuation of application Ser. No. 07/971,095 filed on Nov. 2, 1992, now abandoned, which is a continuation in part of application Ser. No. 07/518,447 filed on May 3, 1990, now abandoned.

More than 2,000 conditions have been identified as single-gene defects for which the risk of producing affected offspring can be mathematically predicted. Among these conditions in man include Huntington's chorea, cystic fibrosis, alpha1 antitrypsin deficiency, muscular dystrophy, Hunter's syndrome, Lesch-Nyhan syndrome, Down's syndrome, Tay-Sachs disease, hemophilias, phenylketonuria, thalasemias, and sickle-cell anemia.

Three important techniques have been developed recently for directly detecting these single nucleic acid base pair changes, deletions, insertions, translocations or other mutations. However, two of these techniques cannot be easily automated. In the first such technique, the presence or absence of the mutation in a patient's clinical sample is detected by analysis of a restriction digest of the patient's DNA using Southern blotting [see Journal of Molecular Biology 98:503 (1975)]. However, the Southern blotting technique cannot be used for genetic diseases where the mutation does not alter a restriction site as, for example in alpha1 antitrypsin deficiency. The second technique is by the use of DNA probes which involves the synthesis of an oligonucleotide of about 19 base pairs that is complementary to the normal DNA sequence around the mutation site. The probe is labelled and used to distinguish normal from mutant genes by raising the stringency of hybridization to a level which the probe will hybridize stably to the normal gene, but not to the mutant gene with which it has a single base pair mismatch [see Proc. Natl. Acad. Sci. USA 80:278 (1983)]. The original method has been modified by immobilizing the oligonucleotide and probing with a labelled PCR amplified sample. In this modification, the sample is allowed to hybridize to an immobilized oligonucleotide and then washed off by raising the stringency of hybridization as described above [see Proc. Natl, Acad. Sci. USA 86:6230 (1989)]. Other methods have been developed which use fluorescent PCR primers to specifically amplify only one mutation or allele [see Proc. Natl. Acad. Sci. USA 86:9178 (1989)]. This method requires the separation of products from primers by spin columns or gel electrophoresis and hence is not amenable to large scale automation. The third technique utilizes the presence of both diagnostic and contiguous probes under conditions wherein the diagnostic probe remains substantially covalently bound to the contiguous probe only in the case wherein the sample nucleic acid contains the exact target sequence. In addition, the diagnostic oligonucleotide probe may contain a "hook" (for example, a biotinylated oligonucleotide) which is captured (for example, by streptavidin) as a means of increasing the efficiency of the technique, and the contiguous probe may contain a detectable moiety or label [see Science 241:1077 (1988) and U.S. Pat. No. 4,883,750].

Although it is not always necessary, the detection of single base pair mutations in DNA is usually preceded by techniques to increase or amplify the amount of DNA sample material. A number of techniques exist to perform nucleic acid amplification, among which are: (1) polymerase chain reaction which can amplify DNA a million fold from a single copy in a matter of hours using Taq polymerase and running 20 to 30 reaction cycles on a temperature cycling instrument [see Science 239:487 (1988), and U.S. Pat. No. 4,683,195, 4,683,202, and 4,800,159]; (2) self-sustained sequence replication or 3SR can amplify DNA or RNA 10 million fold from a single copy in less than an hour using reverse transcriptase, T7 RNA polymerase, and RNase H under isothermal conditions at 37° C. [see Proc. Natl. Acad. Sci. USA 87:1874 (1990)]; and (3) Q Beta Replicase can replicate a few thousand RNA molecules containing a special 300bp recognition sequence a billion fold in 30 minutes. Additional techniques are available, and one, the ligase chain reaction, is discussed in the following description of the cloned thermophilic ligase according to the present invention.

In addition to various genetic diseases which may be diagnosed utilizing the present invention, various infectious diseases can be diagnosed by the presence in a clinical sample of a specific DNA sequence characteristic of the causative microorganism. These include bacteria, viruses, and parasites. In such procedures, a relatively small number of pathogenic organisms may be present in a clinical sample from an infected patient and the DNA extracted from these organisms may constitute only a very small fraction of the total DNA in the sample. However, specific amplification of suspected pathogen-specific sequences prior to immobilization and detection by hybridization of the DNA samples should greatly improve the sensitivity and specificity of traditional procedures. In addition, amplification is particularly useful if such an analysis is to be done on a small sample using nonradioactive detection techniques which may be inherently insensitive, or where radioactive techniques are employed, but where rapid detection is desirable.

Although techniques such as these are available, the search for other techniques for determining single base pair mutations continues. The present invention, that is DNA amplification and/or detection by a ligase detection reaction (LDR) or ligase chain reaction (LCR) utilizing the thermophilic DNA ligase from *Thermus aquaticus* to detect a target DNA sequence is part of that continuing effort.

Although other techniques utilizing *E. coli* or T4 DNA ligase for DNA amplification have been attempted, these have been found to be unacceptable because of a high background "noise" levels (after as few as 10 cycles), a condition which does not exist in the ligase chain reaction according to the present invention.

DNA amplification and/or detection has also been attempted utilizing specific ligases. For example, a ligase amplification reaction has been reported [see Gene 76:245 (1989)] that can amplify DNA starting with 500,000 copies in 95 hours, using 75 cycles and replenishing the T4 DNA ligase used after each cycle. However, this reported technique is slow and requires the addition of fresh T4 ligase at each step, both of which requirements make this reported technique unacceptable for automation. The ligase chain reaction according to the present invention allows for amplification of DNA from 200 copies in 3 hours using 30 cycles and does not require the addition of ligase following each cycle.

Throughout the following description of the present invention, terminology specific to the technology field will be used. In order to avoid any misunderstandings as to what is being referenced, and to provide the reader with a clear understanding of what is being described, the following definitions will be used:

"Amplification" refers to the increase in the number of copies of a particular nucleic acid fragment resulting either from an enzymatic chain reaction (such as a polymerase chain reaction, a ligase chain reaction, or a self-sustained sequence replication). or from the replication of the vector into which it has been cloned.

"Blunt end ligation" refers to the covalent linkage of two ends of DNA that are completely flush, i.e. have no cohesive end overhangs.

"Cell", "cell line", and "cell culture" may be used interchangeably and all such designations include progeny. Thus, the words "transformants" or "transformed cells" includes the primary subject cell and cultures derived therefrom without regard for the number of transfers. It is also understood that all progeny may not be precisely identical in DNA content due to deliberate or inadvertent mutations. However, all mutant progeny having the same functionality as screened for in the originally transformed cell are included.

"Clone" refers to a group of genetically identical molecules, cells or organisms asexually descended from a common ancestor. "Cloning" is the process of propagating such identical molecules, cells or organisms. Recombinant DNA techniques make it possible to clone individual genes; this is referred to as "molecular cloning".

"Covalently attaching" refers to forming a covalent chemical bond between two substances. "Cycle" refers to a single melting and cooling of DNA. For example, at very high temperatures such as 94° C., virtually all double stranded DNA (independent of length) unwinds and melts. If one cools the temperature (to 45°–65° C.) in the presence of complementary oligonucleotides, they can hybridize to the correct sequences of the unwound melted DNA. DNA that has been melted and cooled in the presence of complementary oligonucleotides is now a substrate for the DNA ligase reaction.

See "$T_m$".

"Diagnostic portion" refers to that portion of the target sequence which contains the nucleotide change, the presence or absence of which is to be detected. "Contiguous portion" refers to a sequence of DNA which is a continuation of the nucleotide sequence of that portion of the sequence chosen as diagnostic. The continuation can be in either direction It will be recognized, based on the following description, that the precise position of the selected oligonucleotide containing the diagnostic portion is arbitrary, except that it must contain the nucleotide(s) which differentiate the presence or absence of the target sequence at one of its ends. Thus, the oligonucleotide containing the contiguous portion continues the sequence of this arbitrarily chosen oligonucleotide containing the diagnostic portion such that the diagnostic nucleotide(s) is at the junction of the two oligonucleotides.

"Endonuclease" refers to an enzyme (e.g., restriction endonuclease, DNase I) that cuts DNA at sites within the molecule.

"Expression system" refers to DNA sequences containing a desired coding sequence and control sequence in operable linkage in such a manner that hosts transformed with these sequences are capable of producing the encoded proteins. In order to effect transformation, the expression system may be included on a vector, or the transformed vector DNA may also be integrated into the host chromosome.

"Gene" refers to a DNA sequence which encodes a recoverable bioactive polypeptide or precursor. The polypeptide can be encoded by a full-length gene sequence or any portion of the coding sequence so long as the enzymatic activity is retained.

"Gene library" or "library" refers to a collection of randomly-cloned fragments that encompass substantially the entire genome of a given species. This is also referred to as a clone bank or shotgun collection.

"Genome" refers to the entire DNA of an organism.

"Hook" refers to a modification of a probe that enables the user to rapidly and conveniently isolate probes containing this modification by "catching" the hook. The interaction between hook and catching mechanism can be, for example, covalent bonding or ligand/receptor binding of sufficient affinity. Such hooks may include antigens which can be recovered by antibody, biotin which can be recovered by avidin or streptavidin, specific DNA sequences which can be recovered by complementary nucleic acid, or DNA binding proteins (repressors), and specific reactive chemical functionalities which can be recovered by other appropriate reactive groups.

"Hybridization" and "binding" in the context of probes and denatured melted DNA are used interchangeably. Probes which are hybridized or bound to denatured DNA are base paired or "aggregated" to complementary sequences in the polynucleotide. Whether or not a particular probe remains base paired or aggregated with the polynucleotide depends on the degree of complementarity, the length of the probe, and the stringency of the binding conditions. The higher the stringency, the higher must be the degree of complementarity, and/or the longer the probe.

"Klenow fragment" refers to a 76,000 dalton polypeptide obtained by partial proteolytic digestion of DNA polymerase I.

This enzyme possesses the 5'→3' polymerase and 3'→5' exonuclease activities, but not the 5'→3' exonuclease activity of DNA polymerase I.

"Label" refers to a modification to the probe nucleic acid which enables the user to identify the labelled nucleic acid in the presence of unlabelled nucleic acid. Most commonly, this is the replacement of one or more atoms with radioactive isotopes. However, other labels may be substituted for the isotopes as, for example, covalently attached chromophores, fluorescent moieties, enzymes, antigens, groups with specific reactivity, chemiluminescent moieties, and electrochemically detectable moieties.

"Ligase" refers to an enzyme which catalyses the formation of a phosphodiester bond at the site of a single-stranded break in duplex DNA. The ligase enzyme also catalyses the covalent linkage of duplex DNA; blunt end to blunt end, or one cohesive end to another complementary cohesive end.

"Ligase Chain Reaction (LCR)" refers to the amplification of a oligonucleotide ligation product. For example, if oligonucleotides are designed such that the DNA products of one cycle can become the DNA substrates of the next cycle, repeating such cycles will cause an exponential amplification of the DNA (a "chain reaction"). As a thermophilic ligase enzyme is capable of remaining active during many DNA melting and cooling cycles, this allows a DNA amplification to occur rapidly and automatically in a single reaction vessel subject to many thermal cycles in which the oligonucleotide ligation product is amplified.

"Ligase detection reaction (LDR)" refers to the use of two adjacent oligonucleotides for the detection of specific sequences with the aid of a thermophilic ligase with linear product amplification.

"Ligase DNA sequence" refers to the DNA sequence in *Thermus aqauticus* HB8 for the thermophilic ligase of the present invention which comprises, at the amino terminus of the ligase protein, the following nucleic acid sequence (SEQ. ID. No. 1):

| | |
|---|---|
| TCGGAATAGG GGATGCGCCC CTAGTCCAAG GGAAAGTATA GCCCAAGGTA | 50 |
| CACTAGGCC | 60 |
| ATG ACC CTG GAA GAG GCG AGG AAG CCG GTA AAC GAG TTA | 99 |
| CGG GAC CTC ATC CGC TAC CAC AAC TAC CGC TAC TAC GTC | 138 |
| CTG GCG GAC CCG GAG ATC TCC GAC GCC GAG TAC GAC CGG | 177 |
| CTT CTT AGG GAG CTC AAG GAG CTT GAG GAG CGC TTC CCC | 216 |
| GAG CTC AAA AGC CCG GAC TCC CCC ACC CTT CAG GTG GGG | 255 |
| GCG ACG CCT TTC GAG GCC ACC TTC CGC CGC GTC CGC CAC | 294 |
| CGC ACC CGC ATG TAC TCC TTG GAC AAC GCC TTT AAC CTT | 333 |
| GAC GAG CTC AAG GCC TTT GAG GAG CGG ATA GAA CGG GCC | 372 |
| CTG GGG CGG AAG GGC CCC TTC GCC TAC ACC GTG GAG CAC | 411 |
| AAG GTG GAC GGG CTT TCC GTC AAC CTC TAC TAC GAG GAG | 450 |
| GCG GTC CTG GTC TAC CGG GCC ACC GCC GGG GAC GGG GAG | 489 |
| GTG GGG GAG GAG GTC ACC CAG AAC CTC CTC ACC ATC CCC | 528 |
| ACC ATC CCG AGG AGG CTC AAG GGG GTG CCG GAG CGC CTC | 567 |
| GAG GTC CGG GGG GAG GTC TAC ATG CCC ATA GAG GTC TTC | 606 |
| CTC CGG CTC AAC GAG GAG CTG GAG GAG CGG GGG GAG AGG | 645 |
| ATC TTC AAA AAC CCT AGG AAT GCG GCG GCG GGT TCC TTA | 684 |
| AGG CAA AAA GAC CCC CGC ATC ACC GCC AAG CGG GGC CTC | 723 |
| AGG GCC ACC TTC TAC GCC TTA GCG CTT GGG CTG GAG GAG | 762 |
| GTG GAG AGG GAA GCG GTG GCG ACC CAG TTT GCC CTC CTC | 801 |
| CAC TGG CTC AAG GAA AAA GCC TTC CCC GTG GAG CAC GCC | 840 |
| TAC GCC CGG GCC GTG GGG GCG GAA GGG GTG GAG GCG GTC | 879 |
| TAC CAG GAC TGG CTC AAG AAG CGG CGG GCG CTT CCC TTT | 918 |
| GAG GCG GAC GGG GTG GTG GTG AAG CTG GAC GAG CTT GCC | 957 |
| CTT TGG CGG GAG CTC GGC TAC ACC GCC CGC GCC CCC CGG | 996 |
| TTC GCC ATC GCC TAC AAG TTC CCC GCC GAG GAG AAG GAG | 1035 |
| ACC CGG CTT TTG GAC GTG GTC TTC CAG GTG GGG CTG ACC | 1074 |
| GGG CGG GTG ACC CCC GTG GGG ATC CTC GAG CCC GTC TTC | 1113 |
| CTA GAG GGC AGC GAG GTC TCC CGG GTC ACC CTG CAC AAC | 1152 |
| GAG AGC TAC ATA GAG GAG TTG GAC ATC CGC ATC GGG GAC | 1191 |
| TGG GTT TTG GTG CAC AAG GCG GGC GGG GTC ATC CCC GAG | 1230 |
| GTC CTC CGG GTC CTC AAG GAG AGG CGC ACG GGG GAG GAA | 1269 |
| AGG CCC ATT CGC TGG CCC GAG ACC TGC CCC GAG TGC GGC | 1308 |
| CAC CGC CTC CTC AAG GAG GGG AAG GTC CAC CGC TGC CCC | 1347 |
| AAC CCC TTG TGC CCC GCC AAG CGC TTT GAG GCC ATC CGC | 1386 |
| CAC TTC GCC TCC CGC AAG GCC ATG GAC ATC CAG GGC CTG | 1425 |
| GGG GAA AAG CTC ATT GAG AGG CTT TTG GAA AAG GGG CTG | 1464 |
| GTC AAG GAC GTG GCC GAC CTC TAC CGC TTG AGA AAG GAA | 1503 |
| GAC CTG GTG GGC CTG GAG CGC ATG GGG GAG AAG AGC GCC | 1542 |
| CAA AAC CTC CTC CGC GAG ATA GAG GAG AGC AAA AAA AGA | 1581 |
| GGC CTG GAG CGC CTC CTC TAC GGC TTG GGG CTT CCC GGG | 1620 |
| GTG GGG GAG GTC TTG GCC CGG AAC CTG GCG GCC CGC TTC | 1659 |
| GGG AAC ATG GAC CGC CTC CTC GAG GGC AGC CTG GAG GAG | 1698 |
| CTC CTG GAG GTG GAG GAG GTG GGG GAG CTC ACG GGG AGG | 1737 |
| GCC ATC CTG GAG ACC TTG AAG GAC CCC GCC TTC CGC GAC | 1776 |
| CTG GTA CGG AGG CTC AAG GAG GCG GGG GTG GAG ATG GAG | 1815 |
| GCC AAG GAG AAG GGC GGG GAG GCC CTT AAA GGG CTC ACC | 1854 |
| TCC GTG ATC ACC GGG GAG CTT TCC CGC CCC GGG GAA GAG | 1893 |
| GTG AAG GCC CTC CTA AGG CGC CTC GGG GCC AAG GTG ACG | 1932 |
| GAC TCC GTG AGC CGG AAG ACG AGC TAC CTC GTG GTG GGG | 1971 |
| GAG AAC CCG GGG GAG AAC CCG GGG AGC AAG CTG GAG AAG | 2010 |
| GCC AGG GCC CTC GGG GTC CCC ACC CTC ACG GAG GAG GAG | 2049 |
| CTC TAC CGG CTC CTG GAG GCG CGG ACG GGG AAG AAG GCG | 2088 |
| GAG GAG CTC GTC TAA AGGCTTCC | 2111 |

The corresponding amino acids (SEQ. ID. No. 2) are:

```
Met Thr Leu Glu Glu Ala Arg Lys Arg Val Asn Glu Leu Arg Asp
              5                  10                 15

Leu Ile Arg Tyr His Asn Tyr Arg Tyr Tyr Val Leu Ala Asp Pro
             20                  25                 30

Glu Ile Ser Asp Ala Glu Tyr Asp Arg Leu Leu Arg Glu Leu Lys
             35                  40                 45

Glu Leu Glu Glu Arg Phe Pro Glu Leu Lys Ser Pro Asp Ser Pro
             50                  55                 60

Thr Leu Gln Val Gly Ala Arg Pro Leu Glu Ala Thr Phe Arg Pro
             65                  70                 75

Val Arg His Pro Thr Arg Met Tyr Ser Leu Asp Asn Ala Phe Asn
             80                  85                 90

Leu Asp Glu Leu Lys Ala Phe Glu Glu Arg Ile Glu Arg Ala Leu
             95                 100                105
```

-continued

```
Gly Arg Lys Gly Pro Phe Ala Tyr Thr Val Glu His Lys Val Asp
            110                 115                120

Gly Leu Ser Val Asn Leu Tyr Tyr Glu Glu Gly Val Leu Val Tyr
            125                 130                135

Gly Ala Thr Arg Gly Glu Gly Glu Val Gly Glu Glu Val Thr Gln
            140                 145                150

Asn Leu Leu Thr Ile Pro Thr Ile Pro Arg Arg Leu Lys Gly Val
            155                 160                165

Pro Glu Arg Leu Glu Val Arg Gly Glu Val Tyr Met Pro Ile Glu
            170                 175                180

Ala Phe Leu Arg Leu Asn Glu Glu Leu Glu Glu Arg Gly Glu Arg
            185                 190                195

Ile Phe Lys Asn Pro Arg Asn Ala Ala Ala Gly Ser Leu Arg Gln
            200                 205                210
```

-continued

Lys Asp Pro Arg Ile Thr Ala Lys Arg Gly Leu Arg Ala Thr Phe
          215                 220                 225

Tyr Ala Leu Gly Leu Gly Leu Glu Glu Val Glu Arg Glu Gly Val
              230                 235                 240

Ala Thr Gln Phe Ala Leu Leu His Trp Leu Lys Glu Lys Gly Phe
              245                 250                 255

Pro Val Glu His Gly Tyr Ala Arg Ala Val Gly Ala Glu Gly Val
              260                 265                 270

Glu Ala Val Tyr Gln Asp Trp Leu Lys Lys Arg Arg Ala Leu Pro
              275                 280                 285

Phe Glu Ala Asp Gly Val Val Lys Leu Asp Glu Leu Ala Leu
              290                 295                 300

Try Arg Glu Leu Gly Tyr Thr Ala Arg Ala Pro Arg Phe Ala Ile
              305                 310                 315

Ala Tyr Lys Phe Pro Ala Glu Glu Lys Glu Thr Arg Leu Leu Asp
              320                 325                 330

Val Val Phe Gln Val Gly Arg Thr Gly Arg Val Thr Pro Val Gly
              335                 340                 345

Ile Leu Glu Pro Val Phe Leu Glu Gly Ser Glu Val Ser Arg Val
              350                 355                 360

Thr Leu His Asn Glu Ser Tyr Ile Glu Glu Leu Asp Ile Arg Ile
              365                 370                 375

Gly Asp Trp Val Leu Val His Lys Ala Gly Gly Val Ile Pro Glu
              380                 385                 390

Val Leu Arg Val Leu Lys Glu Arg Arg Thr Gly Glu Glu Arg Pro
              395                 400                 405

Ile Arg Trp Pro Glu Thr Cys Pro Glu Cys Gly His Arg Leu Leu
              410                 415                 420

Lys Glu Gly Lys Val His Arg Cys Pro Asn Pro Leu Cys Pro Ala
              425                 430                 435

Lys Arg Phe Glu Ala Ile Arg His Phe Ala Ser Arg Lys Ala Met
              440                 445                 450

Asp Ile Gln Gly Leu Gly Glu Lys Leu Ile Glu Arg Leu Leu Glu
              455                 460                 465

Lys Gly Leu Val Lys Asp Val Ala Asp Leu Tyr Arg Leu Arg Lys
              470                 475                 480

Glu Asp Leu Val Gly Leu Glu Arg Met Gly Glu Lys Ser Ala Gln
              485                 490                 495

Asn Leu Leu Arg Gln Ile Glu Glu Ser Lys Lys Arg Gly Leu Glu
              500                 505                 510

Arg Leu Leu Tyr Ala Leu Gly Leu Pro Gly Val Gly Glu Val Leu
              515                 520                 525

Ala Arg Asn Leu Ala Ala Arg Phe Gly Asn Met Asp Arg Leu Leu
              530                 535                 540

Glu Ala Ser Leu Glu Glu Leu Leu Glu Val Glu Glu Val Gly Glu
              545                 550                 555

Leu Thr Ala Arg Ala Ile Leu Glu Thr Leu Lys Asp Pro Ala Phe
              560                 565                 570

Arg Asp Leu Val Arg Arg Leu Lys Glu Ala Gly Val Glu Met Glu
              575                 580                 585

Ala Lys Glu Lys Gly Gly Glu Ala Leu Lys Gly Leu Thr Phe Val
              590                 595                 600

Ile Thr Gly Glu Leu Ser Arg Pro Arg Glu Glu Val Lys Ala Leu
              605                 610                 615

Leu Arg Arg Leu Gly Ala Lys Val Thr Asp Ser Val Ser Arg Lys
              620                 625                 630

Thr Ser Tyr Leu Val Val Gly Glu Asn Pro Gly Ser Lys Leu Glu
              635                 640                 645

Lys Ala Arg Ala Leu Gly Val Pro Thr Leu Thr Glu Glu Glu Leu
              650                 655                 660

Tyr Arg Leu Leu Glu Ala Arg Thr Gly Lys Lys Ala Glu Glu Leu
              665                 670                 675

Val

"Ligating" refers to covalently attaching polynucleotide sequences together to form a single sequence. This is typically performed by treatment with a ligase which catalyzes the formation of a phosphodiester bond between the 5' end of one sequence and the 3' end of the other. However, in the context of the invention, the term "ligating" is also intended to encompass other methods of covalently attaching such sequences, e.g., by chemical means. The terms "covalently attaching" and "ligating" may be used interchangeably.

"Nick closing activity" refers to covalent linkage of adjacent strands of DNA. It may be used to assay for ligase activity by virtue of converting open circular DNA (OCDNA) to covalently closed circular DNA (CCCDNA) and determining the speed at which the specimen DNA migrates on an ethidium bromide stained agarose gel (OCDNA migrates slower than CCCDNA).

"Oligonucleotide" refers to a molecule comprised of two or more deoxyribonucleotides or ribonucleotides, preferably more than three. Its exact size will depend on the ultimate function or use of the oligonucleotide. The oligonucleotide may be derived synthetically or by cloning.

"Operably linked" refers to juxtaposition such that the normal function of the components can be performed. Thus, a coding sequence "operably linked" to control sequences refers to a configuration wherein the coding sequences can be expressed under the control of the control sequences.

"Overproducer strain" refers to a strain of bacteria or other host cell that may be induced to overproduce a particular enzyme or chemical substance.

"Polymerase" refers to enzymes which catalyze the assembly of deoxyribonucleotides into DNA.

"Polymerase chain reaction (PCR)" refers to a patented process (described in U.S. Pat. Nos. 4,683,202 and 4,683,195) for the exponential amplification of a specific DNA fragment by utilizing two oligonucleotide primers that hybridize to opposite strands and flank the region of interest in a target DNA. The process consists of a repetitive series of cycles involving template denaturation, primer annealing, and the extension of the annealed primers by Taq DNA polymerase.

"Probe" refers to an oligonucleotide designed to be sufficiently complementary to a sequence in a denatured nucleic acid to be probed (in relation to its length) to be bound under selected stringency conditions. "Contiguous probe" describes a probe which is complementary to the contiguous portion. "Diagnostic probe" describes a probe which is complementary to the diagnostic portion. "Target probe" describes a probe which is complementary to the target sequence and is made by covalently attaching (ligating) the diagnostic probe and the contiguous probe.

"Reporter group" refers to a group that signifies the presence of a particular moiety (see "label"). "Restriction endonucleases" refers to those enzymes which cut DNA by recognizing specific sequences internal to the molecule and subsequently cutting the DNA in both strands at sites either within or outside of the recognition sequence. "Sticky end ligation" refers to the covalent linkage of two ends of DNA that contain complementary 5' or 3' single strand overhangs which are usually, but not limited to, one to five nucleotides in length.

"Stringency" refers to the combination of conditions to which nucleic acids are subject that cause the double stranded DNA to dissociate into component single strands; among these are pH extremes, high temperature, and salt concentration. "High stringency" refers to the conditions, specifically hybridization and washing, which are sufficient to allow for the detection of unique sequences using an oligonucleotide probe or closely related sequence under standard Southern hybridization protocols [as described in J. Mol. Biol. 98:503 (1975)].

"$T_m$" refers to the temperature at which two complementary strands of DNA unwind and separate. This is a function of the single stranded DNA length and its base composition - for small fragments, an approximate value of $T_m$ in °C. is equal to $4(G+C)+2(A+T)$. For example, an oligonucleotide which has 5G, 7C, 5A, and 4T bases has a temperature of $4(5+7)+2(5+4)$ or 66° C.

"Target sequence" refers to a nucleic acid sequence, the presence or absence of which is desired to be detected. In the context of a preferred application of the method according to the present invention, it is a sequence which forms part of a coding region in a gene associated with a genetic disease, such as sickle-cell anemia. In many such diseases, the presence of the genetic aberration is characterized by small changes in the coding sequence; most frequently, normal individuals have sequences which differ by one nucleotide from the corresponding sequences present in individuals with the genetic "deficiency." In the method according to the present invention, either the normal or altered sequence can be used as the target sequence.

"Thermophilic enzyme" refers to an enzyme which functions at high temperatures of 50° to 90° C.; some may survive brief exposure to temperatures of 94° to 100° C. at which normal enzymes denature and thus become inactive.

"Thermostable ligase" refers to an enzyme which is stable to heat, is heat resistant, and catalyzes (facilitates) ligation, at high temperatures of 50° to 900° C., of adjacent oligonucleotides in the proper manner to form a product which is complementary to the target nucleic acid strand. Generally, the enzyme activates the 5' end of one oligonucleotide and links this to the 3' strand of an adjacent DNA molecules. There may, however, be thermostable enzymes which use other mechanisms to covalently attach adjacent oligonucleotides. Thermostable ligase can, under the proper conditions, covalently link a number of different nucleic acid substrates at high temperatures of 50° to 90° C., such as closing "nicks" in DNA, and sticky end and blunt end ligations.

The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded nucleic acids. By "irreversible denaturation" as used in this connection, is meant a process bringing about a permanent and complete loss of enzymatic activity. The heating conditions necessary for denaturation will depend, e.g., on the buffer salt concentration and the length and nucleotide composition of the nucleic acids being denatured, but typically range from about 85° C, for shorter oligonucleotides, to about 105° C. for a time depending mainly on the temperature and the nucleic acid length, typically from about 0.25 minutes for shorter oligonucleotides, to 4.0 minutes for longer pieces of DNA. Higher temperatures may be tolerated as the buffer salt concentration and/or GC composition of the nucleic acid is increased. Preferably, the enzyme will not become irreversibly denatured at about 90° to 100° C. The thermostable enzyme according to the present invention has an optimum temperature at which it functions that is greater than about 45° C., probably between 50° and 90° C., and optimally between 60° and 80° C.

A more thorough and complete understanding of the cloning of the thermophilic ligase sequence and the use of this enzyme in the thermophilic ligase mediated DNA amplification procedure for the detection of single base pair sequence differences in genetic diseases can be obtained by reference to the following figures and examples which are presented by way of illustration only and are not intended, nor should they be considered, to limit the scope of the claimed invention.

With specific reference to the figures.

Figure 7:
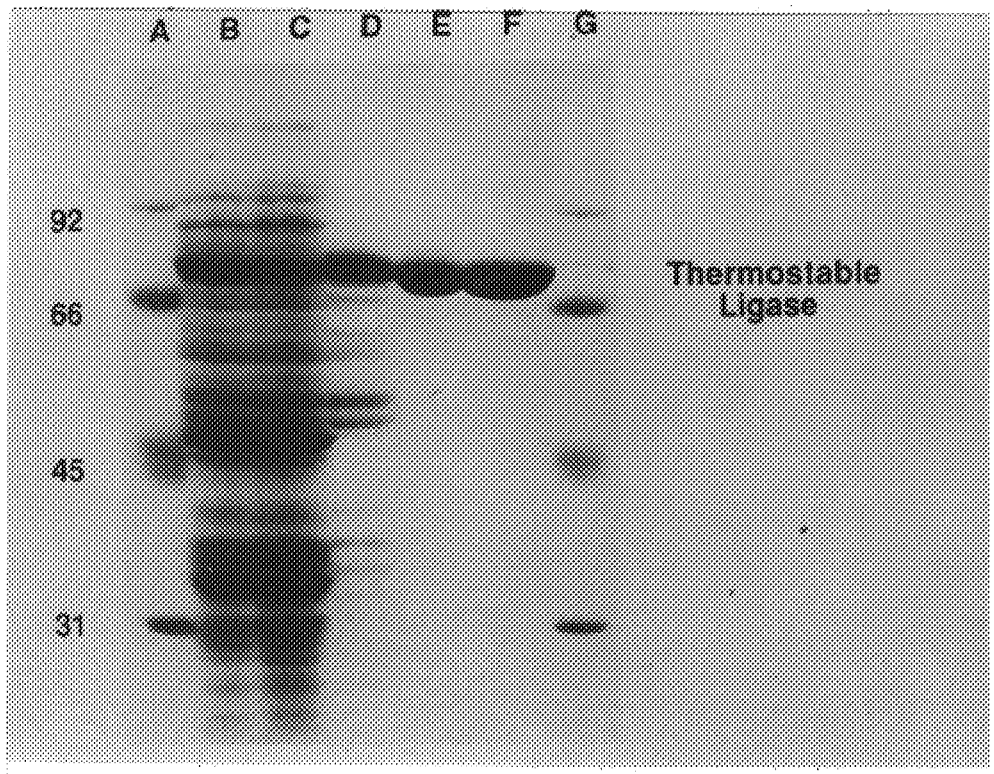
FIG. 7 is a photographic representation of SDS-10% polyacrylamide gel electrophoresis of the thermostable ligase, according to the present invention, at different stages of purification.
Figure 8:
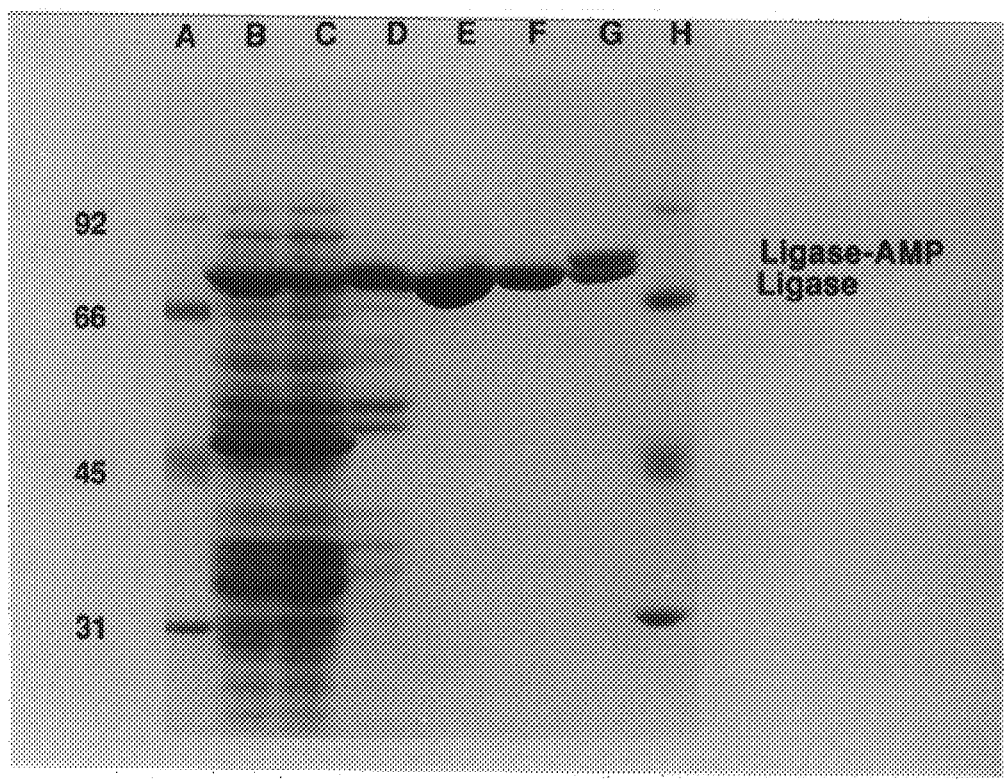
FIG. 8 is a second photographic representation of SDS-10% polyacrylamide gel electrophoresis of the thermostable ligase, according to the present invention, at different stages of purification.

In FIG. 7, lanes A and G represent marker proteins (molecular weights are given in kd); B represents whole cells after induction; C represents crude supernatant after sonication; D represents pooled DEAE flow-through after heat treatment; and E and F represent fractions 23 and 24 after phosphocellulose chromatography. In FIG. 8, lanes A and H represent marker proteins (molecular weights are given in kd); B represents whole cells after induction; C represents crude supernatant after sonication; D represents pooled DEAE flow-through after heat treatment; E represents fraction 23 after phosphocellulose chromatography; F represent fraction 23 incubated with nicked DNA in ligase buffer in the absence of NAD; and G represents fraction 23 incubated with NAD in ligase buffer in the absence of nicked DNA. In FIG. 8, the higher molecular weight ligase (approximately 81 kd) is the adenylated form, while lower molecular weight ligase (approximately 78 kd) is non-adenylated.

Figure 1:
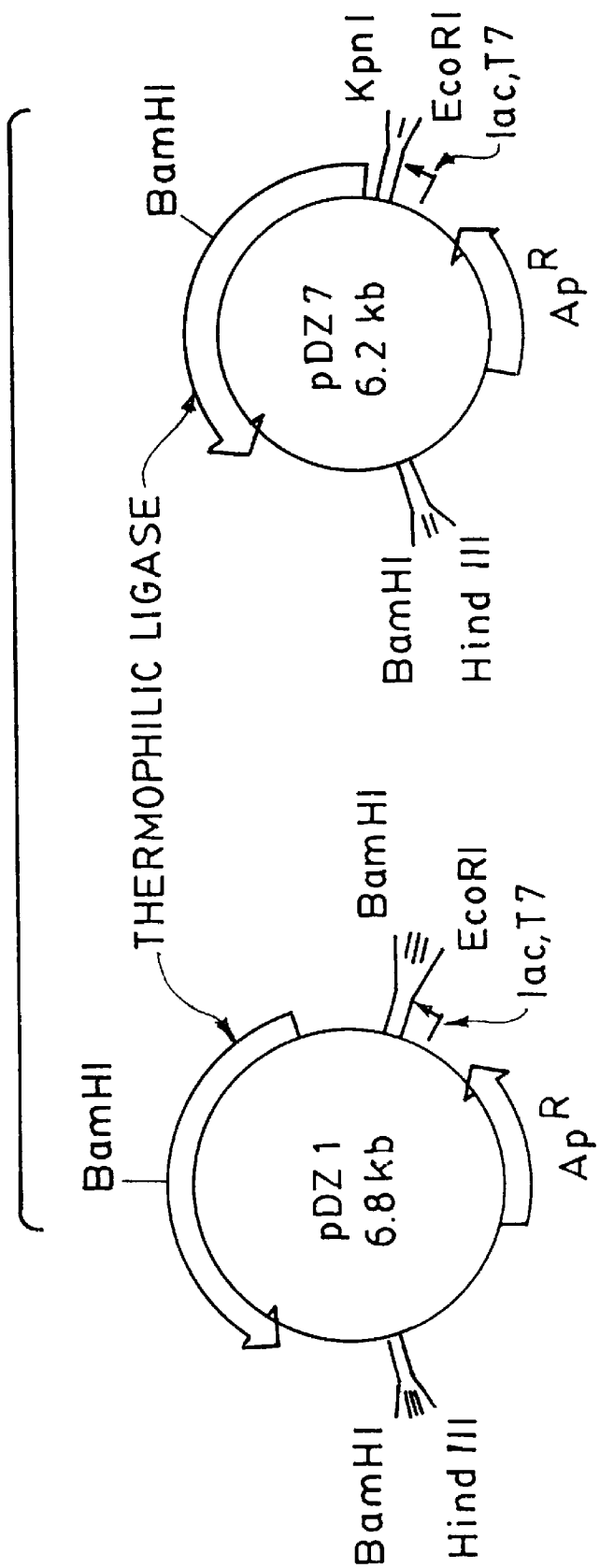
FIG. 1 is a depiction of plasmids pDZ1 and pDZ7.

The plasmids depicted in FIG. 1 have been deposited with, and accepted by, a collection agency under the Budapest Treaty deposit rules. Plasmid pDZ1 has been incorporated within a host bacteria (*E. coli* strain AK53), deposited with the American Type Culture Collection, and granted the collection number ATCC No. 68307. Plasmid pDZ7 has been incorporated within a host bacteria (*E. coli* strain AK53), deposited with the American Type Culture Collection, and granted the collection number ATCC No. 68308.

While other methods may be used, in general, the production of the thermophilic ligase according to the present invention will be by recombinant means which typically involve the following:

First, a DNA is obtained which encodes the mature (as used herein the term includes all muteins) enzyme or a fusion of the thermophilic ligase to an additional sequence that does not destroy its activity or to an additional sequence cleavable under controlled conditions to give an active protein. If the sequence is uninterrupted by introns, it is suitable for expression in any host. However, the sequence should be in an excisable and recoverable form. Using PCR technology, for example, most DNA sequences coding for enzymes may be amplified and hence recovered in an "excised" form.

The excised or recovered coding sequence is then placed in operable linkage with suitable control sequences in a replicable expression vector which is used to transform a suitable host. The transformed host is then cultured under suitable conditions to effect the production of the recombinant thermophilic ligase, and the ligase isolated and purified by known means.

Each of the above procedures may be accomplished in a variety of ways, For example, the desired coding sequences may be obtained from genomic fragments and used directly in appropriate hosts; the constructions for expression vectors operable in a variety of hosts are made using appropriate replicons and control sequences; and suitable restriction sites may, if not normally available, be added to the ends of the coding sequence so as to provide an excisable gene to insert into the appropriate vector.

The control sequences, expression vectors, and transformation methods are dependent on the type of host cell used to express the gene. Generally, bacterial hosts are the most efficient and convenient for the production of recombinant proteins and therefore preferred for the expression of the thermophilic ligase according to the present invention. However, other hosts such as yeast, plant, and insect or mammalian cells may also be used if convenient. For the purposes of the present invention, one source of the host cell is considered to be equivalent to any other available and suitable host cell source.

EXAMPLE I (growth of *T. aquaticus* strain HB8 and isolation of DNA)

DNA was isolated from *Thermus thermophilus* strain HB8 (ATCC No. 27634). This strain has recently been reclassified as *Thermus aqauticus* strain HB8 [see Arch. Microbiol 117:189 (1978)].

Cells were grown overnight at 75° C. in a water bath shaker in TAB broth [see Nuc. Acids Res., pgs 6795–6804 (1981)] (which contains per liter, 5 g Bacto™-tryptone, 3 g yeast extract, 2 g NaCl, and 1 g dextrose) adjusted to pH 7.2–7.5 with NaOH, and harvested by centrifugation to yield 3.1 g wet weight from 800 ml of media. Cells were resuspended in 15 ml of 50 mM Tris pH 8.0 buffer containing 50 mM EDTA and 15 mg egg white lysozyme. The resuspended cells were lysed by the addition of 2 ml of 10% (weight/volume) sodium dodecyl sulfate followed by incubation at 37° C. for 15 minutes and two repeated cycles of freezing at −50° C. and thawing at 37° C. The aqueous solution was extracted sequentially with equal volumes of aqueous phenol (preequilibrated to pH 7.5 with sodium borate), followed by phenol/chloroform, and finally chloroform.

Nucleic acids were precipitated by mixing with 2 volumes of 95% ethanol, chilling to −50°0 C. for 15 min., and pelleted by centrifugation. After removal of the supernatant and drying the pellet, nucleic acids were resuspended in 1 ml TE buffer (10 mM Tris HCl, pH 8.0, containing 1 mM EDTA). RNA was digested by the addition of 100 μg RNase A to each ml of suspension, and the mixture incubated at 37° C. for 1 hr. DNA was precipitated by adding 1/10th vol. of 3 M sodium acetate and 3 vol. of 100% ethanol, chilled to −50° C. for 15 min., pelleted by centrifugation, washed with 70% ethanol, and finally resuspended in TE buffer at a final concentration of 2 mg/ml.

Although DNA utilized in the example given above was isolated from *Thermus aquaticus*, the resultant thermophilic ligase having the necessary properties according to the present invention may have as its initial source DNA isolated from other Thermus species or other thermophilic bacteria, phages, or viruses.

DNA isolated from *T. aquaticus* strain HB8 cannot be cleaved by the restriction endonucleases Taq I (whose recognition sequence is TCGA) or EcoRI (whose recognition sequence is GAATTC). The inability to cleave certain sequences is a consequence of protective methylation [see H. O. Smith and S. V. Kelly, DNA Methylation: Biochemistry and Biological Significance, eds. Razin, Cedar and Riggs, p 39–71, Springer-Verlag Inc., New York (1987)] at the N6 position of adenine residues. Previous investigators [see J. Bact. 169:3243 (1987)] have shown that there is a gene, termed mrr, which restricts adenine methylated DNA of the form G-6MeANTC and CTGC-6MeAG. In the cloning of the Taq I restriction endonuclease and methylase, several *E. coli* strains were found to restrict the TCGA methylated DNA, an affect originally (but incorrectly) attributed to the mrr gene [see Gene 56:13 (1987) and Nuc. Acid Res. 15:9781 (1987)]. Recent work conducted at the Cornell University Medical College has shown the presence of an additional gene, besides mrr which encodes a protein that restricts TCGA methylated DNA. Briefly, strains containing a Tn5 ($Km^R$) transposon disrupting the mrr gene were [see J. Bact. 169:3243 (1987)] used for transduction [according to J. H. Miller in Experiments in Molecular Genetics, Cold Spring Harbor Laboratory, pp 201–205 (1972)] of the $Km^R$ marker into several strains of *Escherichia coli* that resulted in strain converts to a mrr − (defective mrr protein) genotype. None of these transduced strains could tolerate the Taq methylase gene, indicating there is a second gene responsible for the restriction of TCGA methylated DNA. Thus, one of the first necessary requirements (which prior to the present invention had not been apparent) for the making of the present invention was the selection of an *E. coli* strain which would not heavily restrict TCGA methylated DNA.

In the present invention, a derivative of the RRI strain of *E. coli* which could tolerate the Taq methylase gene and which contained a Tn10 ($Tc^R$) transposon was transduced to a ligts7 strain [N3098, see Wilson and Murray, J. Mol. Biol. (1979) and J. Mol. Biol. 77:531 (1973)] to create *E. coli* strain AK76. This strain has been deposited in the American Type Culture Collection, and has been granted the collection number ATCC No. 55032. This strain contains a temperature sensitive ligase gene, such that at 42° C. the strain cannot grow. This strain can tolerate the Taq methylase gene, and other methylated DNA, especially the DNA isolated from *T. aquaticus*. Since it also has a temperature sensitive ligase gene, it could be used as a host for the cloning of a functional *T. aquaticus* ligase gene by selecting for growth at 42° C.

Cloning of the *T. aquaticus* ligase gene was based on a positive selection scheme similar to that described by Wilson and Murray. The approach was to construct libraries of *T. aquaticus* DNA inserted into a suitable vector. These libraries were then introduced via transformation into a ligts7 *E. coli* strain that did not restrict methylated *T. aquaticus* DNA, such as strain AK76. These cells were then grown at the nonpermissive temperature, that is at 42° C. Any survivors could be (i) revertants to a lig+ phenotype; (ii) second site revertants that increase expression of the defective *E. coli* ligase gene product; (iii) a cloned piece of *T. aquaticus* DNA that increases expression of the defective *E. coli* ligase gene product; or (iv) a cloned piece of *T. aquaticus* DNA that contains the *T. aquaticus* ligase gene.

For the desired last alternative to work, it is necessary that (i) the entire ligase gene is cloned; (ii) that either the endogenous control sequences for *T. aquaticus* ligase expression function in *E. coli*, or that exogenous vector control sequences are sufficiently close to the amino terminus and the ligase gene is cloned in the correct orientation to allow for proper expression in *E. coli*; (iii) the *T. aquaticus* ribosome binding site works in *E. coli*; and (iv) the *T. aquaticus* ligase is active enough at 42° C., and the amount synthesized is sufficient to complement ligase function in *E. coli* without interfering with other processes.

Construction of the suitable libraries used in the present invention utilized conventional vectors containing desired control sequences, and standard restriction endonuclease and ligation techniques. Purified plasmid DNA, *T. aquaticus* DNA sequences, or synthesized oligonucleotides for use in the present invention, were cleaved, tailored, and religated in the form desired also by conventional techniques.

The selection of a suitable vector for use in the present invention is more than a mere matter of selecting a vector among the many which exist and have been used in the past. High copy number derivatives of pUC plasmids [see for example, C. Yanisch-Peron et al., Gene 33:103 (1985), or J. Vieira et al., Gene 19:259 (1982)] are actually somewhat unstable when grown at 42° C. Low copy plasmids such as pBR322 derivatives pFBI 1, 2, 13, 14 and 15 [see F. Barany, Proc. Natl. Acad. Sci. USA 82:4202 (1985)] may not produce enough enzyme to complement the ligase defect. In making the present invention, 18 different libraries using 3 different sets of vectors were constructed. The successful clone was derived from the vector pTZ18R [see D. A. Mead et al., Protein Engineering 1:67 (1986)], although other vectors may also be utilizable.

Generally, site-specific DNA cleavage, as more particularly described in the following example, is performed by treating the DNA with a suitable restriction enzyme under conditions which are generally understood in the art, and the particulars of which are specified by the manufacturers of these commercially available restrictions enzymes. In general, about 1 µg of plasmid or DNA sequence is cleaved by two to ten units of enzyme in about 20 µl of buffer solution. Incubation times of about one to two hours at about 37° C. are preferable, although variations in both the time and temperature can be tolerated. After each incubation, protein is removed by extraction with phenol/chloroform, and may be followed by a further extraction. The nucleic acids are recovered by precipitation with ethanol. If desired, size separations of the cleaved fragments may be performed by polyacrylamide or agarose gel electrophoresis using standard techniques.

EXAMPLE II (Site Specific Cleavage)

Site-specific cleavage of both plasmid and *T. aquaticus* DNA was performed using commercially available restriction endonucleases in standard buffers.

In general, about 10 µg or plasmid or *T. aquaticus* DNA was cleaved in 100 µl of buffer solution by the addition of 20 to 100 units of the appropriate restriction endonuclease, and incubating the mixture at 37° C. for 1 to 2 hrs.

After each incubation, protein was removed by sequential extractions with phenol (2x), n-butanol (2x), and the nucleic acid was recovered by precipitation with ethanol.

Construction of suitable vectors containing the desired coding and control sequences employs conventional ligation and restriction techniques. Briefly, isolated plasmids, DNA sequences, or synthesized oligonucleotides are cleaved, tailored, and religated in the form desired.

The restriction endonucleases utilized for cleavage of the specific libraries used in accordance with the procedure outlined in Example II were BamHI, Sacl, Kpnl, (Asp718), PstI, HindIII, and Smal, however, other endonucleases or partial digests with SaullIA, for example, could have been used. Due to adenosine methylation, the commonly utilized restriction endonucleases EcoRI, SalI or XhoI were not used since DNA from *T. aquaticus* strain HB8 could not be cleaved by these enzymes.

Restriction fragments resulting from the procedure outlined in Example II containing 5' overhangs may be blunt ended by filling in with DNA polymerase I large (Klenow fragment) in the presence of the four deoxynucleotide triphosphates using incubation times of about 15 to 30 minutes at 37° C. in 50 mM Tris pH 7.6 buffer containing 50 mM NaCl, 10 mM $MgCl_2$, 10 mM DTT, and 50–100 µM deoxynucleotide triphosphates. The Klenow fragment will fill in at 5' sticky ends. If 3' overhangs are generated, they may be chewed back with mung bean nuclease. After treatment with Klenow, the mixture is extracted with phenol/chloroform and precipitated with ethanol. Subsequent treatment under appropriate conditions with S1 nuclease results in hydrolysis of any single stranded portion. These conventional procedures may be used for cloning any fragment into a (blunt end) site within the vector.

EXAMPLE III (Vector Construction)

In vector constructions, the linearized vector is commonly treated with a phosphatase enzyme (or alternatively with a second nearby restriction endonuclease) to prevent recircularization of the vector in the absence of insert DNA. For example, a sample of BamHI (5' overhang) or SacI (3' overhang) DNA (9 µg) in 150 µl 50 mM Tris HCl buffer at pH 8.0 and containing 10 mM MgCl2 and 6 mM mercaptoethanol in the presence of $Na^+$may be treated with Calf Intestine Alkaline Phosphatase (CIAP, 22 units) at 37° C. for 15 min., followed by incubation at 50° C. for 30 min. to remove phosphate groups from either 5' or 3' overhangs. Alternatively, Bacterial Alkaline Phosphatase (BAP, 10 units) may be used in 150 µl 10 ml Tris HCI in the presence of $Na^+$and $Mg^{++}$and incubating at 60° C. for about 1 hr. CIAP may be subsequently denatured by the addition of EDTA and EGTA to chelate divalent cations, and heating to 65° C. for 15 min. Either CIAP or BAP protein is them removed by sequential extractions with phenol (2x), n-butanol (2x), and nucleic acid recovered by precipitation with ethanol.

The effectiveness of the phosphatase step is assayed by comparison of the number of transformants generated when vector is religated in the absence or presence of insert DNA. Typical results of from 10 to 100 fold more transformations when insert DNA is present is indicative that the vector DNA has been properly phosphatased.

EXAMPLE IV (Ligations)

Ligations were performed in 30–100 μl volumes using 1–2 μg linearized and phosphatased vector made as previously described. 2–4 μg T. aquaticus DNA cut with a restriction endonuclease generating the same ends as the vector, in 50 mM Tris HCl buffer at pH 8.0 and containing 10 mM $MgCl_2$, 1 mM EDTA, 1 mM ATP, 6 mM mercaptoethanol and from 3 to 7 (Weiss) units of T4 ligase, by incubating at either 4 or 15° C. overnight. After ligation, EDTA was added, the T4 ligase inactivated by heating the solution to 65° C. for 15 min., and nucleic acids recovered by ethanol precipitation.

Ligation mixtures were introduced into a suitable host such as E. coli strains RR1, AK53 or AK76—the last one suitable for immediate positive selection of the lig+ phenotype—via conventional transformation procedures [see Hanahan, J. Mol. Biol. 166:3243 (1987)]. Transformants were selected by plating on ampicillin (or other drugs such as tetracycline or kanamycin depending upon the plasmid used) containing plates. For positive selection of the lig+ phenotype, AK76 transformants were plated onto SOB plates (made by autoclaving 20 g Bacto™-tryptone, 5 g Bacto™-yeast extract, 0.5 g NaCl, 16 g Bacto™-agar in 1 liter of distilled water adjusted to pH 7.5 with NaOH prior to autoclaving, then adding 20 ml 1 M $MgSO_4$) containing 0.2% maltose, 0.2 mg/ml IPTG (to induce the lac promoter), and 50 μg/ml ampicillin (to select the plasmid-containing cells), and grown overnight at 420C to 42.50° C.

Libraries ranged in size from about 5,000 to 27,000 clones. Given the general estimate that the bacterial chromosome contains about 2,000 to 4,000 kilobases, and the average insert consisted of 5 to 10 kb, it was apparent that several libraries contained redundant clones.

Mixed plasmid preparations were made from six libraries using conventional techniques [see Methods Enzymol. 100:243 (1983)], and introduced into fresh AK76 cells. Transformants from each library were plated on 6 SOB plates (each plate receiving between 30,000 and 70,000 clones) and incubated at 42° C. One library produced from 11 to 19 exceedingly small colonies per plate; the remaining libraries produced an occasional large colony.

Individual clones were picked, plasmid DNA prepared using conventional techniques [see Anal. Biochem. 114:193 (1981)], and analyzed by restriction digestion. All 12 small clones produced a 6.8 kb plasmid containing two BamHI fragments (1.8 and 2.1 kb respectively) cloned within the BamHl site of pTZ18R. One such plasmid has been designated pDZ1 as depicted in FIG. 1. By calculating back to the original library, (of 5,200 clones), it appears that all pDZ1 plasmids derived from a single clone. The large colonies contained plasmids close to the size of the original vector. Therefore, these large colonies are probably revertants of the chromosomal ligts7 gene which contained any plasmid solely to confer resistance to ampicillin.

Retransforming plasmid pDZ1 into AK76 cells, and selecting at 42° C. on SOB plates containing maltose, IPTG, and ampicillin as described in Example IV, again yielded small colonies. Plating fresh transformants on tryptone yeast agar containing ampicillin did not produce colonies. This result suggests that induction of the lac promoter during plasmid establishment is necessary for production of sufficient quantities of T. aquaticus ligase to complement the genetic defect. Once the plasmid has become established in AK76 cells, such clones will give exceedingly small colonies when streaked and allowed to grow on tryptone yeast plates containing ampicillin at 42° C.

Digestion of pDZ1 with BamHI, followed by religation would scramble the fragments. Transformation of such a ligation mix into AK76, followed by plating at 37° C., i.e. under non-selective conditions, compared to plating at 42° C., i.e. under selective conditions, yielded 1,000 fold more colonies under non-selective conditions. The starting pDZ1 plasmid yielded only 2 fold more colonies under non-selective than selective conditions. This finding strongly suggests that the presence of both fragments, and the orientation they are cloned, is necessary for proper expression of T. aquaticus ligase.

Although pDZ1 contains several SacI and SmaI sites, it only 25 contains a single (vector derived) PstI, KpnI, or HindIII site. Thus, it would have been expected that a number of ligase clones would have been isolated from the PstI, KpnI, or HindIII digest libraries. However, the only ligase clone was derived from the partial BamHI digest library. Although it is not clear why this happened, one conceivable explanation is that other clones did not bring the lac promoter controlling element sufficiently close to the start of the ligase gene to adequately express the ligase protein during plasmid establishment.

The cloning of T. aquaticus ligase as described above will now enable those skilled in the art to clone any thermophilic or thermostable ligase, whether of procaryotic, archebacterial, eukaryotic or phage origin by additional approaches. Accordingly the cloning of such ligases are within the scope of the present invention.

Such additional approaches to cloning may include, for example, (i) cloning T. aquaticus DNA into a red⁻lambda vector and screening for the ability of recombinant phage lambda to form plaques at 39° C. on a ligs7 strain such a AK76 [essentially as generally described in J. Mol. Biol. 132:471 (1979)]; (ii) use of the lambda gt11 phage to express portions of the ligase gene, and subsequently screening with antibodies raised to purified T. aquaticus ligase—the positive lambda gt 11 clone may then be used to identify the full length gene by hybridization to other plasmid or phage libraries, essentially as described in the cloning of T. aquaticus polymerase [see J. Biol. Chem 264:6427 (1989)]; 90(iii) based upon the ligase DNA sequence, probes can be made that would hybridize to and therefore help to identify and retrieve other thermostable ligase encoding sequences in a variety of species. Accordingly, portions of the DNA encoding at least five amino acids from T. aquaticus ligase can be replicated, or amplified using PCR techniques, and the denatured or single stranded forms may be used as probes to retrieve additional DNAs encoding a thermophilic or thermostable ligase. Alternatively, oligodeoxyribonucleotide probes can be synthesized which encode at least five amino acids, and these may be used to retrieve additional DNAs encoding a thermophilic or thermostable ligase.

The selection of a portion of DNA encoding for at least five amino acids is based upon the portion containing fifteen nucleic acid bases which is more than the statistical minimum length that an oligonucleotide should have in order to find a single complementary sequence in a genome. However, portions slightly smaller (the minimum number in E. coli is, for example 12, indicating a portion as small as that encoding for four amino acids may be acceptable) or larger (the minimum number for higher animals is as high as 19, indicating that a portion encoding for at least seven amino acids may be necessary) [see Oligonucleotides: Antisense Inhibitors of Gene Expression, vol. 12, pages 137–140, Macmillan Press Ltd., London (1989)] may be used to obtain similar results However, because there may not be a precise match between the nucleotide sequence in the corresponding portions between species, oligomers containing approximately 15 nucleotides are a preferred minimum in order to achieve hybridization under conditions of sufficient stringency to eliminate false positives; the sequence encoding 5 amino acids would supply information sufficient for the generation of such probes.

By way of example, a comparison of the T. aquaticus ligase and E. coli amino acid sequences reveals an identity between amino acids 34–40 (Asp-Ala-Glu-Tyr-Asp-Arg-Leu)(SEQ. ID. No. 3 ) at statistically acceptable levels. Using the preferred six amino acid sequence, a degenerate probe of the form GA(C/T)-GC(G/A/T/C)-GA(G/A)-TA(C/T)-GA(C/T)-(C/A)G(G/A/T/C)-(C/T)T could be used to identify and retrieve either of the above ligases. The areas of sequence identities between the Thermophilus ligase according to the present invention and E. coli ligase include the amino acids at the following positions:

| Amino Acid Positions | Consecutive identical aa's |
|---|---|
| 34 to 40 | 7 |
| 57 to 61 | 5 |
| 137 to 142 | 6 |
| 168 to 175 | 8 |
| 199 to 210 | 12 |
| 212 to 219 | 8 |
| 308 to 312 | 5 |
| 333 to 339 | 7 |
| 485 to 490 | 6 |
| 492 to 496 | 5 |
| 513 to 517 | 5 |
| 620 to 624 | 5 |

Overall, of the 676 amino acids contained in the ligase according to the present invention, the percent similarity between the Thermophilus ligase and E. coli ligase is 66%; the percent identity is 47%.

The construction of an overproducer strain from a cloned and properly oriented gene may be achieved by using procedures which are conventional in the art. The general principle of such construction is to bring an enabling sequence into close proximity to the starting codon of the gene to affect efficient transcription and translation of that gene. There are many promoter systems (including a ribosome binding site [see Proc. Natl. Acad. Sci. USA 10 78:5543 (1981)]) that have been successfully used to turn on genes, including the lac promoter, the trp promoter [see Gene 20:231 (1982)], the lambda phage PL promoter [see Nature 292:128 (1981)], the tac fusion promoter [see Proc. Natl. Acad. Sci. USA 80:21 (1983)], and the T7 phage promoters [see Proc. Natl. Acad. Sci. USA 82:1074 (1985)].

Plasmid pDZ1 contains the T. aquaticus ligase gene downstream from both lac and T7 promoters present in the starting vector. There are several methods for removing excess DNA sequences from between the promoters and the gene, including use of Bal31 [see Nucl. Acids Res. 5:1445 (1978)] and ExoIII and Mung Bean or $S_1$ Nuclease [see Meth. Enzymol. 155:156 (1987)]. However, a somewhat simpler method as described in Example V was used to bring the amino terminus of the T. aquaticus ligase gene closer to the two promoters in the present instance.

EXAMPLE V (Removal of Excess DNA from between Promoter and Gene)

Plasmid pDZ1 was randomly linearized with the restriction endonuclease HinPI (G CGC) and blunt ended with Klenow or alternatively with CviJI (PuG CPy) [see DNA and Protein Engineering Techniques 1:29 (1988)].

DNA was purified by sequential extractions with phenol (2×), n-butanol (2×), and the nucleic acid recovered by precipitation with ethanol. These randomly linearized plasmids were then treated with Asp718 which cleaves the polylinker site directly downstream of the two promoters, and blunt ended with Klenow. The resulting fragments were separated via electrophoresis in low melting agarose, sequential slices (including full length linear and progressively smaller DNA fragments) excised, and the DNA recovered. The DNA fragments were subsequently recirculoarized by blunt end ligation. This involved overnight incubation at 40° C. in 100 μl in 50 mM Tris HCl pH 8.0 buffer containing 10 mM $MgCl_2$, 1 mM EDTA, 1 mM ATP, 6 mM mercaptoethanol, and from 3 to 7 Weiss units of T4 ligase. After ligations, EDTA was added, the T4 ligase inactivated by heat (for 15 min at 65° C.), and nucleic acids recovered by ethanol precipitation.

The ligation mixes prepared were introduced into AK76 cells using conventional techniques, and the $lig^+$ phenotype was selected at 42° C. on SOB plates containing maltose, IPTG, and ampicillin as described previously.

Based upon previous work, plasmids containing deletions between the promoters and the start of the T. aquaticus ligase gene would be expected to confer viability under these conditions. Deletions of the vector (promoter regions), or of an essential portion of the ligase gene should not confer viability. Therefore, individual clones were picked, plasmid DNA prepared using conventional methods [see Anal. Biochem. 114:193 (1981)], and analyzed by restriction digestion. Results from this testing found that plasmid pDZ2, pDZ3, pDZ6 and pDZ7 lacked the 1.8 kb BamHI fragment, and contained instead a 1.3, 1.4, 1.2, or 1.2 kb fragment, respectively. All these plasmids re-created the Asp718 site as would be expected with proper blunt end fill-ins and ligations. Single stranded DNA was prepared from these plasmids using conventional techniques [see Nucl. Acids Research 13:1103 (1985), and Protein Engineering 1:64 (1986)], and these were sequenced using the universal "reverse primer" oligonucleotide 5'd (AGCGGATAACAATTTCACACAGGA)3' (SEQ. ID. No. 5) and T7 DNA polymerase [see Proc. Natl, Acad. Sci. USA 84:4767 (1987)].

Analysis of the DNA sequence reveals two ATG start codons, the first open reading frame being three codons in length and the second, the ligase DNA sequence, giving a long reading frame. In conjunction with FIG. 1, this sequence (including the partial ligase DNA sequence) derived from plasmids pDZ6 and pDZ7 is:

pTZ18R (SEQ. ID. No. 6)
GGCTCGTATG TTGTGTTGGAA TTGTGAGCGG ATAACAATTT

LacZ'    T7 Promoter
CACACAGGAA ACAGCTATGA CCATGATTAC GAATTTAATA pDZ6,7
CGACTCACTA TAGGGAATTC GAGCTCGGTA CCCCAAGGTA
       EcoRI   SacI    KpnI

CACTAGGGCC thermophilic ligase

| | | | | | | | | | | | | |
|---|---|---|---|---|---|---|---|---|---|---|---|---|
| ATG | ACC | CTG | GAA | GAG | GCG | AGG | AAG | CGG | GTA | AAC | GAG | TTA | 39 |
| CGG | GAC | CTC | ATC | CGC | TAC | CAC | AAC | TAC | CGC | TAC | TAC | GTC | 78 |
| CTG | GCG | GAC | CCG | GAG | ATC | TCC | GAC | GCC | GAG | TAC | GAA | CGG | 117 |
| CTT | CTT | AGG | GAG | CTC | AAG | GAG | CTT | GAG | GAG | CGC | TTC | CCC | 156 |
| GAG | CTC | AAA | AGC | CCG | GAC | TCC | CCC | ACC | CTT | CAG | GTG | GGG | 195 |
| GCG | AGG | CCT | TTG | GAG | GCC | ACC | TTC | CGC | CCC | GTC | CGC | CAC | 234 |
| CCC | ACC | CGC | ATG | TAC | TCC | TTG | GAC | AAC | GCC | TTT | AAC | CTT | 273 |
| GAC | GAG | CTC | AAG | GCC | TTT | GAG | GAG | CGG | ATA | GAA | CGG | GCC | 312 |
| CTG | GGG | CGG | AAG | GGC | CCC | TTC | GCC | TAC | ACC | GTG | GAG | CAC | 351 |
| AAG | GTG | GAC | GGG | CTT | TCC | GTG | AAC | CTC | TAC | TAC | GAG | GAG | 390 |
| GGG | GTC | CTG | GTC | TAC | GGG | GCC | ACC | GCC | GGG | GAC | GGG | GAG | 329 |
| GTG | GGG | GAG | GAG | GTC | ACC | CAG | AAC | CTC | CTC | ACC | ATC | CCC | 368 |
| ACC | ATC | CCG | AGG | AGG | CTC | AAG | GGG | GTG | CCG | GAG | CGC | CTC | 407 |
| GAG | GTC | CGG | GGG | GAG | GTC | TAC | ATG | CCC | ATA | GAG | GCC | TTC | 446 |
| CTC | CGG | CTC | AAC | GAG | GAG | CTG | GAG | GAG | CGG | GGG | GAG | AGG | 483 |
| ATC | TTC | AAA | AAC | CCT | AGG | AAT | GCG | GCG | GCG | GGT | TCC | TTA | 524 |
| AGG | CAA | AAA | GAC | CCC | CGC | ATC | ACC | GCC | AAG | CGG | GGC | CTC | 563 |
| AGG | GCC | ACC | TTC | TAC | GCC | TTA | GGG | CTT | GGG | CTG | GAG | GAG | 602 |
| GTG | GAG | AGG | GAA | GGG | GTG | GCG | ACC | CAG | TTT | GCC | CTC | CTC | 641 |
| CAC | TGG | CTC | AAG | GAA | AAA | GGC | TTC | CCC | GTG | GAG | CAC | GGC | 680 |
| TAC | GCC | CGG | GCC | GTG | GGG | GCG | GAA | GGG | GTG | GAG | GCG | GTC | 719 |
| TAC | CAG | GAC | TGG | CTC | AAG | AAG | CGG | CGG | GCG | CTT | CCC | TTT | 758 |
| GAG | GCG | GAC | GGG | GTG | GTG | GTG | AAG | CTG | GAC | GAG | CTT | GCC | 797 |
| CTT | TGG | CGG | GAG | CTC | GGC | TAC | ACC | GCC | CGC | GCC | CCC | CGG | 836 |
| TTC | GCC | ATC | GCC | TAC | AAG | TTC | CCC | GCC | GAG | GAG | AAG | GAG | 875 |

-continued

```
ACC CGG CTT TTG GAC GTG GTC TTC CAG GTG GGG CGC ACC   914

GGG CGG GTG ACC CCC GTG GGG ATC CTC GAG CCC GTC TTC   953

CTA GAG GGC AGC GAG GTC TCC CGG GTC ACC CTG CAC AAC   992

GAG AGC TAC ATA GAG GAG TTG GAC ATC CGC ATC GGG GAC  1031

TGG GTT TTG GTG CAC AAG GCG GGC GGG GTC ATC CCC GAG  1070

GTC CTC CGG GTC CTC AAG GAG AGG CGC ACG GGG GAG GAA  1109

AGG CCC ATT CGC TGG CCC GAG ACC TGC CCC GAG TGC GGC  1148

CAC CGC CTC CTC AAG GAG GGG AAG GTC CAC CGC TGC CCC  1187

AAC CCC TTG TGC CCC GCC AAG CGC TTT GAG GCC ATC CGC  1226

CAC TTC GCC TCC CGC AAG GCC ATG GAC ATC CAG GGC CTG  1265

GGG GAA AAG CTC ATT GAG AGG CTT TTG GAA AAG GGG CTG  1304

GTC AAG GAC GTG GCC GAC CTC TAC CGC TTG AGA AAG GAA  1343

GAC CTG GTG GGC CTG GAG CGC ATG GGG GAG AAG AGC GCC  1382

CAA AAC CTC CTC CGC GAG ATA GAG GAG AGC AAG AAA AGA  1421

GGC CTG GAG CGC CTC CTC TAC GCC TTG GGG CTT CCC GGG  1460

GTG GGG GAG GTC TTG GCC CGG AAC CTG GCG GCC CGC TTC  1499

GGG AAC ATG GAC CGC CTC CTC GAG GCC AGC CTG GAG GAG  1538

CTC CTG GAG GTG GAG GAG GTG GGG GAG CTC ACG GCG AGG  1577

GCC ATC CTG GAG ACC TTG AAG GAC CCC GCC TTC CGC GAC  1616

CTG GTA CGG AGG CTC AAG GAG GCG GGG GTG GAG ATG GAG  1655

GCC AAG GAG AAG GGC GGG GAG GCC CTT AAA GGG CTC ACC  1694

TCC GTG ATC ACC GGG GAG CTT TCC CGC CCC GGG AAA GAG  1733

GTG AAG GCC CTC CTA AGG CGC CTC GGG GCC AAG GTG ACG  1772

GAC TCC GTG AGC CGG AAG ACG AGC TAC CTC GTG GTG GGG  1811

GAG AAC CCG GGG GAG AAC CCG GGG AGC AAG CTG GAG AAG  1850

GCC AGG GCC CTC GGG GTC CCC ACC CTC ACG GAG GAG GAG  1889

CTC TAC CGG CTC CTG GAG GCG CGG ACG GGG AAG AAG GCG  1928

GAG GAG CTC GTC TAA AGGCTTCC 1971
```

The nucleic acid sequence for the thermophilic ligase according to the present invention corresponds to the amino acid sequence(SEQ. ID. No. 8):

```
Met Thr Leu Glu Glu Ala Arg Lys Arg Val Asn Glu Leu Arg Asp
                 5                  10                  15
Leu Ile Arg Tyr His Asn Tyr Arg Tyr Tyr Val Leu Ala Asp Pro
                20                  25                  30
Glu Ile Ser Asp Ala Glu Tyr Asp Arg Leu Leu Arg Glu Leu Lys
                35                  40                  45
Glu Leu Glu Glu Arg Phe Pro Glu Leu Lys Ser Pro Asp Ser Pro
                50                  55                  60
Thr Leu Gln Val Gyl Ala Arg Proi Leu Glu Ala Thr Phe Arg Pro
                65                  70                  75
Val Arg His Pro Thr Arg Met Tyr Ser Leu Asp Asn Als Phe Asn
                80                  85                  90
Leu Asp Glu Leu Lys Ala Phe Glu Glu Arg Ile Glu Arg Ala Leu
                95                 100                 105
Gly Arg Lys Gly Pro Phe Ala Tyr Thr Val Glu His Lys Val Asp
               110                 115                 120
Gly Leu Ser Val Asn Leu Tyr Tyr Glu Glu Gly Val Leu Val Tyr
               125                 130                 135
Gly Als Thr Arg Gly Glu Gly Glu Val Gly Glu Glu Val Thr Gln
               140                 145                 150
Asn Leu Leu Thr Ile Pro Thr Ile Pro Arg Arg Leu Lys Gly Val
               155                 160                 165
Pro Glu Arg Leu Glu Val Arg Gly Glu Val Tyr Met Pro Ile Glu
               170                 175                 180
Ala Phe Leu Arg Leu Asn Glu Glu Leu Glu Glu Arg Gly Glu Arg
               185                 190                 195
Ile Phe Lys Asn Pro Arg Asn Ala Ala Ala Gly Ser Leu Arg Gln
               200                 205                 210
Lys Asp Pro Arg Ile Thr Ala Lys Arg Gly Leu Arg Ala Thr Phe
               215                 220                 225
Tyr Ala Leu Gly Leu Gly Leu Glu Glu Val Glu Arg Glu Gly Val
               230                 235                 240
Ala Thr Gln Phe Ala Leu Leu His Trp Leu Lys Glu Lys Gly Phe
               245                 250                 255
Pro Val Glu His Gly Tyr Ala Arg Ala Val Gly Ala Glu Gly Val
               260                 265                 270
Glu Ala Val Tyr Gln Asp Trp Leu Lys Lys Arg Arg Ala Leu Pro
               275                 280                 285
Phe Glu Ala Asp Gly Val Val Lys Leu Asp Glu Leu Ala Leu
               290                 295                 300
Try Arg Glu Leu Gly Tyr Thr Ala Arg Ala Pro Arg Phe Ala Ile
               305                 310                 315
Ala Tyr Lys Phe Pro Ala Glu Glu Lys Glu Thr Arg Leu Leu Asp
               320                 325                 330
Val Val Phe Gln Val Gly Arg Thr Gly Arg Val Thr Pro Val Gly
               335                 340                 345
Ile Leu Glu Pro Val Phe Leu Glu Gly Ser Glu Val Ser Arg Val
               350                 355                 360
Thr Leu His Asn Glu Ser Tyr Ile Glu Glu Leu Asp Ile Arg Ile
               365                 370                 375
Gly Asp Trp Val Leu Val His Lys Ala Gly Gly Val Ile Pro Glu
               380                 385                 390
Val Leu Arg Val Leu Lys Glu Arg Arg Thr Gly Glu Glu Arg Pro
               395                 400                 405
```

-continued

| | | | | | | | | | | | | |
|---|---|---|---|---|---|---|---|---|---|---|---|---|
| Ile | Arg | Trp | Pro | Glu 410 | Thr | Cys | Pro | Cys 415 | Gly | His | Arg | Leu | Leu 420 |
| Lys | Glu | Gly | Lys | Val 425 | His | Arg | Cys | Pro | Asn 430 | Pro | Leu | Cys | Pro | Ala 435 |
| Lys | Arg | Phe | Glu | Ala 440 | Ile | Arg | His | Phe | Ala 445 | Ser | Arg | Lys | Ala | Met 450 |
| Asp | Ile | Gln | Gly | Leu 455 | Gly | Glu | Lys | Leu | Ile 460 | Glu | Arg | Leu | Leu | Glu 465 |
| Lys | Gly | Leu | Val | Lys 470 | Asp | Val | Ala | Asp | Leu 475 | Tyr | Arg | Leu | Arg | Lys 480 |
| Glu | Asp | Leu | Val | Gly 485 | Leu | Glu | Arg | Met | Gly 490 | Glu | Lys | Ser | Ala | Gln 495 |
| Asn | Leu | Leu | Arg | Gln 500 | Ile | Glu | glu | Ser | Lys 505 | Lys | Arg | Gly | Leu | Glu 510 |
| Arg | Leu | Leu | Tyr | Ala 515 | Leu | Gly | Leu | Pro | Gly 520 | Val | Gly | Glu | Val | Leu 525 |
| Ala | Arg | Asn | Leu | Ala 530 | Ala | Arg | Phe | Gly | Asn 535 | Met | Asp | Arg | Leu | Leu 540 |
| Glu | Ala | Ser | Leu | Glu 545 | Glu | Leu | Leu | Glu | Val 550 | Glu | glu | Val | Gly | Glu 555 |
| Leu | Thr | Ala | Arg | Ala 560 | Ile | Leu | Glu | Thr | Leu 565 | Lys | Asp | Pro | Ala | Phe 570 |
| Arg | Asp | Leu | Val | Arg 575 | Arg | Leu | Lys | Glu | Ala 580 | Gly | Val | Glu | Met | Glu 585 |
| Ala | Lys | Glu | Lys | Gly 590 | Gly | Glu | Ala | Leu | Lys 595 | Gly | Leu | Thr | Phe | Val 600 |
| Ile | Thr | Gly | Glu | Leu 605 | Ser | Arg | Pro | Arg | Glu 610 | Glu | Val | Lys | Ala | Leu 615 |
| Leu | Arg | Arg | Leu | Gly 620 | Ala | Lys | Val | Thr | Asp 625 | Ser | Val | Ser | Arg | Lys 630 |
| Thr | Ser | Tyr | Leu | Val 635 | Val | Gly | Glu | Asn | Pro 640 | Glu | Ser | Lys | Leu | Glu 645 |
| Lys | Ala | Arg | Ala | Leu 650 | Gly | Val | Pro | Thr | Leu 655 | Thr | Glu | Glu | Glu | Leu 660 |
| Tyr | Arg | Leu | Leu | Glu 665 | Ala | Arg | Thr | Gly | Lys 670 | Lys | Ala | Glu | Glu | Leu 675 |
| Val | | | | | | | | | | | | | | |

Translation of the first 60 amino acids of this open reading frame (the thermophilic ligase) shows better than 50% homology to *E. coli* ligase [see Mol. Gen. Genet. 204:1 (1986)] suggesting that this long open reading frame represents the start of the *T. aquaticus* gene. From the genetic results with the BamHI fragments, one can conclude that the size of this ligase is between 400 and 1,100 amino acids in length. The purified protein has been reported to have a molecular weight of about 79,000 [see J. Biol. Chem. 259:10041 (1984)] which is within the limits of the genetic results found for the present invention. Given that clone pDZ7 produces functional *T. aquaticus* ligase (that is it encodes the gene in its entirety), and given the DNA sequence of the amino terminus, the entire DNA sequence of the gene was determined using either manual or automated methods as described in the literature [see, for example, Proc. Natl. Acad. Sci. 84:4767 (1987); Proc. Natl. Acad. Sci. 86:4076 (1989); Science 239:487 (1987); Nature 321:674 (1986); Biotechniques 8:184 (1990); Proc. Natl. Acad. Sci. USA 85:5610 (1988); and Proc. Natl. Acad. Sci. USA 85:9436 (1988)].

Plasmids pDZ2, pDZ3, pDZ6 or pDZ7 may be used to construct further overproduction vectors using methods common to those skilled in biotechnology studies. This may include using promoters and ribosome binding sites as described above. For example, plasmid pDZ7 (see FIG. 1) may be linearized at its unique Asp718 site, and excess nucleotides in front of the *T. aquaticus* ligase gene trimmed close to the ATG start codon by the use of Bal31 or a combination of ExoIII and Mung Bean or $S_1$ Nuclease as described above. This may then be blunt end ligated to a natural enabling sequence (a promoter and translation start sequence) generated in a similar manner, or by a synthetic enabling sequence manufactured for this purpose. In addition, sequences external or internal to the *T. aquaticus* gene may be modified to remove potential RNA structures that may inhibit transcription or translation. These methods have been reported previously to affect overproduction of the thermophilic restriction endonuclease Taq I to greater than 30% of soluble *E. coli* proteins [see Gene 65:166 (1988)]. Alternatively, synthetic oligonucleotides may be synthesized such that the start of the *T. aquaticus* ligase gene is fused directly to an enabling sequence using PCR methods [see, for example, Biotechniques 8:178 (1990); Gene 77:51 (1989); and Nucl. Acids Res. 17:723 (1989)].

From the preceeding sequences, it can be seen that there is a BgI II site corresponding to the nucleotides that code for amino acid residues 31–33. With this information, a strong promoter with an optimal Shine-Dalgarno sequence could be inserted in front of this gene using PCR. Two minor caveats need to be considered: (1) attempts to PCR copy the entire gene (3 kb, high GC content) were not always successful, and (2) plasmid pDZ7 had two Bam HI and BgI II sites, one each within the ligase gene.

Figure 9:
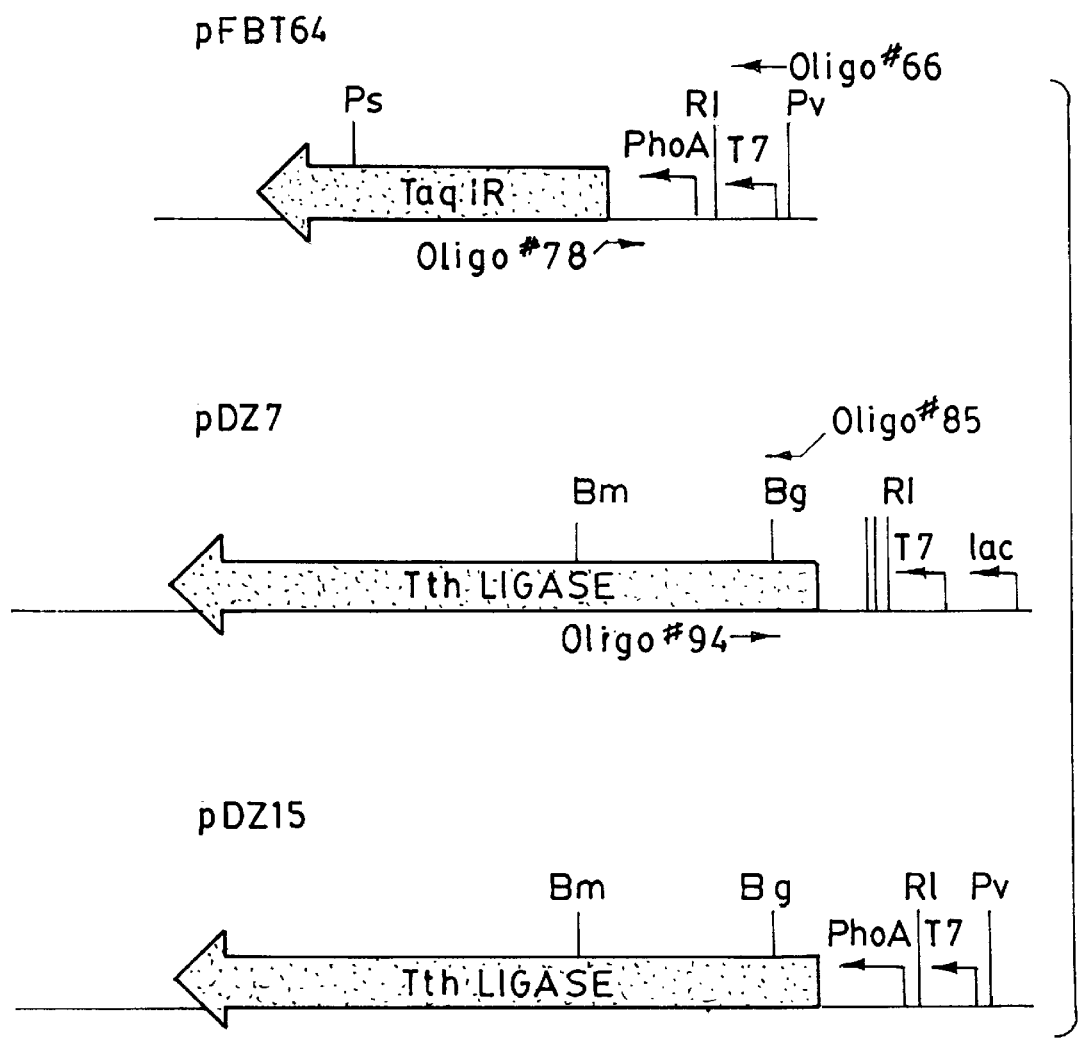
FIG. 9 is a depiction of three clones prepared in accordance with the present invention.

Plasmid pDZ7 was partially digested with both Bam HI and BgI II, the correct size smaller linear fragment separated from full length linear by electrophoresis, excised, and purified as described previously. Since Bam HI and BgI II produce the same overhang (5' GATC), the linear fragment could be recircularized with T4 ligase, and introduced into E. coli strain AK53 via transformation. Several clones had deleted the 0.5 kb Bam HI/BgI II fragment resulting in a 5.7 kb plasmid, and one such clone was designated pDZ12. Synthetic oligonucleotides #66, #78, #85, and #94 were synthesized, to allow for fusion of pho A promoter [from plasmid pFBT64; see Gene 56:13 (1987)] and ribosome binding sequence to the start of the ligase gene using PCR [see Biotechniques 8:178 (1990); Gene 77:51 (1989); Gene 77:61 (1989); and Nucl. Acids Res.17:723 (1989)]. These clones are depicted in FIG. 9, and are:

66 19 mer; Pvu II site to T7 promoter through phoA promoter, top strand of plasmid pFBT64 (direction of TaqI endonuclease gene)(SEQ. ID. NO. 9):
5' CTG GCT TAT CGA AAT TAA T 3'

78 32 mer; 5' end complementary to start of Thermus ligase gene; 3' end complementary to Shine-Dalgarno side of pho A promoter, bottom strand of plasmid pFBT64:
5' CCA GGG TCA TTT TAT TTT CTC CAT GTA CAA AT 3'

85 33 mer; 5' end complementary to Shine-Dalgarno side of pho A promoter; 3' end complementary to start of Thermus ligase gene, top strand of plasmid pDZ7 (direction of ligase gene)(SEQ. ID. No. 11):
5 5' CAT GGA GAA AAT AAA ATG ACC CTG GM GAG GCG 3'

94 18 mer; bottom strand of plasmid pDZ7 corresponding to non-translated strand of amino acid residues 40 to 35 of ligase gene, downstream of BgI II site at amino acid residues 33 to 31 (SEQ. ID. No. 12):
5' AAG CCG GTC GTA CTC GGC 3'

Briefly, this was accomplished in a single reaction tube in which 400 ng of primers #66 and #78 were added to 200 ng of Pst I/Pvu II digested pFBT64 containing 50 μmoles of dATP, cCTP, cGTP, and dTTP each, and 2.5 units Amplitaq in 100 μl PCR buffer and cycled at 94° C. for 1 min, 55° C. for 2 min, 72° C. for 3 min with 3 sec. extension per cycle for 25 cycles as per the manufacturer's (Cetus, Emoryville, Calif.) protocol. A second reaction tube contained 400 ng of primers #85 and #94, 200 ng of Eco RI/Bam HI digested pDZ7, in the same reaction buffer and enzyme, and incubated as above. The products of these reactions were shown to be the correct length as analyzed by gel electrophoresis. A third reaction tube contained 2μl from each product, 400 ng primers #66 and #94 in the same reaction buffer and enzyme, and incubated as above. Primers were designed such that overlap between the two products would allow for PCR synthesis of the combined length fused product. The resultant fragment was extracted with phenol, n-butanol, and ethanol precipitated to remove Taq polymerase. The product PCR fragment was treated with BgI II and Eco RI, electrophoresed in low melting agarose, and purified as described above. Meanwhile, the 2.7 kb Pst I-BgI II ligase gene containing fragment from pDZ12 and the 2.4 kb Pst I-Eco RI β-lactamase gene and origin containing fragment from pFBT64 were purified. All three fragments were combined in a three way ligation and introduced into E. coli strain AK53 via transformation. Several clones contained a 5.5 kb plasmid which overproduced ligase under pho A promoter control. One such plasmid has been designated pDZ13.

In reported studies in overproduction of the thermophilic restriction endonuclease Taq I to greater than 30% of soluble E. coli proteins [see Gene 65:166 (1988)], it was noticed that endonuclease yields were somewhat better if the β-lactamase gene was reversed, and hence transcribing in the opposite direction as the pho A promoter. To make a similar construction with the ligase gene according to the present invention, the 2.3 kb Pst I-Pvu II fragment from plasmid pFBLT69 (which contains the β-lactamase in reverse orientation) was ligated to the 3.2 kb Pst I-Pvu II ligase gene containing fragment of plasmid pDZ13. The ligation mix was transformed into E. coli strain AK53, and several transformants were analyzed by restriction digests to confirm the orientation of β-lactamase gene. One such clone has been designated pDZ15. Production of ligase in pDZ15 is as good as, if not slightly better than, pDZ13. The ligase enzyme appears to be somewhat sensitive to proteases, and the cells should be grown for no more than 9 hours after induction. Proteolytic products of the ligase gene may still have thermostable ligase activity (this has been demonstrated for Taq polymerase).

Thermophilic proteins may be substantially modified and still retain sufficient activity for use in the present invention. For example, it has been shown that deletion of approximately one-third of the coding sequence at the amino-terminus of Taq polymerase still produces a gene product that is active in polymerase activity [see J. Biol. Chem. 264:6427 (1989)]. Alternatively, another thermophilic protein, the restriction endonuclease Taq I, was shown to retain essentially full activity when amino acids were added to the amino-terminus (+7), the carboxy-terminus (+38), or at certain positions internally (from +2 to +34) [see Gene 65:166 (1988)]. Thus, modification of the primary structure by deletion, n-terminus addition, c-terminus addition, internal addition or duplication, or alteration of the amino acids incorporated into the sequence during translation can be made without destroying the activity or thermostable nature of the protein. In addition, the availability of DNA encoding these sequences provides the opportunity to modify the codon sequence so as to generate mutein forms also having ligase activity. Such substitutions or other alterations result in novel proteins having amino acid sequence encoded by DNA falling within the scope of the present invention.

It will also be appreciated that other ligating proteins may be isolated by the process according to the present invention as exemplified in these examples. Different cell lines may be expected to produce ligases having different physical properties to that isolated from the T. aquaticus HB8 strain used in the making of the present invention. Additionally, variations may exist due to genetic polymorphisms or cell-mediated modifications of the enzyme or its precursors. Furthermore, the amino acid sequence of a ligase so isolated may be modified by genetic techniques to produce ligases with altered biological activities and properties. The resultant DNA sequence may then be able to encode a protein having substantially the same amino acid sequence as T. aquaticus HB8 ligase, but exhibiting a higher or lower level of activity. Such ligating proteins should also be considered to be within the scope of the present invention.

EXAMPLE VI (Purification of Ligase Enzyme)

*E. Coli* cells AK53 containing plasmids pDZ6 and pGP1–2 (containing the T7 RNA polymerase gene behind the lambda $P_L$ promoter and under control of the temperature sensitive lambda repressor $C_{I587}$) [see Proc. Natl. Acad. Sci. USA 82:1074 (1985) and U.S. Pat. No. 4,795,699, ] were grown overnight at 32° C. on TY plates containing ampicillin at 50 μml and kanamycin at 50 μg/ml to ensure maintenance of both plasmids. Fresh colonies were resuspended in 1 liter of sterile 50 mM Tris HCl buffer at pH 7.6 and containing 6 g NaCl, 25 g Bacto™ tryptone, 7.5 g yeast extract, 1 g glucose, 1.6 g casein amino acid hydrolysate, 50 μg/ml kanamycin and 50 μg/ml ampicillin, and grown at 32° C. in a 2 liter flask shaking at 200 rpm. When the $O.D._{550}$ reached between 0.8 and 1.0, synthesis of the T7 polymerase was induced by shifting the cells to 42° C. for 30 to 40 minutes. Further synthesis of *E. coli* proteins were inhibited by the addition of 5 ml of 20 mg/ml rifampicin dissolved in methanol to a final concentration of 100 μg/ml. Under these conditions, only genes behind the T7 promoter should be transcribed and hence translated. Cells were incubated for an additional 5 hours at 42° C.

Alternatively, *E. coli* cells AK53 containing plasmids pDZ15 (ligase under pho A promoter control) were grown overnight at 37° C. on TY plates containing ampicillin at 50 μg/ml. Fresh colonies were resuspended in 50 ml of fortified broth containing 50 μg/ml ampicillin and grown at 37° C. in a 500 ml flask shaking at 200 rpm in a G76 benchtop shaker. When the $O.D._{500}$ reached between 0.65 and 0.85, 20 ml was diluted into 1 liter of MOPS media containing 0.2 mM $K_2HPO4$ [see J. Bacteriology 119:736 (1974)] to induce the phoA promoter. Cells were grown at 37° C. in a 2 liter flask shaking at 200 rpm in a G25 floor shaker for an additional 9 hours.

Following incubation, the cells were chilled in ice, harvested by centrifugation (5,000 rpm for 15 min), resuspended in 20 ml of water, transferred to 35 ml centrifuge tubes, recentrifuged (7,000 rpm for 6 min), and the pellet frozen until ready for protein isolation. After thawing, the pellet was resuspended in 20 ml of buffer A (20 mM Tris HCl buffer at pH 7.6 containing 1 mM EDTA) containing 10 mM 2-mercaptoethanol and 0.15 mM PMSF. After sonication (5×1 min at 50% power at 4° C.), the solution was centrifuged at 39,000 ×g for 60 min.

The enzyme has an estimated molecular weight of from 75,000 to 85,000 daltons when compared with a phosphorylase B standard assigned a molecular weight of 92,500 daltons.

Alternatively, 2 liters of pDZ15 induced cells were harvested, sonicated, and debris cleared by centrifugation as described above.

The supernatant (40 ml) was brought to 300 mM KCl and passed through a 5 ml DEAE sephacel column to remove extraneous DNA using 70 ml buffer A containing 0.3 M KCl. The flowthrough fractions containing the ligase were combined, and treated at 65° C. for 20 minutes to irreversably heat denature many *E. coli* enzymes including endo or exonucleases. Denatured proteins were then removed by centrifugation at 39,000 ×g for 15 minutes, and the ligase enzyme precipitated from the supernatant by adding an equal volume of saturated $(NH_4)_2SO_4$ at room temperature for 30 minutes. The ammonium sulfate precipitate was harvested by centrifugation at 8,000 rpm in a clinical centrifuge, and resuspended in 4 ml of distilled water.

Samples were dialyzed against buffer A, followed by buffer A containing 50 mM KCl. The dialized protein solution was applied to a 40 ml phosphocellulose column equilibrated with buffer A containing 50 mM KCl. After washing with 80 ml of the same buffer, the column was eluted with a 120 ml linear gradient of KCl (0.05 to 0.5 M) in buffer A. The enzyme eluted as a sharper peak from 0.25 to 0.35 M KCl. The protein migrates as two bands of apparent molecular weight approximately 81,000 (adenylated form) and 78,000 (non-adenylated form) and is about 98–99% pure as monitored by SDS-10% polyacrylamide gel electrophoresis. One can convert between the two forms by incubating 150 μg protein in ligase buffer containing either 25 μg nicked Salmon sperm DNA without NAD (resulting in the non-adenylated form), or in ligase buffer with 10 mM NAD (resulting in the adenylated form) for 30 min at 65° C. An equal volume of 20 mM Tris HCl pH 8.0 in 100% glycerol containing 1 mM EDTA, 2 mM dithiothreitol (DTT), and 200 μg/ml Bovine Serum Albumin (Fraction V) is added (final glycerol concentration is 50%), and enzyme stored at either −70° C. or −20° C. From 2 liters of cells, a final yield of 6 mg ligase in 16 ml storage buffer, at 625 nick closing units per microliter. This corresponds to a total of 10,000,000 units of enzyme, and a specific activity of 1,666,667 units/mg.

Since it is known that thermophilic proteins tend to be somewhat more hydrophobic than their mesophilic counterparts, addition of non-ionic detergents or other stabilizing agents may help in long term storage. Storage buffers may therefore include additional components such as glycerol (50%), sucrose (25%), protease inhibitors (0.5–1.0 mM PMSF, $10^{-7}$ M pepstatin A), salt (KCl, preferably at 100–500 mM), EDTA (0.1–1.0 mM) bovine serum albumin (100–500 μg/ml), gelatin, dithiothreitol (1–10 mM), and mercaptoethanol (1–10 mM). In addition, it is preferable that the storage buffer contain at least one non-ionic polymeric detergent. A partial listing of such detergents would include ethoxylated fatty alcohol ethers and lauryl ethers, ethoxylated alkyl phenols, polyethylene glycol monooleate compounds, and more particularly Triton X-100, NP-40, and Tween 20 at 0.1–0.5% vol/vol.

To assay for ligase activity, it is important to use a method that is not skewed by the melting temperature ($T_m$) of the substrates. For example, a 4 base cohesive end ligation is most efficient at a low temperature such as 4° C., well below the temperature optimum for T4 ligase (which is 37° C.), and certainly below the temperature optimum of a thermophilic ligase. One assay method that should be consistent is the nick-closing assay in which circular plasmid DNA is randomly nicked in several places by DNaseI. The ability of ligase to close all these nicks and generate covalently closed circular DNA can be assayed by separating nicked circle from open circle DNA via electrophoresis in an agarose gel containing ethidium bromide. For example, the covalently closed circular form of plasmid pUC4KIXX [see Gene 37:111 (1985)] migrates faster than the linear form, and considerably faster than the nicked form on a 1% agarose gel containing 0.2 M glycine NaOH pH 8.5 0.1 mM EDTA, and 1, μg/ml ethidium bromide and run at 150V for 1.5 hr in the same buffer.

EXAMPLE VII (Thermophilic Ligase Assay)

Nicked pUC4KIXX DNA was generated by adding 3 μgl of freshly diluted 1 μg/ml DNaseI to 5 μg DNA in 50 μl of 50 mM Tris HCl ph 8.0 buffer containing 10 mM $MgCl_2$, 1 mM EDTA, and 6 mM mercaptoethanol. The mixture was incubated at room temperature for 5 min, the DNase heat killed at 65° C. for 10 min, and the sample stored until used be freezing at −20° C. Under these conditions, about 90% of the DNA was in the nicked circular form, with about 5% in the linear and 5% in the covalently closed circular form.

Thermophilic ligase prepared as above was assayed by adding serial dilutions of ligase to 0.5 μg nicked pUC4KIXX in 20 μl of 20 mM Tris HCl pH 7.6 buffer containing 50 mM KCl, 10 mM $MgCl_2$, 1 mM EDTA, 10 mM NAD, 10 mM dithiothreitol, overlaying with a drop of mineral oil, and incubating at 65° C. for 15 min. As a control, T4 ligase was assayed by adding serial dilutions of ligase to 0.5 μg nicked pUC4KIXX in 20 μl of 50 mM Tris HCl pH 8.0 buffer containing 10 mM $MgCl_2$, 1 mM EDTA, 1 mM ATP, 6 mM mercaptoethanol, and incubating at 37° C. for 15 min.

Reactions were terminated by the addition of 4 μl stop buffer containing 0.2 M EDTA, 50% glycerol, 1% SDS and 0.1% bromphenol blue, and the products were analyzed by gel electrophoresis as described above.

One nick closing unit of ligase is defined as the amount of ligase that circularizes 0.5 μg of nicked pUC4KIXX DNA under the buffer and time conditions set forth in the preceding example, such that addition of further ligase does not circularize additional DNA.

As a mini-prep procedure, E. coli cells AK53 containing plasmids pDZ15 (ligase underphoA promoter control) were grown overnight at 37° C. on TY plates containing ampicillin at 50 μg/ml. Fresh colonies were resuspended in 5 ml of fortified broth containing 50 μg/ml ampicillin, and grown at 37° C. When the $O.D._{550}$ reached between 0.65 and 0.85, 0.12 ml was diluted into 6 ml of MOPS media containing 0.2 mM $K_2HPO_4$ to induce the pho A promoter. Cells were incubated overnight at 37° C. (some proteolysis that occurs after prolonged incubation, so caution is advised in overgrowing induced cells). Cells were harvested in 1.5 ml microcentrifuge tubes, resuspended in 0.3 ml of 20 mM Tris HCL pH 7.6 containing 1 mM EDTA and 10 mM 2-mercaptoethanol, and sonicated 2×10 seconds. After clear debris by centrifugation (12,000 rpm for 2 min.), the supernatant was treated at 65° C. for 20 min to irreversably heat denature many E. coli enzymes including the endo and exonucleaseses [see Gene 56:13 (1987)]. The denatured debris was removed by centrifugation and the supernatant assayed as described above. One microliter of this supernatant contained approximately 625 nick closing units of activity.

The T. aquaticus ligase preparation described in the preceding examples, as well as commercially available T4 ligase, were shown to contain approximately 125 nick closing units per microliter. Thus, from 1 liter of E. coli cells overproducing T. aquaticus ligase, the process according to the present invention has purified approximately (800×125) 100,000 nick closing units of enzyme.

The thermophilic ligase prepared according to the preceding description has a number of valuable properties which makes it especially useful as an assay that both amplifies DNA and allows it to discriminate a single base substitution in a DNA sequence. The single most important property of this ligase allowing for these uses is that the ligase retains activity during repeated thermal denaturation/renaturation cycles thus allowing for the amplification of DNA without necessitating repeated addition of ligase. In addition, the ligase according to the present invention will ligate oligonucleotides of a length which is sufficient to assure their uniqueness in complex genomes at or near the $T_m$ temperatures of 65° C., and will also accurately discriminate between exactly complementary and single based mismatched oligonucleotide sequences.

In the simpler of the two procedures developed as a result of cloning the thermophilic ligase DNA sequence, termed a ligase detection reaction (LDR), two oligonucleotide probes are allowed to hybridize to denatured DNA such that the 3' end of one is immediately adjacent to the 5' end of the other. The oligonucleotides are chosen to be sufficiently long (20 to 25 nucleotides) such that each will preferentially hybridize to its unique position in the human genome. A thermophilic ligase can then form a covalent phosphodiester bond between the two oligonucleotides, provided that the nucleotides at the junction are perfectly complementary to the target. The specificity of this nick-closing reaction is particularly enhanced by virtue of performing the ligation at or near the $T_m$ of the two oligonucleotides for their target. Thus, a single base mismatch at the junction not only forms an imperfect double helix, but also destabilizes the hybrid at the higher temperature. Consequently, thermophilic ligase will efficiently link correctly base paired oligonucleotides and give near zero background ligation in the presence of the imperfectly matched sequences. Using LDR, the amount of product obtained in the ligation reaction can be increased in a linear fashion by repeated thermal cycling.

Figure 2:
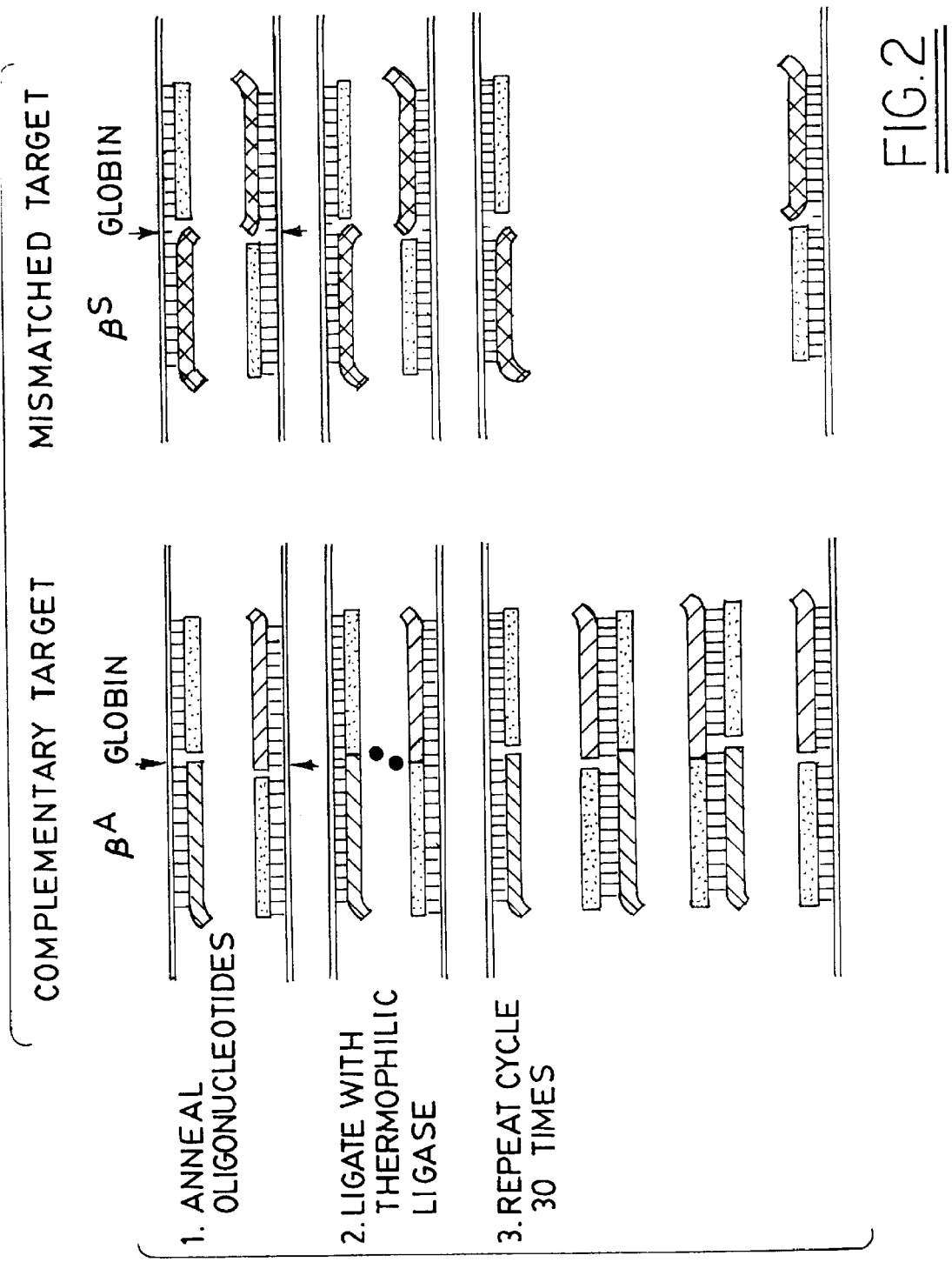
FIG. 2 is a flow chart of the Ligase Chain Reaction (LCR) according to the present invention.

In the thermophilic ligase chain reaction according to the present invention, both strands serve as targets for oligonucleotide hybridization. By using an additional two oligonucleotides complementary to the opposite strand, the ligation products of one cycle become the targets for the next cycle of ligation as generally depicted in FIG. 2. For each adjacent oligonucleotide pair, the diagnostic nucleotide is on the 3' side of the junction. Thus, aberrant target independent ligation of complementary oligonucleotides is avoided by use of temperatures near the Tm, and by taking advantage or the poor ligation efficiency of single base 3' overhangs. Using ligase chain reaction, the amount of product can be increased in an exponential fashion by repeated thermal cycling.

In order to test the potential of the thermophilic ligase chain reaction (LCR), the gene encoding human β globin was selected as an initial model system to test the technique of the present invention. Previous work has determined that the normal $β^A$ allele and sickle $β^S$ allele differ by a single A→T transversion of the second nucleotide in the sixth codon of the β globin gene, changing a glutamic acid residue into a valine in the hemoglobin β chain according to the following Table I:

TABLE 1

| Oligonucleotide | Sequence |
|---|---|
| 103 (SEQ. ID. No. 13) | GTTTTT C ATG GTG CAC CTG ACG CCT GG |
| 102 (SEQ. ID. No. 14) | GTTT C ATG GTG CAC CTG ACG CCT CT |

TABLE 1-continued

| Oligonucleotide | Sequence |
|---|---|
| 101 (SEQ. ID. No. 15) | GT C ATG GTG CAC CTG ACG CCT CA |
| 107 (SEQ. ID. No. 16) | G GAG AAG TCT GCC GTT ACT GCC |
| $\beta^A$ Globin (SEQ. ID. No. 17) | GACACC ATG GTG CAC CTG ACT CCT GAG GAG AAG TCT GCC GTT ACT GCC CTG (5'-3') |
| (SEQ. ID No. 18) | CTGTGG TAC CAC GTG GAC TGA GGA CTC CTC TTC AGA CGG CAA TGA CCG GAC (3'-5') |
| 109 (SEQ. ID. No. 19) | TGG TAC CAC GTG GAC TGA GGA C |
| 104 (SEQ. ID. No. 20) | TC CTC TTC AGA CGG CAA TGA CG TC |
| 105 (SEQ. ID. No. 21) | AC CTC TTC AGA CGG CAA TCG CG TTTC |
| 106 (SEQ. ID. No. 22) | CC CTC TTC AGA CGG CAA TCG CG TTTTTC |
| $\beta^A$ Globin (SEQ. ID. No. 23) | Met Val His Leu Thr Pro Glu Glu Lys Ser Ala Val Thr Ala Leu |
| $\beta^S$ Globin (SEQ. ID. No. 24) | Met Val His Leu Thr Pro Val Glu Lys Ser Ala Val Thr Ala Leu |

In the following continuation of Table I, presents the oligonucleotide sequences listed in the preceding portion in their conventional 5'→3' orientation:

| Sequence no. | Sequence 5' ---> 3' | size (mer) | Tm (°C.) |
|---|---|---|---|
| 101 (SEQ. ID. No. 13) | GT C ATG GTG CAC CTG ACT CCT GA | 23 | 66 |
| 102 (SEQ. ID. No. 14) | GTTT C ATG GTG CAC CTG ACT CCT GT | 25 | 66 |
| 103 (SEQ. ID. No. 15) | GTTTTT C ATG GTG CAC CTG ACT CCT GG | 27 | 64 |
| 104 (SEQ. ID. No. 20) | CT GC AGT AAC GGC AGA CTT CTC CT | 24 | 68 |
| 105 (SEQ. ID. No. 21) | CTTT GC AGT AAC GGC AGA CTT CTC CA | 26 | 68 |
| 106 (SEQ. ID. No. 22) | CTTTTT GC AGT AAC GGC AGA CTT CTC CC | 28 | 66 |
| 107 (SEQ. ID. No. 16) | G GAG AAG TCT GCC GTT ACT GCC | 22 | 70 |
| 109 (SEQ. ID. No. 19) | C AGG AGT CAG GTG CAC CAT GGT | 22 | 70 |

Oligonucleotides containing the 3' nucleotide unique to each allele were synthesized with different length 5' tails (see Table I). Upon ligation to the invariant $^{32}$P radiolabelled adjacent oligonucleotide, the individual products could be separated on a polyacrylamide denaturing gel and detected by autoradiography. Based upon these initial findings with autoradiography, subsequent assays were preformed using an automated, non-radioactive detection scheme in which the allele specific oligonucleotides were 5'-biotinylated for capture, and the invariant oligonucleotides 3'-tailed with digoxygenin. The label was then visualized in an ELISA format using anti-digoxigenin conjugated to alkaline phosphatase, and a colorimetric substrate for the enzyme.

As depicted in Table I, the nucleotide sequence and corresponding translated sequence of the oligonucleotides used in detecting $\beta^A$ and $\beta^S$ globin genes are depicted. Oligonucleotides 101 and 104 detect the $\beta^A$ target, while 102 and 105 detect the $\beta^S$ target when ligated to labelled oligonucleotides 107 and 104, respectively. Oligonucleotides 103 and 106 were designed to assay the efficiency of ligation of G:T or G:A and C:A or C:T mismatches using $\beta^A$ or $\beta^S$ globin gene targets respectively. Oligonucleotides were designed with slightly different length tails to facilitate discrimination of various products when separated on a denaturing polyacrylamide gel. The tails which were not complementary to the target sequence, may be considered as being "reporter groups" for the individual sequence. Consequently, ligation of oligonucleotides 101, 102, or 103 to 107 gives lengths of 45, 47, or 49 nucleotides, respectively. For the complementary strand, ligation of oligonucleotides 104, 105, or 106 to 109 gives lengths of 46, 48, or 50 nucleotides, respectively. The oligonucleotides were also designed to have calculated $T_m$ values of 66 to 70° C., which is just at or slightly above the ligation temperature.

In order to detect the ligation products, oligonucleotides 107 and 109 were 5'-end labelled with $^{32}$P using T4 polynucleotide kinase and $-^{32}$P according to the following example.

EXAMPLE VIII (Radioactive Labelling)

Oligonucleotide 107 (0.1 μg) was 5' end labelled in 20 μl 30 mM Tris HCl buffer at pH 8.0 containing 20 mM Tricine, 10 mM MgCl$_2$, 0.5 mM EDTA, 5 mM dithiothreitol, and 400

μCi of [$^{32}$P]ATP, by the addition of 15 units of T4 polynucleotide kinase. After incubation at 37° C. for 45 min, unlabelled ATP was added to 1 mM, and incubation was continued an additional 2 min at 37° C. The reaction was terminated by the addition of 0.5 μl 0.5 M EDTA, and kinase heat inactivated at 65° C. for 10 min. Unincorporated $^{32}$P label was removed by chromatography with Sephadex G-25 pre-equilibrated with TE buffer. Specific activity ranged from 7×10$^8$ to 10×10$^8$ cpm/μg of oligonucleotide.

Figure 3:
FIG. 3 is an autoradiogram demonstrating the specificity of *T. aquaticus* thermophilic ligase under both LDR and LCR amplification conditions according to the present invention.

The specificity of the *T. aquaticus* thermophilic ligase according to the present invention for complementary vs. mismatched target was compared under both LDR and LCR conditions (see FIG. 3 and the following Table II). In the LDR series, two adjacent oligonucleotides were incubated with denatured target DNA and ligase, where the last nucleotide of the unlabelled oligonucleotide was either complemented or mismatched the target DNA. The oligonucleotides were designed with slightly different length tails to facilitate discrimination of various products by allowing them to be separated on a denaturing gel. Consequently, as disclosed earlier, ligation of ligonucleotide 101 (β$^A$ allele), 102 (β$^S$ allele), or 103 to labelled 107 gives lengths of 45, 47 or 49 nucleotides, respectively. For the complementary strand, ligation of oligonucleotides 104 (β$^A$ allele), 105 (β$^S$ allele), or 106 to labelled 109 gives lengths of 46, 48 or 50 nucleotides, respectively. The oligonucleotides were also designed to have a calculated T$_m$ values of 66° C. to 70° C., that is just at or slightly above the ligation temperature. Thus, the specificity of ligating two oligonucleotides hybridized to target DNA with perfect complementarity (A:T) could be directly compared to each possible mismatch (A:A, T:T, G:A, G:T, C:A, or C:T). The methodology for determining specificity of ligation of these oligonucleotides in the presence of β$^A$ or β$^S$ globin gene target was determined as in the following example:

EXAMPLE IX (Determination of Specificity of Thermophilic Ligase)

Labelled oligonucleotide (200,000 cpm; 0.28 ng; 40 fmoles) and unlabelled oligonucleotide (0.27 ng; 40 fmoles) were incubated in the presence of target DNA (1 fmole=6× 10$^8$ molecules Taq I digested β$^A$ or β$^S$ globin plasmid) in 10 μl 20 mM Tris HCl buffer at pH 7.6 and containing 100 mM KCl, 10 mM MgCl$_2$, 1 mM EDTA, 10 mM NAD, 10 mM dithiothreitol, 4 μg Salmon sperm DNA, and 15 nick-closing units of the thermophilic ligase, and overlaid with a drop of mineral oil. The reactions were incubated at 94° C. for 1 min followed by 65° C. for 4 min, and this cycle was repeated between 5 and 30 times. The reactions were terminated by the addition of 8 μl formamide containing EDTA (10 mM), xylene cyanol (0.2%), and bromphenol blue (0.2%). Samples (4 μg) were denatured by boiling for 3 min prior to loading (40,000 cpm/lane) into the gel.

Products were separated by electrophoresis in which samples were loaded in groups of eight, run into the gel, and then the next set loaded, thereby accounting for the slightly slower mobility of the bands on the right side of the autoradiogram of FIG. 3. Electrophoresis was in a 10% polyacrylamide gel containing 7 M urea in a buffer of 100 mM Tris borate pH 8.9 and 1 mM EDTA, for 2 hrs at 60 W constant power.

After removing the urea by soaking for 10 min in 10% acetic acid followed by a second soak of 5 min in water, the gels were dried onto Whatman 3 mm paper and autoradiographed overnight at −70° C. on Kodak XAR-5 film (with or without Du Pont Cronex lighting plus intensifying screen). Bands from 20 cycles were excised from the gels and assayed for radioactivity. The results are given in Table II.

TABLE II

Quantitation of complementary and mismatched LDR and LCR bands from 20 cycle LDR and 30 cycle LCR experiments described in Example IX and depicted in FIG. 3 were excised from gels and assayed for radioactivity. Percentage product formed = cpm in product band/cpm in starting oligonucleotide band. Percentage mismatched/complementary = cpm in band of mismatched oligonucleotides/cpm in band of complementary oligonucleotide using the same target DNA, and gives an indication of the noise to signal ratio. LDR amplification was performed using 6 × 10$^8$ target molecules or 1 femtomole; LCR amplification was performed using 6 × 10$^6$ target molecules or 10 attomoles.

|  | Oligo base: target base | Product formed (%) | mismatched/ complementary (%) |
|---|---|---|---|
| LDR |  |  |  |
|  | A:T | 21.5 |  |
|  | T:A | 13.2 |  |
|  | T:A | 17.9 |  |
|  | A:T | 12.4 |  |
|  | A:A | <0.1 | <0.4 |
|  | T:T | 0.12 | 0.7 |
|  | T:T | 0.16 | 1.0 |
|  | A:A | <0.1 | <0.4 |
|  | G:T | 0.30 | 1.4 |
|  | C:T | <0.1 | <0.4 |
|  | G:A | <0.1 | <0.4 |
|  | C:A | <0.1 | <0.4 |
| LCR |  |  |  |
|  | A:T, T:A | 41.4 |  |
|  | T:A, A:T | 10.4 |  |
|  | A:A, T:T | 0.45 | 1.1 |
|  | T:T, A:A | <0.05 | <0.2 |
|  | G:T, C:A | 0.51 | 1.3 |
|  | G:A, C:T | <0.05 | <0.2 |

Thus, the thermophilic *T. aquaticus* ligase was shown to discriminate complementary from mismatched oligonucleotide sequences for all possible mismatched base pairs in LDR assays. Under both competition and individual ligation experiments (at varying salt concentrations), the worst case mismatch ligations were 1.5 to 1.0% (see Table II, G:T and T:T), while others were 0.4% to <0.1% (see Table II, A:A, C:T, G:A and C:A) of the products formed with complementary base pairs (A:T). This is substantially better than reported (using radioactive detection) for the mesophilic T4 ligase of *E. coli* [see Gene 76:245 (1989)].

In the LCR amplification/detection series of experiments, two adjacent oligonucleotides were incubated with denatured target DNA and ligase, as well as with the complementary set of oligonucleotides. Under these conditions, the 3' nucleotide of the unlabelled diagnostic oligonucleotide either complemented or mismatched the target DNA, but always complemented its unlabelled counterpart, i.e. A:T for 101 and 104, T:A for 102 and 105, and G:C for 103 and 106. Thus, an initial "incorrect" ligation of a mismatched oligonucleotide would subsequently be amplified with the same efficiency as a correct ligation. Samples contained pairs of unlabelled oligonucleotides (β$^A$ allele specific 101 and 104, β$^S$ allele specific 102 and 105, or 103 and 106) with the complementary and adjacent pairs of labelled oligonucleotides, 107 and 109. These labelled and unlabelled oligonucleotides were incubated in the presence of ligase and 10 attomoles of target DNA (100 fold less target DNA than for LDR) for 20 or 30 cycles as in Example IX,. The resulting bands are depicted in the left portion of FIG. 3 and the lower half of Table II.

As can be seen in FIG. 3 and Table II, the thermophilic ligase according to the present invention was capable of discriminating complementary from mismatched oligonucleotide sequences for all possible mismatched base pairs in LCR assays. Under both competition and individual ligation experiments the worse case mismatch ligations were from 1.3% to 0.6% (G:T, C:A and A:A, T:T), while others were <0.2% (T:T, A:A and G:A, C:T) of the products formed with complementary base pairs (A:T, T:A). LCR, using thermophilic ligase according to the present invention, is thus the only method which can both amplify and detect single base mismatches with high signal to noise ratios [see Genomics 4:560 (1989)]. Thus, by utilizing LCR one can detect the difference between a single base mismatch such as occurs between $\beta^A$ and $\beta^S$, and use the results of this assay as a diagnostic for the normal, the carrier, or the diseased patient.

When the entire set of experiments described above were repeated using buffer containing 150 mM instead of 100 mM KCl, the results were essentially the same as in FIG. 3 and tabulated in Table II, with ligation of mismatch oligonucleotides for LDR ranging from 0.6% to <0.3% and for LCR ranging from 1.7% to <0.3% of the exactly complementary products.. Thus, the exquisite discrimination between matched and mismatched oligonucleotides appears not to be critically dependent upon salt conditions.

Alternatively, a different procedure based on phosphatase may also be used. The LCR or LDR reaction may be performed in a 10 µl volume under mineral oil. To this is added 50 µl of 10 mM Tris HCl pH 7.6 containing 0.5 units of Bacterial Alkaline Phosphatase (BAP), and 10 mM $MgCl_2$, and the incubation continued at 65° C. for 2 hrs (note that the ligase enzyme is not killed under these conditions). The 5' end label on an oligonucleotide that has become covalently linked is no longer susceptible to BAP. Ligated product is separated from monophosphate by the addition of 20 µl of 10 mg/ml sonicated salmon sperm DNA as a carrier and precipitated with 20 µl of 50% TCA. After centrifugation for 5 min at 12,000 rpm, the supernatant is removed, and the ration of pellet to pellet + supernatant gives the percentage of product formed. A similar assay has been used with Taq I endonuclease, and the experimental error for positive and negative controls is around 1–2%.

Use of the thermophilic ligase according to the present invention obviates the need to carefully titrate both salt and enzyme concentration as required for mesophilic ligases. The data from this series of experiments is tabulated in the following Table Ill.

TABLE III

Quantitation of complementary and mismatched LDR and LCR bands, at 100 and 150 mM KCl concentrations, from 20 cycle LDR and 30 cycle LCR experiments described in Example IX and depicted in FIG. 3. LDR amplification was performed using 6 × $10^8$ target molecules or 1 femtomole; LCR amplification was performed using 6 × $10^6$ target molecules or 10 attomoles. The mismatched/complementary gives an indication of the noise to signal ratio.

| Oligo base: | Product formed (%) [KCl] (mM) | | mismatched/ complementary (%) [KCl] (mM) | |
|---|---|---|---|---|
| target base | 100 | 150 | 100 | 150 |
| LDR | | | | |
| A:T | 21.5 | 23.2 | | |
| T:A | 13.2 | 17.2 | | |
| T:A | 17.9 | 12.8 | | |
| A:T | 12.4 | 11.7 | | |
| A:A | <0.1 | <0.2 | <0.4 | <0.3 |
| T:T | 0.12 | 0.21 | 0.7 | 0.3 |

TABLE III-continued

Quantitation of complementary and mismatched LDR and LCR bands, at 100 and 150 mM KCl concentrations, from 20 cycle LDR and 30 cycle LCR experiments described in Example IX and depicted in FIG. 3. LDR amplification was performed using 6 × $10^8$ target molecules or 1 femtomole; LCR amplification was performed using 6 × $10^6$ target molecules or 10 attomoles. The mismatched/complementary gives an indication of the noise to signal ratio.

| Oligo base: | Product formed (%) [KCl] (mM) | | mismatched/ complementary (%) [KCl] (mM) | |
|---|---|---|---|---|
| target base | 100 | 150 | 100 | 150 |
| T:T | 0.16 | 0.30 | 1.0 | 0.6 |
| A:A | <0.1 | <0.2 | <0.4 | <0.3 |
| G:T | 0.30 | 0.25 | 1.4 | 0.4 |
| C:T | <0.1 | <0.2 | <0.4 | <0.3 |
| G:A | <0.1 | 0.25 | <0.4 | 0.4 |
| C:A | <0.1 | 0.20 | <0.4 | 0.3 |
| LCR | | | | |
| A:T, T:A | 41.4 | 14.2 | | |
| T:A, A:T | 10.4 | 18.5 | | |
| A:A, T:T | 0.45 | 0.09 | 1.1 | 0.6 |
| T:T, A:A | <0.05 | <0.05 | <0.2 | 0.3 |
| G:T, C:A | 0.51 | 0.24 | 1.3 | 1.7 |
| G:A, C:T | <0.05 | <0.1 | <0.2 | <0.7 |

LCR and LDR specificity was tested using both $\beta^A$ and $\beta^S$ specific oligonucleotides in direct competition for ligation to the invarient labelled oligonucleotides. Using target DNA ($\beta^A$, $\beta^S$, and an equimolar ratio of $\beta^A$ and $\beta_S$) ranging from 1 femtomole to 1 attomole, thermophilic ligase specifically formed the correct product(s) in each case; no background incorrect ligation product was observed when only one target allele was present). However, the efficiency of forming the $\beta^S$ specific products is somewhat less than forming the $\beta^A$ products, and after 20 cycles of amplification, the $\beta^S$ specific products were approximately one-third of the $\beta^A$ specific products as quantitated by assaying excised products for radioactivity. Hence a direct competition assay, wherein two oligonucleotides are differentially labelled (for example with fluorescent groups) to quantitate the relative initial concentrations of each target sequence allele will require careful titrations for each allele.

Figure 4:
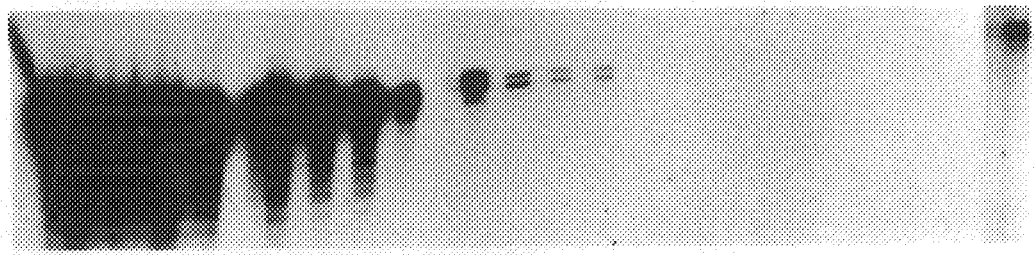
FIG. 4 is an autoradiogram demonstrating LCR amplification at different target concentrations.

The specificity of LCR DNA amplification with sub-attomole quantities of target DNA was also examined. The extent of LCR DNA amplification was determined in the presence of target DNA ranging from 100 attomoles (6×$10^7$ molecules) to less than one molecule per tube. Reactions were incubated for 20 or 30 cycles, and products separated and quantitated as depicted in FIG. 4 and the following table IV.

TABLE IV

Quantitation of LCR amplification. Bands from 30 cycle LCR experiments were excised from the gels and assayed for radioactivity. At higher target concentration, DNA amplification was essentially complete after 20 cycles; slightly imprecise excision of 30 cycle bands from this portion of the gel probably accounts for product formed values in excess of 100%. Percentage product formed = cpm in product band/cpm in starting oligonucleotide band; Amplification = No. of product molecules formed/No. of target molecules

| Target Molecules | Product formed (%) | Amplification |
|---|---|---|
| 6 × $10^7$ | 134 | |
| 2 × $10^7$ | 96 | |
| 6 × $10^6$ | 107 | |

TABLE IV-continued

Quantitation of LCR amplification. Bands from 30 cycle LCR experiments were excised from the gels and assayed for radioactivity. At higher target concentration, DNA amplification was essentially complete after 20 cycles; slightly imprecise excision of 30 cycle bands from this portion of the gel probably accounts for product formed values in excess of 100%. Percentage product formed = cpm in product band/cpm in starting oligonucleotide band; Amplification = No. of product molecules formed/No. of target molecules

| Target Molecules | Product formed (%) | Amplification |
|---|---|---|
| $2 \times 10^6$ | 78 | |
| $6 \times 10^5$ | 85 | |
| $2 \times 10^5$ | 48 | $5.8 \times 10^4$ |
| $6 \times 10^4$ | 25 | $1.0 \times 10^5$ |
| $2 \times 10^4$ | 4.5 | $5.4 \times 10^4$ |
| $6 \times 10^3$ | 2.3 | $9.2 \times 10^4$ |
| $2 \times 10^3$ | 0.36 | $4.3 \times 10^4$ |
| $6 \times 10^2$ | 0.18 | $7.2 \times 10^4$ |
| $2 \times 10^2$ | 0.14 | $1.7 \times 10^5$ |
| 60 | <0.05 | |
| 20 | <0.05 | |
| 6 | <0.05 | |
| 2 | <0.05 | |
| 0 | <0.05 | |

In the absence of target, no background signal was detected carrier salmon sperm DNA (4 μg) was present as seen in FIG. 4. At higher initial target concentrations, DNA amplification was essentially complete after 20 cycles, while at lower initial target concentrations substantially more product is formed with additional amplification cycles. Under these conditions, 200 molecules of initial target DNA could easily be detected after 30 cycles.

The thermostable nature of the enzyme is readily apparent in FIG. 4. By comparing the amount of product formed after 20 cycles to that formed after 30 cycles, it is apparent that at the lower target DNA concentrations additional product is formed after more cycles (see especially $2 \times 10^4$ to $2 \times 10^2$ target DNA molecules). In other words, the enzyme still has activity after 20 cycles of 94°0 C. for 1 minute followed by 65° C. for 4 minutes.

Thus, *T. aquaticus* ligase retains the ability to catalyze formation of a phosphodiester bond between two adjacent oligonucleotides hybridized to a complementary strand of DNA at a temperature in the range of about 50° C. to about 85° C. after repeated exposure to temperatures that denature DNA, namely in the range of about 105° C. for about 0.25 minutes to about 4 minutes.

Hence, the specific amplification of a nucleic acid test substance of known nucleotide sequence using LCR requires: (1) two adjacent oligonucleotides complementary to and in molar excess of the target sequence nucleic acid, and having no mismatch to the target sequence nucleic acid at the junction of the adjacent oligonucleotides; (2) a second set of adjacent oligonucleotides complementary to the first set of adjacent oligonucleotides, complementary to and in molar excess of the target sequence nucleic acid, and having no mismatch to the target sequence nucleic acid at the junction of this second set of adjacent oligonucleotides; (3) a thermostable ligase which does not become irreversibly denatured and lose its catalytic ability when subjected to temperatures of from about 50° C. to about 105° C.; and (4) subjecting this ligase mixture to repeated temperature cycles which comprises a first temperature to denature the DNA (in a range of about 90° C. to about 105° C), and a second temperature to allow for hybridization/ligation (in a range of about 50° C. to about 85° C.). In the amplification of $\beta^A$ globin allele described above, the components were (1) oligonucleotides 101 and 107; (2) oligonucleotides 104 and 109; (3) *T. aquaticus* ligase; and (4) 30 temperature cycles of 94° C. for 1 minute followed by 65° C. for 4 minutes.

In FIG. 4, bands of 45 and 46 nucleotides correspond to ligation products of the coding and complementary $\beta^A$ globin oligonucleotides. Lower molecular weight products correspond to ligation of deletion oligonucleotides present in the initial ligation reaction. Since samples were loaded in groups of eight, the right side of the autoradiogram gives the appearance of slower migration.

To further test the ability of ligase to discriminate between complementary and mismatched oligonucleotides, an LCR experiment was performed in the presence and absence of oligonucleotides which would give G-T and C-A mismatches in accordance with the following example which not only shows DNA amplification, but also supports the thermostable nature of the enzyme found in Example IX.

EXAMPLE X

One set of experiments contained 40 fmoles each of unlabelled 101 and 104 oligonucleotides, while the second set had in addition 40 fmoles of unlabelled 103 and 106 oligonucleotides. Both sets contained 40 fmoles each of labelled 107 and 109. Labelled oligonucleotides (200,000 cpm; 0.28 ng; 40 fmoles) and unlabelled oligonucleotides (0.27 ng; 40 fmoles) were incubated in the presence of target DNA, ranging from 100 attomoles ($6 \times 10^7$ molecules) to 0.01 attomoles ($6 \times 103$ molecules) of Taq I digested $\beta^A$ or $\beta^S$ globin plasmid. Incubation was carried out in 10 μl 20 mM Tris-HCl, ph 7.6 buffer containing 100 mM $MgCl_2$, 1 mM EDTA, 10 mM NAD, 10 mM dithiothreitol, 4 μg Salmon sperm DNA, and 15 nick-closing units of *T. aquaticus* ligase, and overlaid with a drop of mineral oil. Reactions were incubated at 94° C. for 1 min followed by 65° C. for 4 min, and this cycle was repeated 20 or 30 times.

The resulting samples were electrophoresed, gel autoradiographed overnight with the aid of a Cronex intensifying screen and the bands counted. The bands from the autoradiographed gel are depicted in FIG. 4, and the quantitation of LCR amplification tabulated in the following Table V.

TABLE V

Quantitation of LCR amplification the presence or absence of mismatched competitor molecules.

| | Complementary Oligonucleotides (101, 104) | | Complementary & Mismatched Oligonucleotides (101, 104 & 103, 106) (A:T, T:A & G:T, C:A) | | |
|---|---|---|---|---|---|
| | (A:T, T:A) | | | | Mismatched/ |
| Target molecules | Product formed | Amplification | Product formed | Amplification | Complementary |
| $6 \times 10^7$ ($\beta^A$) | 114 | | 93 | | 1.0 |
| $2 \times 10^7$ | 93 | | 95 | | 1.8 |
| $6 \times 10^6$ | 102 | | 93 | | 0.5 |
| $2 \times 10^6$ | 90 | | 67 | | 0.5 |
| $6 \times 10^5$ | 51 | | 46 | | |
| $2 \times 10^5$ | 31 | $3.7 \times 10^4$ | 23 | $2.8 \times 10^4$ | |
| $6 \times 10^4$ | 17 | $6.8 \times 10^4$ | 9.3 | $3.7 \times 10^4$ | |
| $2 \times 10^4$ | 8.6 | $1.0 \times 10^5$ | 2.9 | $3.5 \times 10^4$ | |
| $6 \times 10^3$ | 3.2 | $1.3 \times 10^5$ | 0.8 | $3.4 \times 10^4$ | |
| 0 | <0.1 | | <0.1 | | |
| $6 \times 10^7$ ($\beta^S$) | 2.1 | | 1.5 | | |

At high target concentrations, sufficient mismatched product was produced to be visualized (as in FIG. 4), the quantity of mismatched product ranging from 1.8% to 0.5% of the complementary product. Use of an excess of mismatched target DNA ($\beta^S$ instead of $\beta^A$ globin DNA at $6\times10^7$ molecules per tube) gave only 2.1% and 1.5% product. The same amount of product may be formed when using three to ten thousand fold less complementary target DNA. Based upon this, the signal from correctly paired ligation products is 50 to 500 fold higher than mismatched products under competition or individual LCR ligation conditions.

At low target concentrations, the extent of DNA amplification ranged from $3.7\times10^4$ to $1.7\times10^5$ (see Tables IV and V). Assuming the efficiency of ligation is the same in each cycle, the average amplification per cycle is between 40 and 50%.

The efficiency per cycle could, of course, be potentially enhanced by altering buffer conditions, enzyme concentration, or thermal cycling times and temperatures—all within the capabilities of those skilled in the art. It has, for example, been shown that the ligation efficiency of thermophilic ligase (and other ligases) may be enhanced by altering buffer compositions, such as using NH4Cl, HEPES, polyamines such as spermidine, or polyethylene glycols [see J. Biol. Chem 259:10041 (1984), and J. Biochem. 100:123 (1986)]. Varying the amounts of each component in the currently used buffer and either supplementing or exchanging one or more components with, but not limited to, the chemical and biological components listed above, are among the methods of improving LCR that are straight forward for those skilled in the art. One skilled in the art can also easily vary the cycling times and temperatures. For example, at later time points, the majority of target present is oligonucleotide product from a previous LCR reaction. These oligonucleotides are short (preferably but not limited to 40–60 mers) and may melt more rapidly, allowing more rapid cycling. In the present invention, successful ligase chain reactions have been completed for 30 and 40 cycles under cycling conditions of 94° C. for 0.5 minutes followed by 65° C. for 2 minutes (half the time of the 1 minute at 94° C. and 4 minutes at 65° C. cycle time for the preferred ligase chain reaction conditions). Both the ligation temperature and the DNA denaturing temperatures may be varied with respect to actual degree, duration, and number of repeated cycles. Optimal conditions must maximize the amount of product formed in the presence of perfectly complementary target DNA, while minimizing the amount of incorrect product formed in the presence of mismatched target DNA or in the absence of complementary target DNA.

Utilizing these findings, a method for the detection of specific sequences of oligonucleotides in clinical samples was developed. The source of the sample may be any material or substance which comprises nucleic acid. The nucleic acid need not be a naturally occurring nucleic acid, but may be synthesized by chemical, enzymatic, or biological means and may have other than naturally occurring purines and pyrimidines. The source of the clinical sample may be cellular or non-cellular, and may be derived from such physiological media as blood, serum, plasma, breast milk, stool, pus, tissue scrapings, washings, urine, or the like. Furthermore, the sample may be associated with a set or subset of cells, such as neoplastic cells, lymphocytes (for example, T-cells or B-cells, monocytes, neutrophils, etc); may include pathogens including viruses, bacteria, mycoplasma, fungi, protozoa, etc.; may include constructs, etc. or RNA, such as messenger RNA, transfer RNA, ribosomal RNA, viruses, or the like; and it may involve structural genes, untranslated regions, regulatory regions, introns, exons, or the like. In addition, the detection may be for a wide variety of purposes such as, for example, the diagnosis of a potential or actual disease state in plant or animal species, as well as the detection of sets or subsets of pathogens, the monitoring of genetic engineering, or the like.

One such method for which the present invention may be used (and which clearly demonstrates the feasibility of direct LCR allelic detection from blood samples without the need for prior PCR amplification) is embodied, for example, in the detection of β-globin alleles in human genomic DNA. Based upon the high level of DNA amplification, the allele specific LCR detection of DNA was examined from blood collected from normal ($\beta^A\beta^A$), carrier ($\beta^A\beta^S$), and sickle cell ($\beta^S\beta^S$) individuals as more fully described in the following example:

EXAMPLE XI (detection of β-globin alleles in human genomic DNA)

Human genomic DNA was isolated from 0.5 ml whole blood [see PCR Technology, H. A. Erlich editor, Stockton Press (1989) pg 36]. Whole blood (0.5 ml) was mixed with an equal volume of lysis buffer (10 mM Tris-HCl, pH 7.6, containing 5 mM $MgCl_2$ and 0.32 M sucrose). After a brief centrifugation (1 min at 12,000 rpm in an eppendorf desktop centrifuge), the supernatant was very carefully removed, leaving 0.15 to 0.2 ml of supernatant and loosely pelleted nuclei. The pellet was resuspended with vortexing in an additional 0.5 ml lysis buffer, nuclei pelleted and the supernatant removed as above. This step was repeated three or four times until the supernatant was clear or just barely pink. After removal of the final supernatant (again leaving about 0.15 to 0.2 ml), 0.25 ml of LCR DNA Buffer containing non-ionic detergents (20 mM Tris-HCl, pH 7.6, containing 2 mM EDTA and 0.45% each of non-ionic detergents NP40 and Tween 20) was added. Any excess RNA was digested by the addition of 2 $\mu$l of 4 mg/ml heat treated RNase A for 15 min at 37° C. Any proteins were digested by the addition of 5 $\mu$l of 10 mg/ml freshly made Proteinase K and incubation at 50° C. for 1 to 2 hours. Proteinase K and RNase A were removed by sequential extractions with phenol, phenol/chloroform, chloroform, n-butanol (2x) and the nucleic acid recovered by precipitation with ethanol. Samples were boiled for 5 min prior to use in LCR assays.

Each isolated human genomic DNA was tested in two reaction mixtures, the first testing for the presence of the normal $\beta^A$ allele, and the second testing for the presence of the sickle $\beta^S$ allele. The first reaction mixture contained $\beta^A$ test oligonucleotides 101 and 104 (0.27 ng or 40 fmoles each), labelled oligonucleotides (107 and 109; 200,000 cpm (0.28 ng or 40 fmoles each), genomic DNA (corresponding to 10 $\mu$l of blood, or about $6\times10^4$ nucleated cells) in 10 $\mu$l 20 mM Tris-HCl buffer, pH 7.6, containing 100 mM KCl, 10 mM $MgCl_2$, 1 mM EDTA, 10 mM NAD, 10 mM dithiothreitol, and 15 nick-closing units of *T. aquaticus* ligase, and overlaid with a drop of mineral oil. The second reaction mixture contained $\beta^S$ test oligonucleotides 102 and 105 (0.27 ng or 40 fmoles each), labelled oligonucleotides 107 and 109 (200,000 cpm or 0.28 ng or 40 fmoles each), genomic DNA corresponding to 10 $\mu$l of blood or about $6\times10^4$ nucleated cells) in 10 $\mu$l 20 mM Tris-HCl buffer, pH 7.6 and containing 100 mM KCl, 10 mM $MgCl_2$, 1 mM EDTA, 10 mM NAD, 10 mM dithiothreitol, and 15 nick-closing units of *T. aquaticus* ligase, and overlaid with a drop of mineral oil.

Both reaction mixtures were incubated at 94° C. for 1 min followed by 65° C. for 4 min, and this cycle was repeated 20 to 30 times. Reactions were terminated by the addition of 8μl formamide containing EDTA (10 mM), xylene cyanol (0.2%), and bromphenol blue (0.2%).

Samples (4 μl) were denatured by boiling for three min prior to loading (40,000 cpm/lane). Electrophoresis was in a 10% polyacrylamide gel containing 7 M urea in a buffer of 100 mM Tris borate at ph 8.9 and 1 mM EDTA, for 2 hours at 60 Watt constant power. After removing the urea (10 min soak in 10% acetic acid, followed by 5 min soak in H$_2$O). Gels were then dried onto Whatman 3 mm paper and autoradiographed overnight at −70° C. on Kodak XAR-5 film with a DuPont Cronex intensifying screen. Ligation products of 45 and 46, or 47 and 48 nucleotides indicate the presence of the $\beta^A$ or $\beta^S$ globin gene, respectively. As noted with plasmid derived target DNA, the efficiency of ligation (and hence detection) is somewhat less for the $\beta^S$ than the $\beta^A$ specific oligonucleotides.

Figure 5:
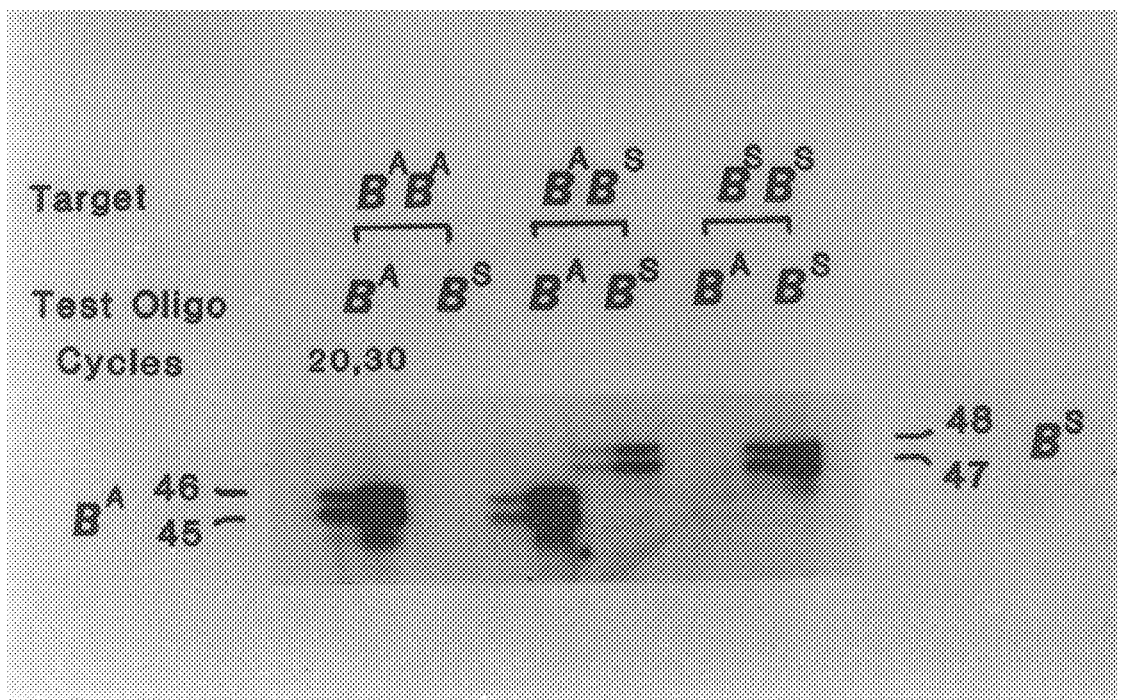
FIG. 5 is an autoradiogram demonstrating the detection of β globin alleles using human genomic DNA.

FIG. 5 is an autoradiogram showing the detection of β-globin alleles in human genomic DNA made in accordance with the proceeding example. Ligation products of 45 and 46, or 47 and 48 nucleotides indicate the presence of the $\beta^A$ or $\beta^S$ globin gene, respectively. Thus, with target DNA corresponding to 10 μl of blood, $\beta^A$ and $\beta^S$ alleles could be readily detected using allele specific LCR.

Hence, the successful detection of a biologically derived nucleic acid test substance, which has a known normal nucleotide sequence and a known possible mutation at at least one target nucleotide position in the sequence, requires (1) a first reaction mixture comprising two sets of adjacent oligonucleotides complementary to each other, complementary to the target sequence nucleic acid, wherein there is at least one mismatched base pair to the mutant target sequence nucleic acid, but not to the normal target sequence nucleic acid at the junction of the adjacent oligonucleotides; (2) a second reaction mixture comprising two sets of adjacent oligonucleotides complementary to each other, complementary to the target sequence nucleic acid, wherein there is at least one mismatched base pair to the normal target sequence DNA, but not to the mutant target sequence nucleic acid at the junction of the adjacent oligonucleotides; (3) a thermostable ligase which does not become irreversibly denatured and lose its catalytic ability when subjected to temperatures of from about 50° C. to about 105° C.; and (4) subjecting these ligase mixtures to repeated temperature cycle which comprises a first temperature to denature the DNA (in a range of about 90° C. to about 105° C.), and a second temperature to allow for hybridization/ligation (in the range of about 50° C. to about 85° C.) — this also allows adjacent oligonucleotides in each reaction mixture to become possibly covalently linked; (5) separating the test substance and any unlinked test oligonucleotides from covalently linked oligonucleotide product (if formed); and (6) detecting the presence or absence of covalently linked oligonucleotides in each reaction mixture whereby the presence of covalently linked oligonucleotide product in the first reaction mixture indicates the presence of normal target sequence and the presence of covalently linked oligonucleotide product in the second reaction mixture indicates the presence of mutant target sequence. In the detection of $\beta^A$ and $\beta^S$ globin alleles described above, the components were (1) oligonucleotides 101, 104, 107 and 109; (2) oligonucleotides 102, 105, 107 and 109; (3) T. aquaticus ligase; (4) 30 temperature cycles of 94° C. for 1 min followed by 65° C. for 4 min; (5) denaturing nucleic acids by boiling in 45% formamide and separating on a sequencing gel; and (6) autoradiographing of the gel.

This clearly demonstrates the feasibility of direct LCR allelic detection from blood samples according to the present invention without the need for PCR amplification.

As noted with plasmid derived target DNA, the efficiency of ligation (and hence detection) is somewhat less for the $\beta^S$ than the $\beta^A$ specific oligonucleotides. After 30 cycles of amplification, $\beta^S$ specific products were approximately one-third of $\beta^A$ specific products, as quantitated by assaying excised products for radioactivity. These differences may be a function of the exact nucleotide sequence at the ligation junction, or the particular oligonucleotides (with differing 5' tails) used in the LCR experiments. However, the present invention still allows for a direct competition assay where two oligonucleotides are differentially labelled (for example with fluorescent groups or, in this case, with different length tails) to determine the presence or absence of either allele in a reaction mixture. In the generalized form, the method according to the present invention allows one to assay two alleles in the same vessel, providing the sets of oligonucleotides containing at least one mismatched base pair to the mutant target sequence nucleic acid, but not to the normal target sequence nucleic acid at the junction of the adjacent oligonucleotides, are labelled with one set of labels, and the oligonucleotides containing at least one mismatched base pair to the normal target sequence nucleic acid, but not to the mutant target sequence nucleic acid at the junction of the adjacent oligonucleotides, are labelled with a different label.

Figure 6:
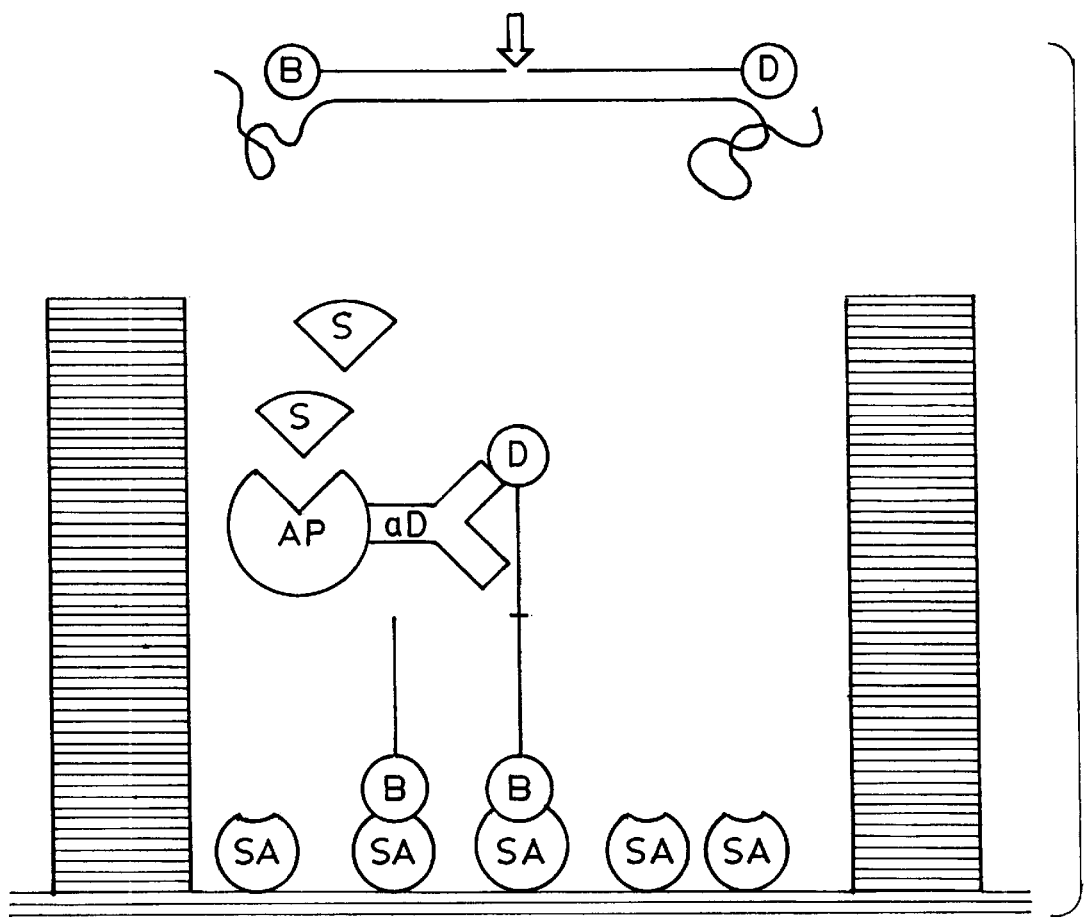
FIG. 6 is an overview of an ELISA based oligonucleotide ligation assay according to the present invention.

In a comparable non-radioactive assay, as depicted in FIG. 6, a minimum of two oligonucleotide probes are synthesized and modified for particular functions in the ligation assay. One probe contains a hook that permits the capture of the oligonucleotide following ligation. An example of such a hook is biotin which can be captured by streptavidin or avidin bound to appropriate supports. The other probe has a reporter group. Although a variety of reporter groups, both radioisotopic and non-radioactive, are available and can be used with the assay according to the present invention, such as fluorophores or luminescent moieties, the currently preferred reporter is one which may participate in an ELISA (enzyme-linked immuno sorbent assay). More specifically, FIG. 6 depicts a schematic diagram of an ELISA based oligonucleotide ligation assay in which biotinylated (B) and digoxigenin-labelled (D) oligonucleotides are hybridized with a DNA target in the presence of ligase (arrow). Biotinylated oligonucleotides are captured on streptavidin (SA) coated within the wells of microtiter plates. The wells are washed to remove unbound oligonucleotides, and alkaline phosphatase (AP) conjugated anti-digoxigenin antibodies ( D) are added to the wells. Following an incubation and wash cycle, alkaline phosphatase substrate (S) is added, and digoxigenin detected by the production of a color product.

The non-radiolabelled assay according to the present invention consists of several steps: (1) preparation of the DNA target; (2) denaturation and hybridization of the modified oligonucleotide probes; (3) ligation; (4) capture of the biotinylated probe; (5) washing to remove free nonbiotinylated oligonucleotides and target; (6) addition of alkaline phosphatase conjugated anti-digoxigenin antibodies; (7) washing to removed unbound antibody; (8) addition of alkaline phosphatase substrate; and (9) spectrophotometric analysis. The following flow chart details the general procedure (which has automated on a modified Biomek 1000 workstation instrument) by which a non-radiolabelled assay according to the present invention can be conducted:

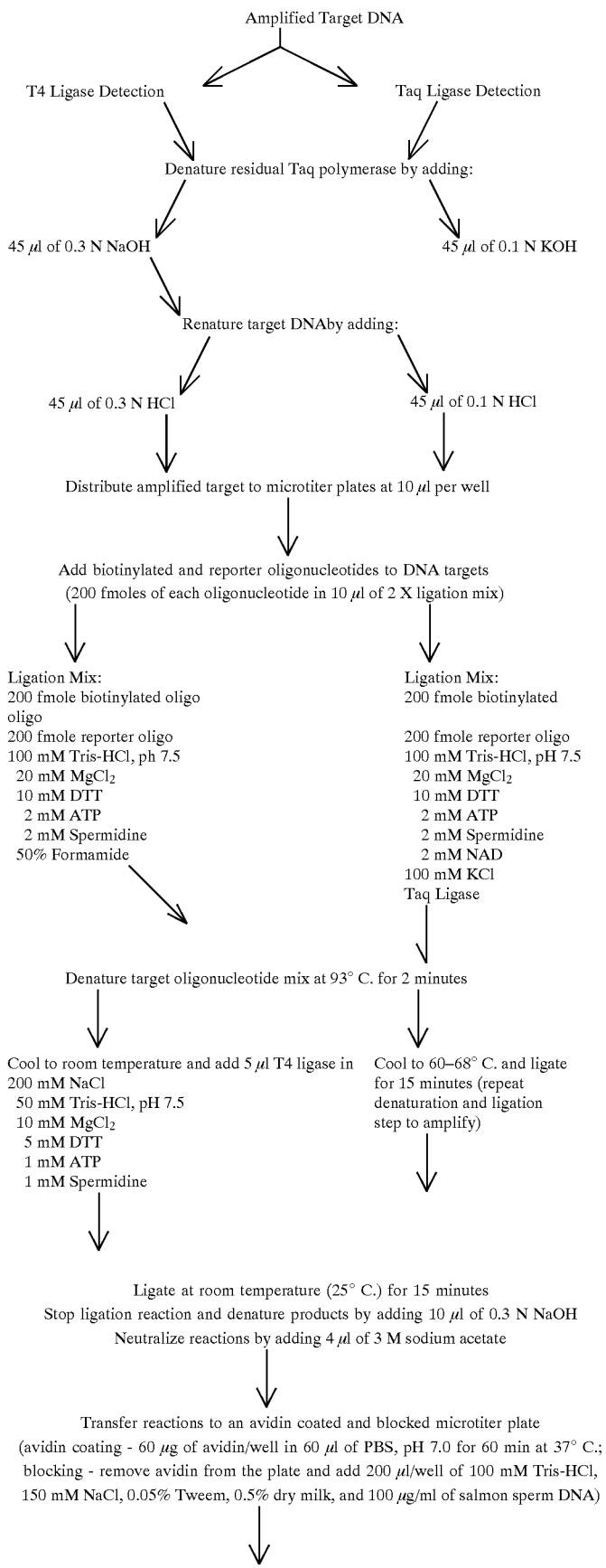

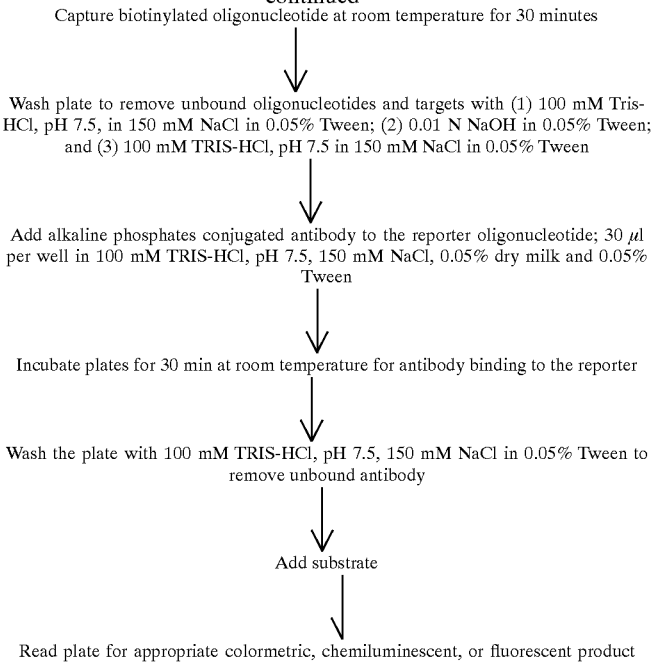

-continued

Capture biotinylated oligonucleotide at room temperature for 30 minutes

↓

Wash plate to remove unbound oligonucleotides and targets with (1) 100 mM Tris-HCl, pH 7.5, in 150 mM NaCl in 0.05% Tween; (2) 0.01 N NaOH in 0.05% Tween; and (3) 100 mM TRIS-HCl, pH 7.5 in 150 mM NaCl in 0.05% Tween

↓

Add alkaline phosphates conjugated antibody to the reporter oligonucleotide; 30 μl per well in 100 mM TRIS-HCl, pH 7.5, 150 mM NaCl, 0.05% dry milk and 0.05% Tween

↓

Incubate plates for 30 min at room temperature for antibody binding to the reporter

↓

Wash the plate with 100 mM TRIS-HCl, pH 7.5, 150 mM NaCl in 0.05% Tween to remove unbound antibody

↓

Add substrate

↓

Read plate for appropriate colormetric, chemiluminescent, or fluorescent product Genomic sequences required to begin this assay can be amplified by a number of different methods, including LCR, 3SR, and PCR. We have used PCR amplification to obtain DNA targets listed on the following Table VI for litigation assay primers:

TABLE VI (sequences of amplification primer sets)

| Target Gene | Amplification Primers |
|---|---|
| β-globin (SEQ. ID. No. 25) | CAACTTCATCCACGTTCACCTTGCC |
| (SEQ. ID. No. 26) | AGGGCAGGAGCCAGGGCTGGGG |
| alpha₁-antitrypsin (SEQ. ID. No. 27) | TCAGCCTTACAACGTGTCTCTGCTT |
| (SEQ. ID. No. 28) | GTATGGCCTCTAAAAACATGGCCCC |
| cystic fibrosis (SEQ. ID. No. 29) | CAGTGGAAGAATGGCATTCTGTT |
| (SEQ. ID. No. 30) | GGCATGCTTTGATGACGCTCTG |

DNA amplification was performed using 5 μl of DNA (2 ng/μl for genomic DNA or 5 μl of treated material from an alternative source) is mixed with a pair of primer oligonucleotides (0.5 μM each) specific for the region of DNA to be amplified in a PCR buffer containing 0.05 U/μl of Taq polymerase, 50 mM KCl, 25 mM Tris HCl buffer at pH 8.3, 10 mM MgCl$_2$, 200 μg/ml gelatin, 0.1% Triton X-100, and 1.5 mM each of dATP, dCTP, dGTP and dTTP. The sample was overlaid with 60 μl of light mineral oil, denatured at 93° C. for 5 min target, and subjected to 40 cycles consisting of 20 sec at 93° C., 40 sec at 55° C., and 1 min at 72° C.

Following temperature cycling, the sample was subjected to 10 min at 72° C. to complete extension of the DNA sample.

Oligonucleotides are synthesized and modified for particular functions in the ligation assay. The assay requires a minimum of two modified oligonucleotides. One oligonucleotide has a hook that permits capture of the oligonucleotide following ligation. An example of this is a biotinylated oligonucleotide which can be captured on streptavidin or avidin supports. The other oligonucleotide has a reporter group which, in the case of a fluorophore reporter, multiple reporters with different emission spectra could easily be incorporated into a single assay.

For an ELISA based system, probes which discriminate allelic forms of a gene are synthesized with a 5' biotin group. Reporter probes are enzymatically or chemically 5'-phosphorylated and labelled with the hapten digoxigenin. The hapten is added to the 3' end of the reporter probe by tailing 500 pM of oligonucleotide at 37° C. for 1 hour in 10 mM potassium cacodylate, pH 7.0, 1 mM CoCl$_2$, 0.1 mM DTT, 5 nM of digoxigenin dUTP, 0.05 μM of dATP, and 100 units of the enzyme terminal transferase in a total volume of 20 μl. After labelling, 2 μl of 3 M sodium acetate and 1 μl of yeast t-RNA (1 mg/ml) and 60 μl of 95% ethanol is added. The oligonucleotide is precipitated at 4° C. for 5 min and then collected by centrifugation at 6500×g for 5 minutes. The pellet is resuspended in 20 μl of distilled water and the process repeated. This precipitation removes unconjugated excess digoxigenin from the labelled probe. Example of oligonucleotides which discriminate alleles for three pathologic states are given in the following table VII:

TABLE VII (sequences of example oligonucleotides for ELISA detection)

| Target Gene | Form of Gene Detected | Biotinylated Primer | Labelled (L) Primer |
|---|---|---|---|
| β-globin (SEQ. ID. No. 31) | β$^A$ | B1-ATGGTGCACCTGACTCCTGA | |
| (SEQ. ID. NO. 32) | | | GGAGAAGTCTGCCGTTACTG |
| (SEQ. ID. No. 33) | β$^S$ | B2-ATGGTGCACCTGACTCCTGT | |

TABLE VII-continued (sequences of example oligonucleotides for ELISA detection)

| Target Gene | Form of Gene Detected | Biotinylated Primer | Labelled (L) Primer |
|---|---|---|---|
| alpha$_1$ (SEQ. ID. No. 34) anti-trypsin (SEQ. ID. No. 35) | M | B1-GGCTGTGCTGACCATCGACG | AGAAAGGGACTGAAGCTGCT |
| (SEQ. ID. No. 36) | Z | B2-GGCTGTGCTGACCATCGACA | |
| cystic (SEQ. ID. No. 37) fibrosis (SEQ. ID. No. 38) | non-508 | B1-ATTAAAGAAAATATCATCTT | TGGTGTTTCCTATGATGAAT |
| (SEQ. ID. No. 39) | 508 | B2-ACCATTAAAGAAAATATCAT | |

Utilizing the procedure contained in the previous flow chart, a number of experiments were run and, after color development, data were obtained spectrometrically at a wavelength of 490 mN. Typical results for such tests have been tabulated in the following TABLE VIII

TABLE VIII (spectrophotometric data from automated ligation reactions using Taq ligase)

| | Ligation Primer Mix | |
|---|---|---|
| Amplified Genomic DNA Target From: | B1 + L | B2 + L |
| β-globin | | |
| β$^A$ | 1.27 ± 0.06 | 0.01 ± 0.01 |
| β$^S$ | 0.04 ± 0.03 | 1.85 ± 0.03 |
| alpha$_1$-antitrypsin | | |
| M | 1.85 ± 0.15 | 0.03 ± 0.01 |
| Z | 0.03 ± 0.03 | 1.47 ± 0.07 |
| cystic fibrosis: | | |
| non-508 | 1.33 ± 0.20 | 0.02 ± 0.01 |
| 508 | 0.01 ± 0.01 | 1.66 ± 0.16 |

Comparable levels of detection were achieved with either T4 or Taq ligase. In addition, a number of ligation reactions have been performed for several other disease associated polymorphisms with comparable results. Additionally, eight different polymorphisms in the human T cell receptor loci have been examined with similar detection results. The present invention, therefore, appears to be generally applicable in the analysis of DNA polymorphisms consisting of single base substitutions, DNA deletion or insertions, or DNA translations.

In addition, a number of alkaline phosphatase substrates can be employed in the ELISA assay of the present invention including sensitive chemiluminescent substrates (10 attomole detection). The format of the assay is easily adapted to other reporter formats such as fluoropores which can be read in the appropriate microtiter format. Incorporation of the appropriate fluorophore format would, for example, permit multiplex analysis by ligation. In this scheme, oligonucleotides discriminating different alleles and/or different genes could be evaluated in a single assay. Furthermore, it is also possible that tandem ligation assays (ligation of oligonucleotides in chains) could be employed to assess closely spaced DNA polymorphisms such as those which exist in the major histocompatibility complex genes. Such modifications to the assay specifically depicted above are considered to be well within the scope of the present invention The present invention can be used in a wide variety of DNA diagnostic screening. For example, and not intending to limit the scope of the present invention, such DNA diagnostic screens may include those according to the following summary:

A - INFECTIOUS DISEASES
  1. Viral Diseases: HIV, EBV, HPV, HSV, CMV, Hepatitis (non-A, non-B)
    (i) blood and tissue screening
    (ii) rapid identification
    (iii) distinguish chronic infection from past exposure
    (iv) distinguish resistant strains in mixed infection
  2. Bacterial Diseases: Mycobacteria, Syphilis, Clamydia, Legionella, Campylobacter; Pneumonocystis, Lysteria, Lyme, Leprosy
    (i) rapid identification of slow growing microbes
    (ii) identification in immuno-deficient patients
    (iii) testing food for contamination
  3. Parasitic Diseases: Malaria, Trypanosomes, Leishmania
    (i) rapid identification of "third world" blood diseases
    (ii) screening travelers and armed forces
B - GENETIC DISEASES
  1. Single Allele Diseases: Cystic Fibrosis, Duchenne's muscular dystrophy, Sickle Cell Anemia, β-thalasemia, Haemophilia A, Gaucher, Tay-Sachs, Alsheimer's, Neurofibromatosis
  2. Cancer: Retinoblastoma, Wilms tumor, Colon, Breast, Oncogenes, Tumor supressors
  3. Multiple Allele Diseases: Coronary heart disease, Diabetes, High blood pressure, Schizophrenia, Manic-depression, Alcohol abuse
    (i) predisposition to disease
    (ii) preventive medicine, exercise, diet
    (iii) genetic screening and counseling
    (iv) gene therapy.
C - GENETIC IDENTIFICATION
  1. Humans: HLA typing, forensics
    (i) tissue transplantation
    (ii) genetic linkage analysis
    (iii) human genome program
    (iv) positive identification of missing children
  2. Animals: Horses, Dairy cows, Cattle, Domestic pets
    (i) pure genetic characteristics
    (ii) confirm breeding lineage
    (iii) positive identification of animals
  3. Plants: Seed Stock
    (i) assure genetic diversity
    (ii) identify strains resistant to drought and disease.

Thus, while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and a process of making and using it in such full, clear, concise and exact terms so as to enable any person skilled in the art to which it pertains, or with which it is most nearly connected, to make and use the same;

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 2111 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
TCGGAATAGG  GGATGCGCCC  CTAGTCCAAG  GGAAAGTATA  GCCCAAGGTA  CACTAGGCC      60
ATGACCCTGG  AAGAGGCGAG  GAAGCGGGTA  AACGAGTTAC  GGGACCTCAT  CCGCTACCAC    120
AACTACCGCT  ACTACGTCCT  GGCGGACCCG  GAGATCTCCG  ACGCCGAGTA  CGACCGGCTT    180
CTTAGGGAGC  TCAAGGAGCT  TGAGGAGCGC  TTCCCCGAGC  TCAAAAGCCC  GGACTCCCCC    240
ACCCTTCAGG  TGGGGGCGAG  GCCTTTGGAG  GCCACCTTCC  GCCCCGTCCG  CCACCCCACC    300
CGCATGTACT  CCTTGGACAA  CGCCTTTAAC  CTTGACGAGC  TCAAGGCCTT  TGAGGAGCGG    360
ATAGAACGGG  CCCTGGGGCG  GAAGGGCCCC  TTCGCCTACA  CCGTGGAGCA  CAAGGTGGAC    420
GGGCTTTCCG  TGAACCTCTA  CTACGAGGAG  GGGGTCCTGG  TCTACGGGGC  CACCGCCGGG    480
GACGGGGAGG  TGGGGGAGGA  GGTCACCCAG  AACCTCCTCA  CCATCCCCAC  CATCCCGAGG    540
AGGCTCAAGG  GGGTGCCGGA  GCGCCTCGAG  GTCCGGGGGG  AGGTCTACAT  GCCCATAGAG    600
GCCTTCCTCC  GGCTCAACGA  GGAGCTGGAG  GAGCGGGGGG  AGAGGATCTT  CAAAAACCCT    660
AGGAATGCGG  CGGCGGGTTC  CTTAAGGCAA  AAAGACCCCC  GCATCACCGC  CAAGCGGGGC    720
CTCAGGGCCA  CCTTCTACGC  CTTAGGGCTT  GGGCTGGAGG  AGGTGGAGAG  GGAAGGGGTG    780
GCGACCCAGT  TTGCCCTCCT  CCACTGGCTC  AAGGAAAAAG  GCTTCCCCGT  GGAGCACGGC    840
TACGCCCGGG  CCGTGGGGGC  GGAAGGGGTG  GAGGCGGTCT  ACCAGGACTG  GCTCAAGAAG    900
CGGCGGGCGC  TTCCCTTTGA  GGCGGACGGG  GTGGTGGTGA  AGCTGGACGA  GCTTGCCCTT    960
TGGCGGGAGC  TCGGCTACAC  CGCCCGCGCC  CCCCGGTTCG  CCATCGCCTA  CAAGTTCCCC   1020
GCCGAGGAGA  AGGAGACCCG  GCTTTTGGAC  GTGGTCTTCC  AGGTGGGGCG  CACCGGGCGG   1080
GTGACCCCCG  TGGGGATCCT  CGAGCCCGTC  TTCCTAGAGG  GCAGCGAGGT  CTCCGGGTC    1140
ACCCTGCACA  ACGAGAGCTA  CATAGAGGAG  TTGGACATCC  GCATCGGGGA  CTGGGTTTTG   1200
GTGCACAAGG  CGGGCGGGGT  CATCCCCGAG  GTCCTCCGGG  TCCTCAAGGA  GAGGCGCACG   1260
GGGGAGGAAA  GGCCCATTCG  CTGGCCCGAG  ACCTGCCCCG  AGTGCGGCCA  CCGCCTCCTC   1320
AAGGAGGGGA  AGGTCCACCG  CTGCCCCAAC  CCCTTGTGCC  CCGCCAAGCG  CTTTGAGGCC   1380
ATCCGCCACT  TCGCCTCCCG  CAAGGCCATG  GACATCCAGG  GCCTGGGGGA  AAAGCTCATT   1440
GAGAGGCTTT  TGGAAAAGGG  GCTGGTCAAG  GACGTGGCCG  ACCTCTACCG  CTTGAGAAAG   1500
GAAGACCTGG  TGGGCCTGGA  GCGCATGGGG  GAGAAGAGCG  CCCAAAACCT  CCTCCGCGAG   1560
ATAGAGGAGA  GCAAGAAAAG  AGGCCTGGAG  CGCCTCCTCT  ACGCCTTGGG  GCTTCCCGGG   1620
```

-continued

```
GTGGGGGAGG  TCTTGGCCCG  GAACCTGGCG  GCCCGCTTCG  GGAACATGGA  CCGCCTCCTC    1680

GAGGCCAGCC  TGGAGGAGCT  CCTGGAGGTG  GAGGAGGTGG  GGGAGCTCAC  GGCGAGGGCC    1740

ATCCTGGAGA  CCTTGAAGGA  CCCCGCCTTC  CGCGACCTGG  TACGGAGGCT  CAAGGAGGCG    1800

GGGGTGGAGA  TGGAGGCCAA  GGAGAAGGGC  GGGGAGGCCC  TTAAAGGGCT  CACCTCCGTG    1860

ATCACCGGGG  AGCTTTCCCG  CCCCCGGGAA  GAGGTGAAGG  CCCTCCTAAG  GCGCCTCGGG    1920

GCCAAGGTGA  CGGACTCCGT  GAGCCGGAAG  ACGAGCTACC  TCGTGGTGGG  GGAGAACCCG    1980

GGGGAGAACC  CGGGGAGCAA  GCTGGAGAAG  GCCAGGGCCC  TCGGGGTCCC  CACCCTCACG    2040

GAGGAGGAGC  TCTACCGGCT  CCTGGAGGCG  CGGACGGGGA  AGAAGGCGGA  GGAGCTCGTC    2100

TAAAGGCTTC  C                                                             2111
```

( 2 ) INFORMATION FOR SEQ ID NO:2:

( i ) SEQUENCE CHARACTERISTICS:
  ( A ) LENGTH: 676 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:2:

```
Met  Thr  Leu  Glu  Glu  Ala  Arg  Lys  Arg  Val  Asn  Glu  Leu  Arg  Asp  Leu
  1              5                   10                  15

Ile  Arg  Tyr  His  Asn  Tyr  Arg  Tyr  Tyr  Val  Leu  Ala  Asp  Pro  Glu  Ile
                 20                  25                  30

Ser  Asp  Ala  Glu  Tyr  Asp  Arg  Leu  Leu  Arg  Glu  Leu  Lys  Glu  Leu  Glu
             35                  40                  45

Glu  Arg  Phe  Pro  Glu  Leu  Lys  Ser  Pro  Asp  Ser  Pro  Thr  Leu  Gln  Val
         50                  55                  60

Gly  Ala  Arg  Pro  Leu  Glu  Ala  Thr  Phe  Arg  Pro  Val  Arg  His  Pro  Thr
 65                  70                  75                  80

Arg  Met  Tyr  Ser  Leu  Asp  Asn  Ala  Phe  Asn  Leu  Asp  Glu  Leu  Lys  Ala
                 85                  90                  95

Phe  Glu  Glu  Arg  Ile  Glu  Arg  Ala  Leu  Gly  Arg  Lys  Gly  Pro  Phe  Ala
            100                 105                 110

Tyr  Thr  Val  Glu  His  Lys  Val  Asp  Gly  Leu  Ser  Val  Asn  Leu  Tyr  Tyr
        115                 120                 125

Glu  Glu  Gly  Val  Leu  Val  Tyr  Gly  Ala  Thr  Arg  Gly  Asp  Gly  Glu  Val
    130                 135                 140

Gly  Glu  Glu  Val  Thr  Gln  Asn  Leu  Leu  Thr  Ile  Pro  Thr  Ile  Pro  Arg
145                 150                 155                 160

Arg  Leu  Lys  Gly  Val  Pro  Glu  Arg  Leu  Glu  Val  Arg  Gly  Glu  Val  Tyr
                165                 170                 175

Met  Pro  Ile  Glu  Ala  Phe  Leu  Arg  Leu  Asn  Glu  Glu  Leu  Glu  Glu  Arg
            180                 185                 190

Gly  Glu  Arg  Ile  Phe  Lys  Asn  Pro  Arg  Asn  Ala  Ala  Ala  Gly  Ser  Leu
        195                 200                 205

Arg  Gln  Lys  Asp  Pro  Arg  Ile  Thr  Ala  Lys  Arg  Gly  Leu  Arg  Ala  Thr
    210                 215                 220

Phe  Tyr  Ala  Leu  Gly  Leu  Gly  Leu  Glu  Glu  Val  Glu  Arg  Glu  Gly  Val
225                 230                 235                 240

Ala  Thr  Gln  Phe  Ala  Leu  Leu  His  Trp  Leu  Lys  Glu  Lys  Gly  Phe  Pro
                245                 250                 255
```

-continued

```
Val  Glu  His  Gly  Tyr  Ala  Arg  Ala  Val  Gly  Ala  Glu  Gly  Val  Glu  Ala
          260                      265                     270

Val  Tyr  Gln  Asp  Trp  Leu  Lys  Lys  Arg  Arg  Ala  Leu  Pro  Phe  Glu  Ala
          275                      280                     285

Asp  Gly  Val  Val  Val  Lys  Leu  Asp  Glu  Leu  Ala  Leu  Trp  Arg  Glu  Leu
     290                      295                     300

Gly  Tyr  Thr  Ala  Arg  Ala  Pro  Arg  Phe  Ala  Ile  Ala  Tyr  Lys  Phe  Pro
305                      310                     315                          320

Ala  Glu  Glu  Lys  Glu  Thr  Arg  Leu  Leu  Asp  Val  Val  Phe  Gln  Val  Gly
               325                      330                          335

Arg  Thr  Gly  Arg  Val  Thr  Pro  Val  Gly  Ile  Leu  Glu  Pro  Val  Phe  Leu
               340                      345                     350

Glu  Gly  Ser  Glu  Val  Ser  Arg  Val  Thr  Leu  His  Asn  Glu  Ser  Tyr  Ile
          355                      360                     365

Glu  Glu  Leu  Asp  Ile  Arg  Ile  Gly  Asp  Trp  Val  Leu  Val  His  Lys  Ala
     370                      375                     380

Gly  Gly  Val  Ile  Pro  Glu  Val  Leu  Arg  Val  Leu  Lys  Glu  Arg  Arg  Thr
385                      390                     395                          400

Gly  Glu  Glu  Arg  Pro  Ile  Arg  Trp  Pro  Glu  Thr  Cys  Pro  Glu  Cys  Gly
               405                      410                          415

His  Arg  Leu  Leu  Lys  Glu  Gly  Lys  Val  His  Arg  Cys  Pro  Asn  Pro  Leu
               420                      425                     430

Cys  Pro  Ala  Lys  Arg  Phe  Glu  Ala  Ile  Arg  His  Phe  Ala  Ser  Arg  Lys
               435                      440                     445

Ala  Met  Asp  Ile  Gln  Gly  Leu  Gly  Glu  Lys  Leu  Ile  Glu  Arg  Leu  Leu
     450                      455                     460

Glu  Lys  Gly  Leu  Val  Lys  Asp  Val  Ala  Asp  Leu  Tyr  Arg  Leu  Arg  Lys
465                      470                     475                          480

Glu  Asp  Leu  Val  Gly  Leu  Glu  Arg  Met  Gly  Glu  Lys  Ser  Ala  Gln  Asn
                    485                      490                          495

Leu  Leu  Arg  Gln  Ile  Glu  Glu  Ser  Lys  Lys  Arg  Gly  Leu  Glu  Arg  Leu
               500                      505                     510

Leu  Tyr  Ala  Leu  Gly  Leu  Pro  Gly  Val  Gly  Glu  Val  Leu  Ala  Arg  Asn
          515                      520                     525

Leu  Ala  Ala  Arg  Phe  Gly  Asn  Met  Asp  Arg  Leu  Leu  Glu  Ala  Ser  Leu
     530                      535                     540

Glu  Glu  Leu  Leu  Glu  Val  Glu  Glu  Val  Gly  Glu  Leu  Thr  Ala  Arg  Ala
545                      550                     555                          560

Ile  Leu  Glu  Thr  Leu  Lys  Asp  Pro  Ala  Phe  Arg  Asp  Leu  Val  Arg  Arg
                    565                      570                          575

Leu  Lys  Glu  Ala  Gly  Val  Glu  Met  Glu  Ala  Lys  Glu  Lys  Gly  Gly  Glu
               580                      585                     590

Ala  Leu  Lys  Gly  Leu  Thr  Phe  Val  Ile  Thr  Gly  Glu  Leu  Ser  Arg  Pro
          595                      600                     605

Arg  Glu  Glu  Val  Lys  Ala  Leu  Leu  Arg  Arg  Leu  Gly  Ala  Lys  Val  Thr
     610                      615                     620

Asp  Ser  Val  Ser  Arg  Lys  Thr  Ser  Tyr  Leu  Val  Val  Gly  Glu  Asn  Pro
625                      630                     635                          640

Gly  Ser  Lys  Leu  Glu  Lys  Ala  Arg  Ala  Leu  Gly  Val  Pro  Thr  Leu  Thr
                    645                      650                     655

Glu  Glu  Glu  Leu  Tyr  Arg  Leu  Leu  Glu  Ala  Arg  Thr  Gly  Lys  Lys  Ala
               660                      665                     670

Glu  Glu  Leu  Val
          675
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:3:

Asp Ala Glu Tyr Asp Arg Leu
1               5

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:4:

Gly Ala Tyr Gly Cys Asn Gly Ala Arg Thr Ala Tyr Gly Ala Tyr Met
1             5                    10                    15

Gly Asn Tyr Thr
             20

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AGCGGATAAC AATTTCACAC AGGA                                                    24

( 2 ) INFORMATION FOR SEQ ID NO:6:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGCTCGTATG TTGTGTGGAA TTGTGAGCGG ATAACAATTT CACACAGGAA ACAGCTATGA      60

CCATGATTAC GAATTTAATA CGACTCACTA TAGGGAATTC GAGCTCGGTA CCCCAAGGTA    120

CACTAGGGCC                                                                                     130

( 2 ) INFORMATION FOR SEQ ID NO:7:

( i ) SEQUENCE CHARACTERISTICS:
        ( A ) LENGTH: 2051 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

| | | | | | | |
|---|---|---|---|---|---|---|
| ATGACCCTGG | AAGAGGCGAG | GAAGCGGGTA | AACGAGTTAC | GGGACCTCAT | CCGCTACCAC | 60 |
| AACTACCGCT | ACTACGTCCT | GGCGGACCCG | GAGATCTCCG | ACGCCGAGTA | CGACCGGCTT | 120 |
| CTTAGGGAGC | TCAAGGAGCT | TGAGGAGCGC | TTCCCCGAGC | TCAAAAGCCC | GGACTCCCCC | 180 |
| ACCCTTCAGG | TGGGGGCGAG | GCCTTTGGAG | GCCACCTTCC | GCCCCGTCCG | CCACCCCACC | 240 |
| CGCATGTACT | CCTTGGACAA | CGCCTTTAAC | CTTGACGAGC | TCAAGGCCTT | TGAGGAGCGG | 300 |
| ATAGAACGGG | CCCTGGGGCG | GAAGGGCCCC | TTCGCCTACA | CCGTGGAGCA | CAAGGTGGAC | 360 |
| GGGCTTTCCG | TGAACCTCTA | CTACGAGGAG | GGGGTCCTGG | TCTACGGGGC | CACCGCCGGG | 420 |
| GACGGGGAGG | TGGGGGAGGA | GGTCACCCAG | AACCTCCTCA | CCATCCCCAC | CATCCCGAGG | 480 |
| AGGCTCAAGG | GGGTGCCGGA | GCGCCTCGAG | GTCCGGGGGG | AGGTCTACAT | GCCCATAGAG | 540 |
| GCCTTCCTCC | GGCTCAACGA | GGAGCTGGAG | GAGCGGGGGG | AGAGGATCTT | CAAAAACCCT | 600 |
| AGGAATGCGG | CGGCGGGTTC | CTTAAGGCAA | AAAGACCCCC | GCATCACCGC | CAAGCGGGGC | 660 |
| CTCAGGGCCA | CCTTCTACGC | CTTAGGGCTT | GGGCTGGAGG | AGGTGGAGAG | GGAAGGGGTG | 720 |
| GCGACCCAGT | TTGCCCTCCT | CCACTGGCTC | AAGGAAAAAG | GCTTCCCCGT | GGAGCACGGC | 780 |
| TACGCCCGGG | CCGTGGGGGC | GGAAGGGGTG | GAGGCGGTCT | ACCAGGACTG | GCTCAAGAAG | 840 |
| CGGCGGGCGC | TTCCCTTTGA | GGCGGACGGG | GTGGTGGTGA | AGCTGGACGA | GCTTGCCCTT | 900 |
| TGGCGGGAGC | TCGGCTACAC | CGCCCGCGCC | CCCCGGTTCG | CCATCGCCTA | CAAGTTCCCC | 960 |
| GCCGAGGAGA | AGGAGACCCG | GCTTTTGGAC | GTGGTCTTCC | AGGTGGGGCG | CACCGGGCGG | 1020 |
| GTGACCCCCG | TGGGGATCCT | CGAGCCCGTC | TTCCTAGAGG | GCAGCGAGGT | CTCCCGGGTC | 1080 |
| ACCCTGCACA | ACGAGAGCTA | CATAGAGGAG | TTGGACATCC | GCATCGGGGA | CTGGGTTTTG | 1140 |
| GTGCACAAGG | CGGGCGGGGT | CATCCCCGAG | GTCCTCCGGG | TCCTCAAGGA | GAGGCGCACG | 1200 |
| GGGGAGGAAA | GGCCCATTCG | CTGGCCCGAG | ACCTGCCCCG | AGTGCGGCCA | CCGCCTCCTC | 1260 |
| AAGGAGGGGA | AGGTCCACCG | CTGCCCCAAC | CCCTTGTGCC | CCGCCAAGCG | CTTTGAGGCC | 1320 |
| ATCCGCCACT | TCGCCTCCCG | CAAGGCCATG | GACATCCAGG | GCCTGGGGGA | AAAGCTCATT | 1380 |
| GAGAGGCTTT | TGGAAAAGGG | GCTGGTCAAG | GACGTGGCCG | ACCTCTACCG | CTTGAGAAAG | 1440 |
| GAAGACCTGG | TGGGCCTGGA | GCGCATGGGG | GAGAAGAGCG | CCCAAAACCT | CCTCCGCGAG | 1500 |
| ATAGAGGAGA | GCAAGAAAAG | AGGCCTGGAG | CGCCTCCTCT | ACGCCTTGGG | GCTTCCCGGG | 1560 |
| GTGGGGGAGG | TCTTGGCCCG | GAACCTGGCG | GCCCGCTTCG | GAACATGGA | CCGCCTCCTC | 1620 |
| GAGGCCAGCC | TGGAGGAGCT | CCTGGAGGTG | GAGGAGGTGG | GGGAGCTCAC | GGCGAGGGCC | 1680 |
| ATCCTGGAGA | CCTTGAAGGA | CCCCGCCTTC | CGCGACCTGG | TACGGAGGCT | CAAGGAGGCG | 1740 |
| GGGGTGGAGA | TGGAGGCCAA | GGAGAAGGGC | GGGGAGGCCC | TTAAAGGGCT | CACCTCCGTG | 1800 |
| ATCACCGGGG | AGCTTTCCCG | CCCCCGGGAA | GAGGTGAAGG | CCCTCCTAAG | GCGCCTCGGG | 1860 |
| GCCAAGGTGA | CGGACTCCGT | GAGCCGGAAG | ACGAGCTACC | TCGTGGTGGG | GGAGAACCCG | 1920 |
| GGGGAGAACC | CGGGGAGCAA | GCTGGAGAAG | GCCAGGGCCC | TCGGGGTCCC | CACCCTCACG | 1980 |
| GAGGAGGAGC | TCTACCGGCT | CCTGGAGGCG | CGGACGGGA | AGAAGGCGGA | GGAGCTCGTC | 2040 |
| TAAAGGCTTC | C | | | | | 2051 |

( 2 ) INFORMATION FOR SEQ ID NO:8:

( i ) SEQUENCE CHARACTERISTICS:
( A ) LENGTH: 676 amino acids
( B ) TYPE: amino acid
( C ) STRANDEDNESS: Not Relevant ( D ) TOPOLOGY: linear ( i i ) MOLECULE TYPE: peptide ( x i ) SEQUENCE DESCRIPTION: SEQ ID NO:8:

| | | | | | | | | | | | | | | |
|---|---|---|---|---|---|---|---|---|---|---|---|---|---|---|
| Met | Thr | Leu | Glu | Glu | Ala | Arg | Lys | Arg | Val | Asn | Glu | Leu | Arg | Asp | Leu |
| 1 | | | | 5 | | | | | 10 | | | | | 15 | |
| Ile | Arg | Tyr | His | Asn | Tyr | Arg | Tyr | Tyr | Val | Leu | Ala | Asp | Pro | Glu | Ile |
| | | | 20 | | | | 25 | | | | | 30 | | | |
| Ser | Asp | Ala | Glu | Tyr | Asp | Arg | Leu | Leu | Arg | Glu | Leu | Lys | Glu | Leu | Glu |
| | | 35 | | | | | 40 | | | | | 45 | | | |
| Glu | Arg | Phe | Pro | Glu | Leu | Lys | Ser | Pro | Asp | Ser | Pro | Thr | Leu | Gln | Val |
| | 50 | | | | | 55 | | | | | 60 | | | | |
| Gly | Ala | Arg | Pro | Leu | Glu | Ala | Thr | Phe | Arg | Pro | Val | Arg | His | Pro | Thr |
| 65 | | | | | 70 | | | | | 75 | | | | | 80 |
| Arg | Met | Tyr | Ser | Leu | Asp | Asn | Ala | Phe | Asn | Leu | Asp | Glu | Leu | Lys | Ala |
| | | | | 85 | | | | | 90 | | | | | 95 | |
| Phe | Glu | Glu | Arg | Ile | Glu | Arg | Ala | Leu | Gly | Arg | Lys | Gly | Pro | Phe | Ala |
| | | | 100 | | | | | 105 | | | | | 110 | | |
| Tyr | Thr | Val | Glu | His | Lys | Val | Asp | Gly | Leu | Ser | Val | Asn | Leu | Tyr | Tyr |
| | | 115 | | | | | 120 | | | | | 125 | | | |
| Glu | Glu | Gly | Val | Leu | Val | Tyr | Gly | Ala | Thr | Arg | Gly | Asp | Gly | Glu | Val |
| | 130 | | | | | 135 | | | | | 140 | | | | |
| Gly | Glu | Glu | Val | Thr | Gln | Asn | Leu | Leu | Thr | Ile | Pro | Thr | Ile | Pro | Arg |
| 145 | | | | | 150 | | | | | 155 | | | | | 160 |
| Arg | Leu | Lys | Gly | Val | Pro | Glu | Arg | Leu | Glu | Val | Arg | Gly | Glu | Val | Tyr |
| | | | | 165 | | | | | 170 | | | | | 175 | |
| Met | Pro | Ile | Glu | Ala | Phe | Leu | Arg | Leu | Asn | Glu | Glu | Leu | Glu | Glu | Arg |
| | | | 180 | | | | | 185 | | | | | 190 | | |
| Gly | Glu | Arg | Ile | Phe | Lys | Asn | Pro | Arg | Asn | Ala | Ala | Ala | Gly | Ser | Leu |
| | | 195 | | | | | 200 | | | | | 205 | | | |
| Arg | Gln | Lys | Asp | Pro | Arg | Ile | Thr | Ala | Lys | Arg | Gly | Leu | Arg | Ala | Thr |
| | 210 | | | | | 215 | | | | | 220 | | | | |
| Phe | Tyr | Ala | Leu | Gly | Leu | Gly | Leu | Glu | Glu | Val | Glu | Arg | Glu | Gly | Val |
| 225 | | | | | 230 | | | | | 235 | | | | | 240 |
| Ala | Thr | Gln | Phe | Ala | Leu | Leu | His | Trp | Leu | Lys | Glu | Lys | Gly | Phe | Pro |
| | | | | 245 | | | | | 250 | | | | | 255 | |
| Val | Glu | His | Gly | Tyr | Ala | Arg | Ala | Val | Gly | Ala | Glu | Gly | Val | Glu | Ala |
| | | | 260 | | | | | 265 | | | | | 270 | | |
| Val | Tyr | Gln | Asp | Trp | Leu | Lys | Lys | Arg | Arg | Ala | Leu | Pro | Phe | Glu | Ala |
| | | 275 | | | | | 280 | | | | | 285 | | | |
| Asp | Gly | Val | Val | Val | Lys | Leu | Asp | Glu | Leu | Ala | Leu | Trp | Arg | Glu | Leu |
| | 290 | | | | | 295 | | | | | 300 | | | | |
| Gly | Tyr | Thr | Ala | Arg | Ala | Pro | Arg | Phe | Ala | Ile | Ala | Tyr | Lys | Phe | Pro |
| 305 | | | | | 310 | | | | | 315 | | | | | 320 |
| Ala | Glu | Glu | Lys | Glu | Thr | Arg | Leu | Leu | Asp | Val | Val | Phe | Gln | Val | Gly |
| | | | | 325 | | | | | 330 | | | | | 335 | |
| Arg | Thr | Gly | Arg | Val | Thr | Pro | Val | Gly | Ile | Leu | Glu | Pro | Val | Phe | Leu |
| | | | 340 | | | | | 345 | | | | | 350 | | |
| Glu | Gly | Ser | Glu | Val | Ser | Arg | Val | Thr | Leu | His | Asn | Glu | Ser | Tyr | Ile |
| | | 355 | | | | | 360 | | | | | 365 | | | |
| Glu | Glu | Leu | Asp | Ile | Arg | Ile | Gly | Asp | Trp | Val | Leu | Val | His | Lys | Ala |
| | 370 | | | | | 375 | | | | | 380 | | | | |
| Gly | Gly | Val | Ile | Pro | Glu | Val | Leu | Arg | Val | Leu | Lys | Glu | Arg | Arg | Thr |
| 385 | | | | | 390 | | | | | 395 | | | | | 400 |

|     |     |     |     |     |     |     |     |     |     |     |     |     |     |     |
| --- | --- | --- | --- | --- | --- | --- | --- | --- | --- | --- | --- | --- | --- | --- |
| Gly | Glu | Glu | Arg | Pro<br>405 | Ile | Arg | Trp | Pro | Glu<br>410 | Thr | Cys | Pro | Glu | Cys<br>415 | Gly |
| His | Arg | Leu | Leu<br>420 | Lys | Glu | Gly | Lys | Val<br>425 | His | Arg | Cys | Pro | Asn<br>430 | Pro | Leu |
| Cys | Pro | Ala<br>435 | Lys | Arg | Phe | Glu | Ala<br>440 | Ile | Arg | His | Phe | Ala<br>445 | Ser | Arg | Lys |
| Ala | Met | Asp<br>450 | Ile | Gln | Gly | Leu<br>455 | Gly | Glu | Lys | Leu | Ile<br>460 | Glu | Arg | Leu | Leu |
| Glu<br>465 | Lys | Gly | Leu | Val | Lys<br>470 | Asp | Val | Ala | Asp | Leu<br>475 | Tyr | Arg | Leu | Arg | Lys<br>480 |
| Glu | Asp | Leu | Val | Gly<br>485 | Leu | Glu | Arg | Met | Gly<br>490 | Glu | Lys | Ser | Ala | Gln<br>495 | Asn |
| Leu | Leu | Arg | Gln<br>500 | Ile | Glu | Glu | Ser | Lys<br>505 | Lys | Arg | Gly | Leu | Glu<br>510 | Arg | Leu |
| Leu | Tyr | Ala<br>515 | Leu | Gly | Leu | Pro | Gly<br>520 | Val | Gly | Glu | Val | Leu<br>525 | Ala | Arg | Asn |
| Leu | Ala | Ala<br>530 | Arg | Phe | Gly | Asn | Met<br>535 | Asp | Arg | Leu | Leu<br>540 | Glu | Ala | Ser | Leu |
| Glu<br>545 | Glu | Leu | Leu | Glu | Val<br>550 | Glu | Glu | Val | Gly | Glu<br>555 | Leu | Thr | Ala | Arg | Ala<br>560 |
| Ile | Leu | Glu | Thr | Leu<br>565 | Lys | Asp | Pro | Ala | Phe<br>570 | Arg | Asp | Leu | Val | Arg<br>575 | Arg |
| Leu | Lys | Glu | Ala<br>580 | Gly | Val | Glu | Met | Glu<br>585 | Ala | Lys | Glu | Lys | Gly<br>590 | Gly | Glu |
| Ala | Leu | Lys<br>595 | Gly | Leu | Thr | Phe | Val<br>600 | Ile | Thr | Gly | Glu | Leu<br>605 | Ser | Arg | Pro |
| Arg | Glu<br>610 | Glu | Val | Lys | Ala | Leu<br>615 | Leu | Arg | Arg | Leu | Gly<br>620 | Ala | Lys | Val | Thr |
| Asp<br>625 | Ser | Val | Ser | Arg | Lys<br>630 | Thr | Ser | Tyr | Leu | Val<br>635 | Val | Gly | Glu | Asn | Pro<br>640 |
| Gly | Ser | Lys | Leu | Glu<br>645 | Lys | Ala | Arg | Ala | Leu<br>650 | Gly | Val | Pro | Thr | Leu<br>655 | Thr |
| Glu | Glu | Glu | Leu<br>660 | Tyr | Arg | Leu | Leu | Glu<br>665 | Ala | Arg | Thr | Gly | Lys<br>670 | Lys | Ala |
| Glu | Glu | Leu<br>675 | Val |     |     |     |     |     |     |     |     |     |     |     |     |

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CTGGCTTATC GAAATTAAT                    19

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CCAGGGTCAT TTTATTTTCT CCATGTACAA AT 32

( 2 ) INFORMATION FOR SEQ ID NO:11:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:11:

CATGGAGAAA ATAAAATGAC CCTGGAAGAG GCG 33

( 2 ) INFORMATION FOR SEQ ID NO:12:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:12:

AAGCCGGTCG TACTCGGC 18

( 2 ) INFORMATION FOR SEQ ID NO:13:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:13:

GTTTTTCATG GTGCACCTGA CGCCTGG 27

( 2 ) INFORMATION FOR SEQ ID NO:14:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:14:

GTTTCATGGT GCACCTGACG CCTCT 25

( 2 ) INFORMATION FOR SEQ ID NO:15:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:15:

GTCATGGTGC ACCTGACGCC TCA 23

(2) INFORMATION FOR SEQ ID NO:16:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:16:

GGAGAAGTCT GCCGTTACTG CC               22

(2) INFORMATION FOR SEQ ID NO:17:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:17:

GACACCATGG TGCACCTGAC TCCTGAGGAG AAGTCTGCCG TTACTGCCCT G     51

(2) INFORMATION FOR SEQ ID NO:18:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:18:

CTGTGGTACC ACGTGGACTG AGGACTCCTC TTCAGACGGC AATGACGGGA C     51

(2) INFORMATION FOR SEQ ID NO:19:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:19:

TGGTACCACG TGGACTGAGG AC               22

(2) INFORMATION FOR SEQ ID NO:20:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:20:

TCCTCTTCAG ACGGCAATGA CGTC              24

(2) INFORMATION FOR SEQ ID NO:21:

(i) SEQUENCE CHARACTERISTICS:
    (A) LENGTH: 26 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

ACCTCTTCAG ACGGCAATCG CGTTTC     26

( 2 ) INFORMATION FOR SEQ ID NO:22:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

CCCTCTTCAG ACGGCAATCG CGTTTTTC     28

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:23:

Met  Val  His  Leu  Thr  Pro  Glu  Glu  Lys  Ser  Ala  Val  Thr  Ala  Leu
    1              5                        10                       15

( 2 ) INFORMATION FOR SEQ ID NO:24:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:24:

Met  Val  His  Leu  Thr  Pro  Val  Glu  Lys  Ser  Ala  Val  Thr  Ala  Leu
    1              5                        10                       15

( 2 ) INFORMATION FOR SEQ ID NO:25:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

CAACTTCATC CACGTTCACC TTGCC     25

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (i i) MOLECULE TYPE: DNA (x i) SEQUENCE DESCRIPTION: SEQ ID NO:26:

AGGGCAGGAG CCAGGGCTGG GG    22

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:27:

TCAGCCTTAC AACGTGTCTC TGCTT    25

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:28:

GTATGGCCTC TAAAAACATG GCCCC    25

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:29:

CAGTGGAAGA ATGGCATTCT GTT    23

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:30:

GGCATGCTTT GATGACGCTT CTG    23

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:31:

ATGGTGCACC TGACTCCTGA 20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

GGAGAAGTCT GCCGTTACTG 20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

ATGGTGCACC TGACTCCTGT 20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

GGCTGTGCTG ACCATCGACG 20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

AGAAAGGGAC TGAAGCTGCT 20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

GGCTGTGCTG ACCATCGACA 20

(2) INFORMATION FOR SEQ ID NO:37:

```
        ( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:37:

A T T A A A G A A A   A T A T C A T C T T                                                                 2 0

( 2 ) INFORMATION FOR SEQ ID NO:38:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:38:

T G G T G T T T C C   T A T G A T G A A T                                                                 2 0

( 2 ) INFORMATION FOR SEQ ID NO:39:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:39:

A C C A T T A A A G   A A A A T A T C A T                                                                 2 0
```

We claim:

1. A method for distinguishing a first nucleotide sequence which differs by at least a single base from a second nucleotide sequence comprising:

providing a sample potentially containing the first nucleotide sequence and the second nucleotide sequence;

providing a first oligonucleotide set of at least two oligonucleotides suitable for ligation together at a first ligation junction and for hybridization without mismatch at the first ligation junction to the first nucleotide sequence but not to the second nucleotide sequence, wherein the at least two oligonucleotides hybridize adjacent to one another on the first nucleotide sequence and have a hybridization temperature of about 50° C. to 85° C.;

providing a thermocyclable ligase which does not become irreversibly denatured and lose its catalytic activity when subjected to temperatures ranging from about 50° C. to 105° C.;

blending the sample, the at least two oligonucleotides, and the thermocyclable ligase to form an amplification mixture;

subjecting the amplification mixture to a series of cycles comprising a denaturation treatment, wherein the hybridized first oligonucleotide set is separated from the first nucleotide sequence or from the second nucleotide sequence, and a thermal hybridization treatment at a temperature of 50°–85° C., wherein the oligonucleotides of the first oligonucleotide set, when hybridized to the first nucleotide sequence, ligate to one another to amplify linearly a sequence of nucleotides complementary to the first nucleotide sequence and, when hybridized to the second nucleotide sequence, do not ligate together and individually separate from the second nucleotide sequence during the denaturation treatment; and detecting the presence of the first nucleotide sequence in the sample by detecting the presence of ligated oligonucleotides of the first oligonucleotide set.

2. A method according to claim 1, wherein the denaturation treatment is at a temperature of about 90° C. to 105° C.

3. A method according to claim 1, wherein said subjecting amplifies the sequence of nucleotides complementary to the first nucleotide sequence by about 50 to about 500 fold more than if a single base mismatch were present at the first ligation junction.

4. A method according to claim 1, wherein said subjecting amplifies the sequence of nucleotides complementary to the first nucleotide sequence by at least about 100 fold more than if the first nucleotide sequence were not present in the sample.

5. A method according to claim 1, wherein said subjecting is repeated for 5 to 20 cycles.

6. A method according to claim 1, wherein the first nucleotide sequence can be distinguished in the sample when present in an amount down to 1 femtomole.

7. A method according to claim 1, wherein the thermal hybridization step discriminates between the first nucleotide sequence and the second nucleotide sequence based on a distinguishing nucleotide at the first ligation junction.

8. A method according to claim 7, wherein the difference between the first and second nucleotide sequences is a single nucleic acid base pair change.

9. A method according to claim 7, wherein the difference between the first and second nucleotide sequences is a nucleic acid deletion.

10. A method according to claim 7, wherein the difference between the first and second nucleotide sequences is a nucleic acid insertion.

11. A method according to claim 7, wherein A:A mismatches at the distinguishing nucleotide have a mismatched/complementary percentage of 0.4 to <0.1%.

12. A method according to claim 7, wherein T:T mismatches at the distinguishing nucleotide have a mismatched/complementary percentage of 0.7 to 1.0%.

13. A method according to claim 7, wherein G:T mismatches at the distinguishing nucleotide have a mismatched/complementary percentage of 1.0 to 1.5%.

14. A method according to claim 7, wherein C:T mismatches at the distinguishing nucleotide have a mismatched/complementary percentage of 0.4 to <0.1%.

15. A method according to claim 7, wherein G:A mismatches at the distinguishing nucleotide have a mismatched/complementary percentage of 0.4 to <0.1%.

16. A method according to claim 7, wherein C:A mismatches at the distinguishing nucleotide have a mismatched/complementary percentage of 0.4 to <0.1%.

17. A method according to claim 1, further comprising:
amplifying the first nucleotide sequence in the sample prior to said blending by subjecting the sample to a polymerase chain reaction process.

18. A method according to claim 7, wherein the distinguishing nucleotide is complementary to the oligonucleotide of the first oligonucleotide set having its 3' end at the first ligation junction.

19. A method according to claim 1, wherein the first oligonucleotide set is in molar excess of the first nucleotide sequence.

20. A method according to claim 1, wherein the ligase is isolated from *Thermus aquaticus*.

21. A method according to claim 20, wherein the ligase has an amino acid sequence corresponding to SEQ. ID. No. 2.

22. A method according to claim 1, wherein said detecting comprises:
capturing a hook attached to at least one of the oligonucleotides of the first oligonucleotide set.

23. A method according to claim 22, wherein the hook is selected from the group consisting of antigens, biotin, and DNA binding proteins.

24. A method according to claim 1, wherein said detecting comprises:
detecting a label attached to at least one of the oligonucleotides of the first oligonucleotide set.

25. A method according to claim 24, wherein the label is selected from the group consisting of chromophores, fluorescent moieties, enzymes, antigens, chemiluminescent moieties, and electrochemical detecting moieties.

26. A method according to claim 1, wherein said detecting comprises:
separating products of said subjecting by size.

27. A method according to claim 1, wherein the oligonucleotides of the first oligonucleotide set are deoxyribonucleic acids.

28. A method according to claim 1, wherein the oligonucleotides of the first oligonucleotide set each have a hybridization temperature of about 66° to 70° C.

29. A method according to claim 1, wherein the amplification mixture further includes a carrier DNA.

30. A method according to claim 29, wherein the carrier DNA is salmon sperm DNA.

31. A method according to claim 1, wherein the first nucleotide sequence is present as a first strand of a double stranded DNA molecule.

32. A method according to claim 31, further comprising:
providing a second oligonucleotide set of at least two oligonucleotides suitable for ligation together at a second ligation junction and for hybridization without mismatch at the second ligation junction to a first complementary nucleotide sequence but not to a second complementary nucleotide sequence, wherein the first complementary nucleotide sequence is complementary to the first nucleotide sequence and is present in the second strand of the DNA and the at least two oligonucleotides of the second oligonucleotide set hybridize adjacent to one another on the first complementary nucleotide sequence and have a hybridization temperature of about 50° to 85° C., wherein the first and second complementary nucleotide sequences differ by at least a single base at the second ligation junction, and
blending the second oligonucleotide set with the amplification mixture, whereby said subjecting exponentially amplifies the first and first complementary nucleotide sequences in the DNA and said detecting further comprises detecting the presence of the first complementary nucleotide sequence in the sample by detecting the presence of ligated oligonucleotides of the second oligonuclcotide set.

33. A method according to claim 32, wherein the thermal hybridization step discriminates between the first nucleotide sequence and the second nucleotide sequence and between the first complementary nucleotide sequence and the second complementary nucleotide sequence based on distinguishing nucleotides at the first ligation junction and the second ligation junction, respectively.

34. A method according to claim 33, wherein the difference between the first and second complementary nucleotide sequences is a single nucleic acid base pair change.

35. A method according to claim 33, wherein the difference between the first and second complementary nucleotide sequences is a nucleic acid deletion.

36. A method according to claim 33, wherein the difference between the first and second complementary nucleotide sequences is a nucleic acid insertion.

37. A method according to claim 33, wherein A:A and T:T mismatches at the distinguishing nucleotides have a mismatched/complementary percentage of 0.6 to 1.3%.

38. A method according to claim 33, wherein T:T and A:A mismatches at the distinguishing nucleotides have a mismatched/complementary percentage of <0.2%.

39. A method according to claim 33, wherein G:T and C:A mismatches at the distinguishing nucleotides have a mismatched/complementary percentage of 0.6 to 1.3%.

40. A method according to claim 33, wherein G:A and C:T mismatches at the distinguishing nucleotides have a mismatched/complementary percentage of <0.2%.

41. A method according to claim 31, wherein said subjecting is repeated for up to 40 cycles.

42. A method according to claim 31, wherein the first nucleotide sequence and the first complementary nucleotide sequence can be distinguished in the sample when present in an amount of 0.001 to 100 attomoles.

43. A method according to claim 31, wherein the ligase is isolated from *Thermus aquaticus*.

44. A method according to claim 43, wherein the ligase has an amino acid sequence corresponding to SEQ.ID.NO.2.

45. A method for together amplifying and distinguishing nucleotide sequences complementary to a first nucleotide sequence and a second nucleotide sequence, wherein the first and second nucleotide sequences differ by at least one base, comprising:

providing a sample potentially containing the first nucleotide sequence and the second nucleotide sequence;

providing a first oligonucleotide set of at least two oligonucleotides suitable for ligation together at a first ligation junction and for hybridization without mismatch at the first ligation junction to the first nucleotide sequence, but not to the second nucleotide sequence, wherein the oligonucleotides of the first set hybridize adjacent to one another on the first nucleotide sequence and have a hybridization temperature of about 50° C. to 85° C.;

providing a second oligonucleotide set of at least two oligonucleotides suitable for ligation together at a second ligation junction and for hybridization without mismatch at the second ligation junction to the second nucleotide sequence, but not to the first nucleotide sequence, wherein the oligonucleotides of the second set hybridize adjacent to one another on the second nucleotide sequence and have a hybridization temperature of about 50° C. to 85° C.;

providing a thermocyclable ligase which does not become irreversibly denatured and lose its catalytic activity when subjected to temperatures ranging from about 50° C. to 105° C.;

blending the sample, the first set of oligonucleotides, and the thermocyclable ligase to form a first amplification mixture;

blending the sample, the second set of oligonucleotides, and the thermocyclable ligase to form a second amplification mixture;

subjecting the first and second amplification mixtures to a series of cycles comprising a denaturation treatment, wherein the first oligonucleotide set is separated from the first nucleotide sequence while the second oligonucleotide set is separated from the second nucleotide sequence, and a thermal hybridization treatment at a temperature of about 50° C. to 85° C., wherein the first oligonucleotide set hybridizes to the first nucleotide sequence and its oligonucleotides ligate to one another while the second oligonucleotide set hybridizes to the second nucleotide sequence and its oligonucleotides ligate to one another, to amplify linearly nucleotide sequences complementary to the first nucleotide sequence and to the second nucleotide sequence;

detecting the presence of the first nucleotide sequence in the sample by detecting the presence of ligated oligonucleotides of the first oligonucleotide set; and detecting the presence of the second nucleotide sequence in the sample by detecting the presence of ligated oligonucleotides of the second oligonucleotide set.

46. A method according to claim 45, wherein the denaturation treatment is at a temperature of about 90° C. to 105° C.

47. A method according to claim 45, wherein said subjecting amplifies the sequence of nucleotides complementary to the first and second nucleotide sequences by about 50 to about 500 fold more than if a single base mismatch were present at the first and second ligation junctions.

48. A method according to claim 45, wherein said subjecting amplifies the sequence of nucleotides complementary to the first and second nucleotide sequences by atleast about 100 fold more than if the first and second nucleotide sequences were not present in the sample.

49. A method according to claim 45, wherein said subjecting is repeated for 5 to 20 cycles.

50. A method according to claim 45, wherein the first nucleotide sequence can be distinguished in the sample when present in an amount down to 1 femtomole.

51. A method according to claim 45, wherein the first and second amplification mixtures are formed separately.

52. A method according to claim 45, wherein the first and second oligonucleotide sets are in molar excess of the first and second nucleotide sequences.

53. A method according to claim 45, wherein the ligase is isolated from *Thermus aquaticus*.

54. A method according to claim 53, wherein the ligase has a sequence corresponding to SEQ.ID.No.2.

55. A method according to claim 45, wherein at least one of said detecting steps comprises:

capturing a hook attached to at least one of the oligonucleotides of the first or second oligonucleotide sets.

56. A method according to claim 55, wherein the hook is selected from the group consisting of antigens, biotin, and DNA binding proteins.

57. A method according to claim 45, wherein at least one of said detecting steps comprises:

detecting a label attached to at least one of the oligonucleotides of the first or second oligonucleotide sets.

58. A method according to claim 57, wherein the label is selected from the group consisting of chromophores, fluorescent moieties, enzymes, antigens, chemiluminescent moieties, and electrochemical detecting moieties.

59. A method according to claim 55, wherein at least one of said detecting steps comprises:

separating products of said subjecting by size.

60. A method according to claim 45, wherein the oligonucleotides of the first and second oligonucleotide sets are deoxyribonucleic acids.

61. A method according to claim 45, wherein the oligonucleotides of the first and second oligonucleotide sets each have a hybridization temperature of about 66° to 70° C.

62. A method according to claim 45, wherein at least one of the amplification mixtures further includes a carrier DNA.

63. A method according to claim 62, wherein the carrier DNA is salmon sperm DNA.

64. A method according to claim 45, wherein the thermal hybridization step discriminates between the first nucleotide sequence and the second nucleotide sequence based on a distinguishing nucleotide at the first ligation junction.

65. A method according to claim 64, wherein the difference between the first and second nucleotide sequences is a single nucleic acid base pair change.

66. A method according to claim 64, wherein the difference between the first and second nucleotide sequences is a nucleic acid deletion.

67. A method according to claim 64, wherein the difference between the first and second nucleotide sequences is a nucleic acid insertion.

68. A method according to claim 64, wherein A:A mismatches at the distinguishing nucleotide have a mismatched/complementary percentage of 0.4 to <1.0%.

69. A method according to claim 64, wherein T:T mismatches at the distinguishing nucleotide have a mismatched/complementary percentage of 0.7 to 1.0%.

70. A method according to claim 64, wherein G:T mismatches at the distinguishing nucleotide have a mismatched/complementary percentage of 1.0 to 1.5%.

71. A method according to claim 64, wherein C:T mismatches at the distinguishing nucleotide have a mismatched/complementary percentage of 0.4 to <1.0%.

72. A method according to claim 64, wherein G:A mismatches at the distinguishing nucleotide have a mismatched/complementary percentage of 0.4 to <1.0%.

73. A method according to claim 64, wherein C:A mismatches at the distinguishing nucleotide have a mismatched/complementary percentage of 0.4 to <1.0%.

74. A method according to claim 45, further comprising:
amplifying the first nucleotide sequence and the second nucleotide sequence in the sample prior to said blending by subjecting the sample to a polymerase chain reaction process.

75. A method according to claim 64, wherein the distinguishing nucleotide is complementary to the oligonucleotide of the first oligonucleotide set having its 3' end at the first ligation junction.

76. A method according to claim 45, wherein the first nucleotide sequence is present as a first strand of a first double stranded DNA molecule, while the second nucleotide sequence is present as a first strand of a second double stranded DNA molecule.

77. A method according to claim 76 further comprising:
providing a third oligonucleotide set of at least two oligonucleotides suitable for ligation together at a third ligation junction and for hybridization without mismatch at the third ligation junction to a third nucleotide sequence, the third nucleotide sequence being complementary to the first nucleotide sequence and present in the second strand of the first DNA molecule;
providing a fourth oligonucleotide set of at least two oligonucleotides suitable for ligation together at a fourth ligation junction and for hybridization without mismatch at the fourth ligation junction to a fourth nucleotide sequence, the fourth nucleotide sequence being complementary to the second nucleotide sequence and present in the second strand of the second DNA molecule;
blending the third oligonucleotide set with the first amplification mixture;
blending the fourth oligonucleotide set with the second amplification mixture, whereby said subjecting exponentially amplifies the first, second, third, and fourth nucleotide sequences;
detecting the presence of the third nucleotide sequence in the sample by detection of the presence of ligated oligonucleotides of the third oligonucleotide set; and
detecting the presence of the fourth nucleotide sequence in the sample by detection of the presence of the ligated oligonucleotides of the fourth oligonucleotide set.

78. A method according to claim 77, wherein the thermal hybridization step discriminates between the first nucleotide sequence and the second nucleotide sequence based on distinguishing nucleotides at the first ligation junction and the second ligation junction and between the third nucleotide sequence and the fourth nucleotide sequence based on distinguishing nucleotides at the third ligation junction and the fourth ligation junction.

79. A method according to claim 78, wherein the difference between the first and second nucleotide sequences and between the third and fourth nucleotide sequences is a single nucleic acid base pair change.

80. A method according to claim 78, wherein the difference between the first and second nucleotide sequences and between the third and fourth nucleotide sequences is a nucleic acid deletion.

81. A method according to claim 78, wherein the difference between the first and second nucleotide sequences and between the third and fourth nucleotide sequences is a nucleic acid insertion.

82. A method according to claim 78, wherein A:A and T:T mismatches at the distinguishing nucleotides have a mismatched/complementary percentage of 0.6 to 1.3%.

83. A method according to claim 78, wherein T:T and A:A mismatches at the distinguishing nucleotides have a mismatched/complementary percentage of <0.2%.

84. A method according to claim 78, wherein G:T and C:A mismatches at the distinguishing nucleotides have a mismatched/complementary percentage of 0.6 to 1.3%.

85. A method according to claim 78, wherein G:A and C:T mismatches at the distinguishing nucleotides have a mismatched/complementary percentage of <0.2%.

86. A method according to claim 77, wherein said subjecting is repeated for up to 40 cycles.

87. A method according to claim 77, wherein the first nucleotide sequence and the first complementary nucleotide sequence can be detected in the sample at a concentration of 0.001 to 100 attomoles.

88. A method according to claim 77, wherein the ligase is isolated from *Thermus aquaticus*.

89. A method according to claim 88, wherein the ligase has an amino acid sequence corresponding to SEQ.ID.NO.2.

* * * * *

UNITED STATES PATENT AND TRADEMARK OFFICE
CERTIFICATE OF CORRECTION

PATENT NO. : 5,830,711
DATED : November 3, 1998
INVENTOR(S) : Barany, et al

It is certified that error appears in the above-identified patent and that said Letters Patent is hereby corrected as shown below:

On the title page: [*] Notice: replace "Pat. No. 5,494,870" with -- Pat. No. 5,494,810--.

Item [56] Attorney, Agent, Firm: replace "Hagargrave" with --Hargrave--.

Signed and Sealed this

Thirtieth Day of March, 1999

Attest:

Attesting Officer

Q. TODD DICKINSON

Acting Commissioner of Patents and Trademarks